US007951781B2

(12) United States Patent
McCray, Jr. et al.

(10) Patent No.: US 7,951,781 B2
(45) Date of Patent: May 31, 2011

(54) METHODS AND COMPOSITIONS RELATED TO PLUNC SURFACTANT POLYPEPTIDES

(75) Inventors: Paul B. McCray, Jr., Iowa City, IA (US); Lokesh Gakhar, Iowa City, IA (US); Rama K. Mallampalli, Iowa City, IA (US); Subramanian Ramaswamy, Iowa City, IA (US); Jennifer Bartlett, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 669 days.

(21) Appl. No.: 11/934,581

(22) Filed: Nov. 2, 2007

(65) Prior Publication Data

US 2009/0110756 A1 Apr. 30, 2009

Related U.S. Application Data

(60) Provisional application No. 60/864,062, filed on Nov. 2, 2006.

(51) Int. Cl.
A61K 38/08 (2006.01)
A61K 38/16 (2006.01)
A61K 39/215 (2006.01)
C07K 14/135 (2006.01)

(52) U.S. Cl. ....... 514/21.6; 514/1.8; 514/21.2; 530/328; 530/324; 424/222.1

(58) Field of Classification Search ............... None
See application file for complete search history.

(56) References Cited

U.S. PATENT DOCUMENTS

| | | | |
|---|---|---|---|
| 2001/0003599 A1 | 6/2001 | Chinn et al. | 427/2.24 |
| 2003/0180303 A1 | 9/2003 | Gazzano-Santoro et al. | 424/165.1 |
| 2003/0194377 A1 | 10/2003 | Carroll et al. | 424/45 |
| 2004/0142891 A1 | 7/2004 | Groot et al. | 514/44 |
| 2005/0181375 A1 | 8/2005 | Aziz et al. | 435/6 |
| 2005/0192221 A1 | 9/2005 | McCray et al. | 514/12 |
| 2006/0035852 A1 | 2/2006 | Sahin et al. | 514/44 |
| 2006/0078506 A1 | 4/2006 | Niven et al. | 424/45 |
| 2006/0194728 A1* | 8/2006 | Killian et al. | 514/12 |

FOREIGN PATENT DOCUMENTS

| | | |
|---|---|---|
| EP | 0100910 | 2/1984 |
| EP | 0110498 | 6/1984 |
| EP | 0119056 | 9/1984 |
| EP | 0145005 | 6/1985 |
| EP | 0251449 | 1/1988 |
| EP | 0286011 | 10/1988 |
| EP | 0348967 | 1/1990 |
| EP | 0368823 | 5/1990 |
| EP | 0593094 | 4/1994 |
| WO | WO 86/03408 | 6/1986 |
| WO | WO 87/06943 | 11/1987 |
| WO | WO 88/03170 | 5/1988 |
| WO | WO 89/04326 | 5/1989 |
| WO | WO 91/00871 | 1/1991 |
| WO | WO 91/18015 | 11/1991 |
| WO | WO 92/22315 | 12/1992 |
| WO | WO 93/06228 | 4/1993 |
| WO | WO 95/32992 | 12/1995 |
| WO | WO 00/08206 | 2/2000 |
| WO | WO 01/36478 | 5/2001 |
| WO | WO 01/79492 | 10/2001 |
| WO | WO 03/087143 | 10/2003 |
| WO | WO 03/087143 A2 * | 10/2003 |
| WO | WO 2005/056045 | 6/2005 |

OTHER PUBLICATIONS

Beamer et al., "Crystal structure of human BPI and two bound phospholipids at 2.4 angstrom resolution," *Science*, 276:1861-1864, 1997.
Beamer et al., "The BPI/LBP family of proteins: a structural analysis of conserved regions," *Protein Sci.*, 7:906-914, 1998.
Beamer et al., "The three-dimensional structure of human bactericidal/permeability-increasing protein: implications for understanding protein-lipopolysaccharide interactions," *Biochem. Pharmacol.*, 57:225-229, 1999.
Beeley et al., "Isolation and characterization of latherin, a surface-active protein from horse sweat," *Biochem J.* 235:645-50, 1986.
Bingle and Bingle, "Characterisation of the human plunc gene, a gene product with an upper airways and nasopharyngeal restricted expression pattern," *Biochim. Biophys. Acta*, 1493:363-367, 2000.
Bingle and Craven, "PLUNC: a novel family of candidate host defence proteins expressed in the upper airways and nasopharynx," *Hum. Molec. Genet.*, 11:937-943, 2002.
Bone, "The pathogenesis of sepsis," *Annals Int Med*, 115:457-469, 1991.
Bruce et al., "The implications of the structure of the bactericidal/permeability-increasing protein on the lipid-transfer function of the cholesteryl ester transfer protein," *Curr. Opin. Struct. Biol.*, 8:426-434, 1998.
Campos et al., "Purification and characterization of PLUNC from human tracheobronchial secretions," *Am. J. Respir. Cell Mol. Biol.*, 30:184-192, 2004.
Database NCBI, "Burkholderia sp. 383," Database Accession No. ABB08889, Oct. 20, 2005.
Database NCBI, "*Homo sapiens* (human)," Database Accession No. AAF70860, Oct. 2, 2000.
Database NCBI, "*Homo sapiens* (human)," Database Accession No. AAM00283, Apr. 2, 2002.

(Continued)

Primary Examiner — Cecilia Tsang
Assistant Examiner — Satyanarayana R Gudibande
(74) Attorney, Agent, or Firm — Fulbright & Jaworski

(57) ABSTRACT

Embodiments include compositions and methods for lower the surface tension of a liquid-air interface by contacting such interface with all or part of a PLUNC polypeptide.

24 Claims, 19 Drawing Sheets

OTHER PUBLICATIONS

Database NCBI, "*Homo sapiens* (human)," Database Accession No. CAC03546, Jan. 6, 2005.

Database NCBI, "*Homo sapiens* (human)," Database Accession No. CAC18884, Jan. 7, 2005.

Database NCBI, "*Homo sapiens* (human)," Database Accession No. CAC18886, Feb. 19, 2001.

Database NCBI, "*Homo sapiens* (human)," Database Accession No. NP_848561, Oct. 27, 2004.

Database NCBI, "*Homo sapiens* (human)," Database Accession No. CAC18887, Feb. 19, 2001.

Database NCBI, "*Homo sapiens* (human)," Database Accession No. NM_016583, Jun. 1, 2008.

Database NCBI, "*Homo sapiens* (human)," Database Accession No. P59827, Jun. 10, 2008.

Database NCBI, "*Homo sapiens* (human)," Database Accession No. P59826, Jun. 10, 2008.

Davies et al., "Comparative pharmacokinetics of cefamandole, cefurozxime and cephradine during total hip replacement," *J Antimicrob Chemother*, 7(5):637-640, 1986.

Dear et al., "Novel genes for potential ligand-binding proteins in subregions of the olfactory mucosa," *EMBO J.*, 10, 2813-2819, 1991.

Elsbach and Weiss, "Role of the bactericidal/permeability-increasing protein in host defence," *Curr. Opin. Immunol.*, 10:45-49, 1998.

Ganz, "Antimicrobial polypeptides," *J. Leukocyte Biology*, 74:34-38, 2004.

GenCore version 5.1.7, result 1, pp. 1-2, Feb. 24, 2006.

Ghafouri et al., "Comparative proteomics of nasal fluid in seasonal allergic rhinitis," *J. Proteome Res.*, 5:330-338, 2006.

Ghafouri et al., "Newly identified proteins in human nasal lavage fluid from non-smokers and smokers using two-dimensional gel electrophoresis and peptide mass fingerprinting," *Proteomics*, 2:112-120, 2002.

Ghafouri et al., "PLUNC in human nasal lavage fluid: multiple isoforms that bind to lipopolysaccharide," *Biochim Biophys Acta*. 1699:57-63, 2004.

Giardina et al., "Construction of acetate auxotrophs of *Neisseria meningitidis* to study host-meningococcal endotoxin interactions," *J Biol Chem*, 276:5883-5891, 2001.

Goubran Botros et al., "Biochemical characterization and surfactant properties of horse allergens," *European J. Biochemistry/FEBS*, 268(10): 3126-3136, 2001.

Huuskonen et al., "Structure and phospholipid transfer activity of human PLTP: analysis by molecular modeling and site-directed mutagenesis," *J. Lipid Res.*, 40:1123-1130, 1999.

Hwang and Vogel, "Structure-function relationships of antimicrobial peptides," *Biochem Cell Biol*, 76(2-3):235-246, 1998.

Kelley et al., "Enhanced genome annotation using structural profiles in the program 3D-PSSM," *J. Mol. Biol.*, 299:499-520, 2000.

Kleiger et al., "The 1.7 Å crystal structure of BPI: a study of how tow dissimilar amino acid sequences can adopt the same fold," *J Mol Biol*, 299:1019-1034, 2000.

LeClair et al., "Genomic organization of the mouse plunc gene and expression in the developing airways and thymus," *Biochem. Biophys. Res. Commun.*, 284:792-797, 2001.

LeClair et al., "TPL, a mouse member of the PLUNC protein family expressed in tongue epithelium," *Genomics*, 2002.

Leclair, "Four BPI (bactericidal/permeability-increasing protein)-like genes expressed in the mouse nasal, oral, airway and digestive epithelia," *Biochem. Soc. Trans.*, 31:801-805, 2003.

LeClair, "Four reasons to consider a novel class of innate immune molecules in the oral epithelium," *J. Dent. Res.*, 82:944-950, 2003.

Levy, "A neutrophil-derived anti-infective molecule: bactericidal/permeability-increasing protein," *Antimicrob. Agents Chemother.*, 44:2925-2931, 2000.

Lindahl et al., "Identification of a new potential airway irritation marker, palate lung nasal epithelial clone protein, in human nasal lavage fluid with two-dimensional electrophoresis and matrix-assisted laser desorption/ionization-time of flight," *Electrophoresis*, 22:1795-1800, 2001.

Morrison and Ulevitch, "The effects of bacterial endotoxins on host mediation systems," *Am J Pathol*, 93:527-617, 1978.

Reynolds, In: *Integrated host defense against infections*, Crystal et al. (Eds.), The Lung, 2$^{nd}$ Ed., NY, Raven Press, Ltd., 2353-2365, 1997.

Roxo-Rosa et al., "Proteomic analysis of nasal cells from cystic fibrosis patients and non-cystic fibrosis control individuals: search for novel biomarkers of cystic fibrosis lung disease," *Proteomics*, 6:2314-2325, 2006.

Sande et al., "Intermittent or continuous therapy of experimental meningitis due to *Streptococcus pneumoniae* in rabbits: preliminary observations on the postantibiotic effect in vivo," *Rev Infect Dis*, 3(1):98-109, 1981.

Scheetz et al., "Large-scale gene discovery in human airway epithelia reveals novel transcripts," *Physiol Genomics*, 17(1): 69-77, 2004.

Schumann et al., "Structure and function of the lipopolysaccharide binding protein," *Science*, 249:1429-1431, 1990.

Schutte et al., "Discovery of five conserved beta-defensin gene clusters using a computational search strategy," *Proc. Natl. Acad. Sci.*, 99:2129-2133, 2002.

Shimazu et al., "MD-2, a molecule that confers lipopolysaccharide responsiveness on Toll-like receptor 4," *J. Exp. Med.*, 189:1777-1782, 1999.

Sung et al., "Plunc, a member of the secretory gland protein family, is up-regulated in nasal respiratory epithelium after olfactory bulbectomy," *J. Biol. Chem.*, 277:12762-12769, 2002.

Tall, "Plasma lipid transfer proteins," *Annu. Rev. Biochem.*, 64:235-257, 1995.

Welsh et al., In: *The Metabolic and Molecular Basis of Inherited Disease*, Scriver et al., (Eds.), 8th Ed., NY, McGraw-Hill, Inc., 5121-5189, 2001.

Weston et al., "Differential display identification of plunc, a novel gene expressed in embryonic palate, nasal epithelium, and adult lung," *J. Biol. Chem.*, 274:13698-13703, 1999.

\* cited by examiner

- BPI and LBP had no effect on surface tension or increased surface tension.

METHODS AND COMPOSITIONS RELATED TO PLUNC SURFACTANT POLYPEPTIDES

This application claims priority to U.S. Provisional Patent application Ser. No. 60/864,062 filed Nov. 2, 2006, which is incorporated herein by reference in its entirety.

This invention was made with government support under P50 HL-61234 SCOR awarded by the National Institutes of Health. The government has certain rights in the invention.

BACKGROUND OF THE INVENTION

I. Field of the Invention

The invention is related to the fields of molecular biology, physiology, and medicine. More particularly, the invention involves compositions and methods for lowering the surface tension of a liquid-air interface with a PLUNC polypeptide or peptide fragments.

II. Background

Natural pulmonary surfactants (PS) are protein/lipid compositions that are produced naturally in the lungs and are critical to the lungs' ability to absorb oxygen. They cover the entire alveolar surface of the lungs and the terminal conducting airways leading to the alveoli. Surfactants facilitate respiration by continually modifying the surface tension of the fluid normally present within the alveoli. In the absence of sufficient surfactant, or should the surfactant degrade, the alveoli tend to collapse and the lungs do not absorb sufficient oxygen. By lowering the surface tension of the terminal conducting airways, surfactant maintains patency, i.e., keeps airways open. Loss of patency leads to obstruction of the airway and compromised pulmonary function. Human surfactants primarily contain: phospholipids, the major one being dipalmitoyl phosphatidyl-choline (DPPC), and four surfactant polypeptides, A, B, C and D with surfactant protein B (SP-B) being the most essential for respiratory function. Natural and synthetic pulmonary surfactants are commonly used to treat respiratory distress syndrome in premature infants shortly after birth.

Improved methods and compositions for achieving lower surface in pulmonary disorders, infections, and other conditions are needed.

SUMMARY OF THE INVENTION

Embodiments of the invention include the use of all or part of the PLUNC protein as a surface tension lowering (surfactant) agent. As described herein, recombinant PLUNC has surfactant or surface tension lowering properties. This protein may act to lower surface tension in a variety of biological secretions, such as but not limited to oral secretions, or at a biological or non-biological air-liquid interface (such as, but not limited to, small airways such as small bronchi or the Eustachian tube) and may prevent collapse of such structures. In other embodiments, PLUNC may be used in enhancing the spread of oral secretions, respiratory secretions, or other liquids, for example, respiratory secretions on the surface of the airways or other surfaces (including the spread of secreted mucus and antimicrobials). The surfactant properties of a PLUNC polypeptide may also enhance spreading, motility, and function of innate immune cells (e.g., neutrophils, macrophages) at the liquid-air interface. In certain aspects of the invention, a PLUNC protein, fragment, or segment thereof, can be produced recombinantly in *E. coli* or other suitable host known in the art and therefore could be used as a topical agent for respiratory, oral, and other applications. In a further aspect, a subject or patient in need of such therapy is identified. Thus, treatment is directed to a patient in need of a surfactant therapy as described below. In certain aspects, patients include those in need of ventilation or demonstrate of suspected of having a deficit in mucociliary clearance, such as primary ciliary dyskinesia (PCD), variant cystic fibrosis (CF) or pseudohypoaldosteronism (PHA). The administration of PLUNC composition The primary amino acid sequence of PLUNC is hydrophobic in nature. Secreted hydrophobic proteins are unusual in multicellular organisms. Examples of such include the pulmonary surfactant proteins B and C. The inventors observed a similarity between PLUNC amino acid sequences and an equine protein termed "latherin" (FIG. 3). Latherin is a secreted protein present in the sweat of horses that has demonstrated surfactant properties (Beeley et al., 1986). Although similarity between the PLUNC and Latherin exist, the functional properties of one member of a protein family are not indicative of the functional properties of all members of the family. The human ortholog of Latherin (termed BASE), is a pseudogene and does not express a functional protein. A recombinant human PLUNC protein was prepared to study the surfactant properties of PLUNC polypeptides (FIG. 4). PLUNC was shown to be a dose-dependent surface tension lowering agent (FIG. 6A-D), a property not shared by two related proteins from this gene family, bactericidal permeability-increasing protein (BPI) and LPS binding protein (LBP) (FIG. 6B).

The inventors have demonstrated that a PLUNC family member has surfactant properties. Furthermore, addition of a lipid component (e.g., DPPC) to PLUNC caused a further lowering of surface tension (FIG. 6C), which is similar to that reported for the pulmonary surfactant protein B. Furthermore, the addition of bovine serum albumin to a PLUNC solution inhibits its surface tension lowering properties, a feature shared by the therapeutic pulmonary surfactant Infasurf™ (FIG. 6D). The discovery of surface tension lowering properties of PLUNC polypeptides is novel and unexpected. These properties are indicative of PLUNC's therapeutic applications exploiting the surface tension lowering properties. The surfactant activity of the protein can be used in enhancing the spread of antimicrobial proteins and concentrate them at interfaces where there activities are needed, such as the airway surface.

As used herein, "surfactant activity" refers to the ability of a substance, such as an organic molecule, protein or polypeptide, either alone or in combination with other molecules, to lower surface tension at an air/water interface. The measurement can be made with a Wilhelmy Balance or pulsating bubble surfactometer by an in vitro assay. See, for example King et al., 1972, or Enhorning, 1977, each of which is incorporated herein by reference in its entirety. Briefly, the Enhorning Surfactometer (Surfactometer International, Toronto, Ontario) measures the pressure gradient (ΔP) across a liquid-air interface of a bubble that pulsates at a rate of 20 cycles/min between a maximal (0.55 mm) and minimal (0.4 mm) radius. The bubble, formed in a 37° C., water-enclosed, 20-μl sample chamber, is monitored through a microscopic optic while the pressure changes are recorded on a strip chart recorder calibrated for 0 and −2 cm $H_2O$. In addition, in vivo measurements of increases of compliance or airflow at a given pressure of air entering the lung can be readily made, such as in the assay of Robertson, 1980, incorporated herein by reference in its entirety. In this assay, the sample to be assessed is administered through an endotracheal tube to fetal rabbits or lambs delivered prematurely by Caesarian section. (These "preemies" lack their own pulmonary surfactant (PS), and are supported on a ventilator.) Measurements of lung compliance, blood gases, and ventilator pressure provide indices of activity. In vitro assays of surfactant activity, which is assessed as the ability to lower the surface tension of a pulsating bubble, and in vivo assays utilizing fetal rabbits is described in detail by Revak et al., 1986.

In certain aspects, a surfactant of the present invention comprises a PLUNC peptide that can be isolated from recombinant sources or synthesized. Exemplary peptides for use herein include naturally and non-naturally occurring PLUNC peptides, such as, for example, one or a combination of animal-derived PLUNC polypeptides; recombinant PLUNC polypeptides; synthetically derived PLUNC polypeptides; PLUNC analogs; PLUNC polypeptide mimics; conservatively modified variants thereof retaining activity; and fragments thereof retaining activity. A surfactant polypeptide mimic is generally a polypeptide that is engineered to mimic the surfactant attributes of human PLUNC protein. In certain embodiments, the surfactant polypeptide comprises a PLUNC peptide that comprises or consists of at least about 10, at least 11 amino acid residues, and no more than about 130, more usually fewer than about 125 and/or fewer than about 100 amino acid residues of a PLUNC polypeptide.

Certain embodiments involve methods of lowering surface tension at a liquid-air interface comprising administering an amount of an isolated PLUNC polypeptide sufficient to lower the surface tension at the liquid-air interface. In certain aspects, the PLUNC polypeptide is an amino terminal fragment of a PLUNC protein. In a further aspect, the PLUNC polypeptide is a amino terminal fragment having an amino acid sequence of 10, 20, 30, 40, 50 to 40, 50, 60, 70, 80, 90, 100, 120 to 250 amino acids, including all values and ranges there between of SEQ ID NO:2, SEQ ID NO:4, SEQ ID NO:6, SEQ ID:8, SEQ ID NO:10, SEQ ID NO:12 and/or SEQ ID NO:14. In still further aspects, the amino terminal fragment has an amino acid sequence derived from SEQ ID NO:2, SEQ ID NO:4, SEQ ID NO:6, SEQ ID:8, SEQ ID NO:10, SEQ ID NO:12 and/or SEQ ID NO:14. In certain aspects, the PLUNC polypeptide is administered to a subject at a dose of 1, 10, 50, 100 µg or mg to 50, 100, 200, or 500 µg or mg per kg of body weight.

Certain embodiments of the invention include compositions comprising 5, 10, 20, 30, 40, 50, 60, 70, 80, 90, 100 µg, ng, or mg of one or more lipid and/or phospholipid and 5, 10, 20, 30, 40, 50, 60, 70, 80, 90, 100 µg, ng, or mg proteins including one or more PLUNC polypeptide or peptide fragment in 1 to 100 µl or ml of volume. In certain methods of the present invention, a surfactant composition comprises one or more lipids. In these embodiments, the surfactant composition can comprise, for example, from as little as about 0.05 to 100% weight percent lipid, so long as the resulting composition has surfactant activity. By weight percent is meant the percentage of a compound by weight in a composition by weight. Thus, a composition having 50 weight percent lipid contains, for example, 50 grams lipid(s) per 100 grams total composition. The term "lipid" as used herein refers to a naturally occurring, synthetic or semi-synthetic (i.e., modified natural) compound which is generally amphipathic. The lipids typically comprise a hydrophilic component and a hydrophobic component. Exemplary lipids include, but are not limited to, phospholipids, fatty acids, fatty alcohols, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion. Preferably, the lipids of are fatty acids, alcohols, esters and ethers thereof, fatty amines, or combinations thereof.

Examples of phospholipids include native and/or synthetic phospholipids. Phospholipids that can be used include, but are not limited to, phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols include, but are not limited to, sterols, palmitic acid, cetyl alcohol, lauric acid, myristic acid, stearic acid, phytanic acid, dipamlitic acid, and the like. Preferably, the fatty acid is palmitic acid and preferably the fatty alcohol is cetyl alcohol.

Examples of fatty acid esters include, but are not limited to, methyl palmitate, ethyl palmitate, isopropyl palmitate, cholesteryl palmitate, palmityl palmitate sodium palmitate, potassium palmitate, tripalmitin, and the like.

An example of a semi-synthetic or modified natural lipid is any one of the lipids described above which has been chemically modified. The chemical modification can include a number of modifications; however, a preferred modification is the conjugation of one or more polyethylene glycol (PEG) groups to desired portions of the lipid.

In certain aspects, the liquid-air interface is part of the respiratory system or auditory system of a subject. In particular, the liquid-air interface is present in a subject's upper respiratory system, trachea, mouth, lungs, or Eustachian tubes. Administration may be by endotracheal administration, inhalation, or other administrative route that directly or indirectly can be in contact with the compositions of the invention. The methods may further comprise a second therapy. The second therapy can be a respiratory therapy, such as conventional ventilation, high frequency ventilation, or continuous positive airway pressure. The second therapy may also include administration of one or more therapeutic agents, such as nitric oxide, steroids, antioxidants, vitamins, vitamin derivatives, reactive oxygen scavengers, bronchodilators, diuretics, antimicrobial agents, anti-infective agents, antihypertensive agents and/or anti-inflammatory agents. The methods may also include administering a pulmonary surfactant other than the PLUNC polypeptide, such as Poractant Alfa, Beractant, Bovactant, Colfosceril Palmitate, Surfactant-Ta, Calfactant, Pumactant, Lusupultide or Sinapultide. The second therapy may also be an antibiotic therapy, such as penicillin, ampicillin, amoxycillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, and/or ethambutol.

Further embodiments may involve methods of enhancing effectiveness of anti-microbial agents comprising administering a PLUNC polypeptide having an amino acid sequence of SEQ ID NO:2, SEQ ID NO:4, SEQ ID NO:6, SEQ ID:8, SEQ ID NO:10, SEQ ID NO: 12 or SEQ ID NO:14, including 10 to 250 amino acids of the amino terminus, and an anti-microbial, wherein the PLUNC polypeptide lowers the surface tension of a liquid-air interface and enhances dispersion of the anti-microbial.

Still further embodiments involve methods of enhancing effectiveness of a surfactant comprising administering a PLUNC polypeptide and a surfactant, wherein the PLUNC polypeptide lowers the surface tension of a liquid-air interface produced by the surfactant alone.

Embodiments of the invention also involve surfactant compositions comprising a PLUNC surfactant and a second surfactant. The second surfactant may be one or more lipid, such as phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C 16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, egg phosphatidylcholine (EPC) or combinations thereof. In a particular aspect the lipid is DPPC.

The terms "inhibiting," "reducing," or "lowering," or any variation of these terms, when used in the claims and/or the specification includes any measurable decrease to achieve a desired result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In one example, "about" will mean a 50% variance from the value stated.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 6A) Infasurf is a positive control. (FIG. 6B) BPI and LBP had no effect on surface tension or increased surface tension. (FIG. 6C) Mixing PLUNC (hSP1) with DPPC (the primary phospholipid in pulmonary surfactant) results in a further 5-10 mN/m lowering of surface tension compared to PLUNC-1 alone. (FIG. 6D) Serum albumin, known to inhibit the surface tension lowering activity of SP-B in pulmonary surfactant, affects PLUNC preparations only at relative concentrations greater than 500:1.

In FIG. 12C, spreading behavior over time is compared for Tris buffer and a PLUNC-containing solution dispensed onto a hydrophobic surface. On each coverslip, the drop on the left is buffer, while drops of PLUNC (140 µg/mL) are shown on the right. Drop spreading was photographed after (i) 5 minutes, (ii) 25 minutes, and (iii) 45 minutes, revealing that the presence of PLUNC conferred an increased tendency for an aqueous solution to spread on a hydrophobic surface.

DETAILED DESCRIPTION OF THE INVENTION

I. PLUNC Polypeptides

Figure 1:
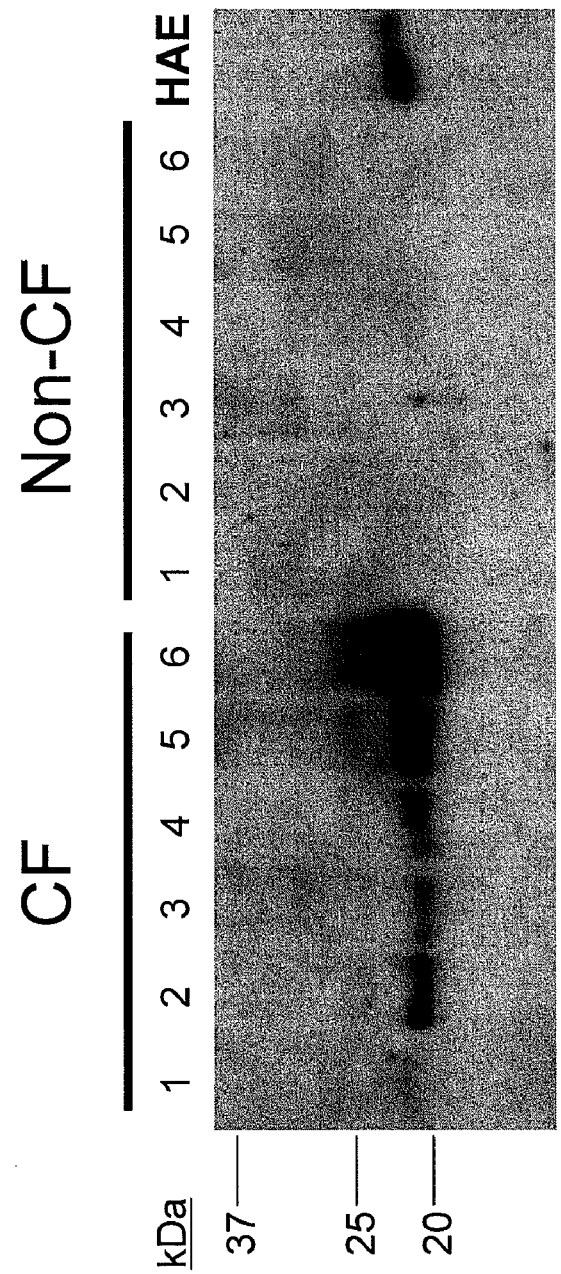
FIG. 1. Illustrates PLUNC protein in bronchoalveolar lavage fluid. BAL samples from six cystic fibrosis (CF) and six non-CF subjects were western blotted for PLUNC, illustrating elevated PLUNC levels in the lungs of CF patients. Apical wash (25 µL) from a primary culture of human airway epithelia (HAE) was included as a positive control for the antibody.

The upper respiratory tract and oropharynx, including the nasal and oral cavities, are the major route of entry of pathogens into the body and early recognition of bacterial products in this region is critical for host defense. Proteins that are central to bacterial product recognition and response include members of the lipid transfer/lipopolysaccharide binding protein (LT/LBP) family. Well characterized members of this family include BPI, LBP, CETP and PLTP. In addition to these proteins, Bingle and Craven (2002) have described a family of 7 candidate host defense proteins in humans, which are designated PLUNC for palate, lung, and nasal epithelium clone.

The surfaces of the conducting airways and alveoli of the lung comprise a large interface between the host and the environment. Despite an ongoing daily exposure to microbes and their components by inhalation, the intrapulmonary airways and airspaces normally maintain a sterile state without significant inflammation (Reynolds, 1997). However, in disease states such as, but not limited to, cystic fibrosis and chronic obstructive pulmonary disease, the lung is characterized by marked neutrophilic infiltrates and inflammation (Welsh et al., 2001). This successful maintenance of the normal condition reflects the success of the concerted activities of the innate and adaptive immune systems.

Members of the LT/LBP family may contribute to airway innate defense through their anti-inflammatory or antibacterial actions. For example, sensitive cellular responses to many bacterial endotoxins require the concerted action of at least four host extracellular and cellular proteins—lipopolysaccharide binding protein (LBP), CD14, MD-2 and TLR4 (Shimazu et al., 1999). Bactericidal/permeability-increasing protein (BPI), selectively exerts multiple anti-infective actions against Gram-negative bacteria, including cytotoxicity through damage to bacterial membranes, neutralization of bacterial endotoxin (lipopolysaccharide, LPS), and also serves as an opsonin for phagocytosis of Gram-negative bacteria by neutrophils (Elsbach and Weiss, 1998). Other members of the large LT/LBP family include lipopolysaccharide binding protein (LBP) (Schumann et al., 1990), cholesteryl ester transfer protein (CETP) and phospholipid transfer protein (PLTP) (Tall, 1995). LBP forms a complex with LPS and in conjunction with CD14 activates TLR4 to initiate innate immune responses. Plasma CETP facilitates the transfer of cholesteryl ester from HDL to apolipoprotein B-containing lipoproteins (Bruce et al., 1998). PLTP transfers phospholipids from triglyceride-rich lipoproteins to HDL during lipolysis (Tall, 1995). Although these 4 proteins possess different physiological functions, they share marked biochemical similarities. With the exception of CETP, these genes are part of a large ~300 kb cluster on chromosome 20q11.2 (Bingle and Craven, 2002). Interestingly, the gene cluster is adjacent to one of the β-defensin clusters (Schutte et al., 2002).

Weston et al. (1999) discovered the mouse Plunc gene by using differential display to identify a gene transcript that was expressed in the presumptive nasal epithelium of the mouse embryo. In situ hybridization analysis showed discrete regions of expression associated with the palate, nasal septum, nasal conchae, adult trachea, and bronchi of the lung and designated the gene Plunc.

Bingle and Bingle (2000) reported the cloning and characterization of the human ortholog of Plunc. This protein has also previously been termed "LUNX". They demonstrated by RNA blot analysis that expression of human PLUNC (SPLUNC1) was restricted to the trachea, upper airway, nasopharyngeal epithelium, and salivary gland. The human SPLUNC1 gene is comprised of 9 exons and covers 7.3 kb; the first and last exons are noncoding. The cDNA encodes a leucine-rich protein of 256 amino acids which is 72% identical to the murine protein.

The expression of murine Plunc and Lplunc1 demonstrate an overlapping pattern in oral, lingual and tracheal and bronchial epithelia (LeClair, et al., 2002). Of the known mouse LT/LBP family members, Plunc and Lplunc1 appear to be the major expressed genes in the respiratory epithelia (Weston et al., 1999; Leclair, 2003). Similarly, the expression of human PLUNC and LPLUNC1 transcripts is abundant in the respiratory tract as described herein and in Bingle and Craven (2002). Furthermore, the presence of PLUNC protein in human and mouse respiratory secretions was recently independently reported by two groups, and there is evidence that protein levels increase with exposure to irritants, inflammation or trauma (Lindahl et al., 2001; Ghafouri et al., 2002; Sung et al., 2002). Despite evidence of abundant expression at the mRNA and protein levels, no studies have been performed to elucidate the functions of PLUNC or LPLUNC1.

Recent evidence indicates a much larger family of putative lipid binding proteins resides at 20q11.2. In addition to human PLUNC, several other related sequences termed either "short" PLUNCs (SPLUNCs) or "long" PLUNCs (LPLUNCs) were identified (Bingle and Craven, 2002). There are at least 8 human PLUNC related sequences and a syntenic ~400 kb locus on mouse chromosome 2. Study of the mouse genome sequence reveals at least 11 LT/LBP family members in a syntenic locus on chromosome 2, spanning ~400 kb (LeClair et al., 2001; LeClair et al., 2002). In further support of a shared ancestry of the LT/LBP family is the finding that the genes exist as a cluster and share similar genomic structures (Bingle and Craven, 2002). The intron and exon organization of the short and long PLUNCs also suggests conserved functions. The short PLUNCs typically have 9 exons, while long PLUNCs (including BPI, LBP, CETP and PLTP) have 16 exons.

The identification of PLUNC-related proteins arose from an iterative combination of analysis of the published sequence of chromosome 20 coupled with BLAST searches against the GenBank databases, using as the starting point the sequence of PLUNC (Bingle and Bingle, 2000). This procedure identified that PLUNC (which may also be designated SPLUNC1) is a member of a family of seven proteins that are encoded by adjacent genes in an approximately 300 kb region of chromosome 20q11. Members of the PLUNC family fall into two groups based on their size. One group, which the inventors designate as 'short' proteins, comprises PLUNC (SPLUNC1) (GI #7958616, 256 amino acids), SPLUNC2 (GI #9801234, 249 amino acids) and SPLUNC3 (GI #109627654, 254 amino acids). The other group, designated as 'long' proteins, comprises LPLUNC1 (GI #19880274, 484 amino acids, also known as von Ebner minor salivary gland protein), LPLUNC2 (GI #11877274, 458 amino acids), LPLUNC3 (GI #73620973, 476 amino acids) and LPLUNC4 (GI #34395623, 575 amino acids). All of these proteins, with the exception of LPLUNC4 contain putative signal peptides at the N terminus. All of these proteins and segments thereof will be generally designated as PLUNC. Within the PLUNC family, the sequence identity is rather low, ranging typically from 16% to 28%, with LPLUNC3 and LPLUNC4 sharing a somewhat higher pairwise identity of 37%. Rat orthologs of LPLUNC3 and LPLUNC4 have previously been reported (Dear et al., 1991). A weak sequence similarity was noted between these two orthologs, RYA3 and RY2G5, and BPI and LBP.

BPI is the only member of this family for which the structure has been solved (Beamer et al., 1997). BPI has a "boomerang" shape with two structurally similar domains of approximately 200 residues. It has been proposed that the two domains of BPI and related proteins are functionally and covalently linked pseudodimer that may have evolved by gene duplication from a monomeric ancestral protein (Beamer et al., 1998; Beamer et al., 1999). In support of this, PLUNC (256 residues) and the other SPLUNCs bear similarities to the N-terminal domain of BPI (Bingle and Craven, 2002). Importantly, each SPLUNC shares a single conserved disulfide bond that appears analogous to the single disulfide in the N-terminal half of BPI. Thus, the short PLUNCs may be structurally similar to the N-terminal half of BPI and related LPLUNCs. The inventors used the BPI crystal structure to model LPLUNC1 (484 residues) and found that it shares features similar to BPI (456 residues).

The putative familial relationship and a fold or structural similarity of PLUNC to BPI was found using the 3DPSSM fold recognition service (Kelley et al., 2000), which predicted a fold similar to that of BPI at the 95% confidence level for all seven members of the PLUNC family. 3DPSSM is a threading method that uses not only primary sequence comparison, but also predicted secondary structure and polarity/hydrophobicity to detect similarities to proteins of known 3D structure. The prediction of structural similarity to BPI was much more significant than matches to any other of over 6000 structures scanned by 3DPSSM.

The two-domain structure of the BPI fold accounts for the division of the PLUNC family into short and long proteins, these groups containing either one or both of the BPI domains, respectively. For the short sequences, the most confident match made by 3DPSSM was to the N-terminal domain of BPI. All three short proteins contain cysteine pairs, consistent with the location of the disulfide bond present in the N-terminal domain of BPI. In SPLUNC1 and SPLUNC2, the position of the residue putatively equivalent to Cys 175 of BPI aligns with a position eight residues later. This corresponds to being positioned two turns later in the helix, but probably simply reflects the uncertainty in the register of the alignment of this long helical segment and small changes in the relative positioning of the helical and sheet segments.

3DPSSM indicates a clear relationship between the BPI and PLUNC families, it also indicates a fundamental structural difference between them. The BPI family is predicted to share a very closely similar secondary structure throughout both domains, a finding consistent with previous studies (Beamer et al., 1997, Bruce et al., 1998, Huuskinen et al., 1999). In the LPLUNC proteins, the C-terminal domain similarly appears to share the same secondary structure as BPI. In contrast, in the N-domain of the LPLUNC proteins and in the SPLUNC proteins, there is a much greater variability. Much of the variability is in the region that forms one of the tips of the rather elongated molecule. This region, which includes the β-hairpins containing residues 45 and 96, is particularly important for the bactericidal activity of BPI and is also the region of greatest structural difference between the two domains of BPI itself (Levy, 2000). It is the N-terminal domain of BPI that appears to mediate most of the LPS-binding and antibiotic effects of the protein. In fact it has been shown that the N-terminal domain of BPI alone exerts identical biological effects to the full-length protein. The exception to this is the opsonic role of BPI, which is mediated by the C-terminal domain (Levy, 2000).

II. Proteinaceous Compositions

Figure 2:
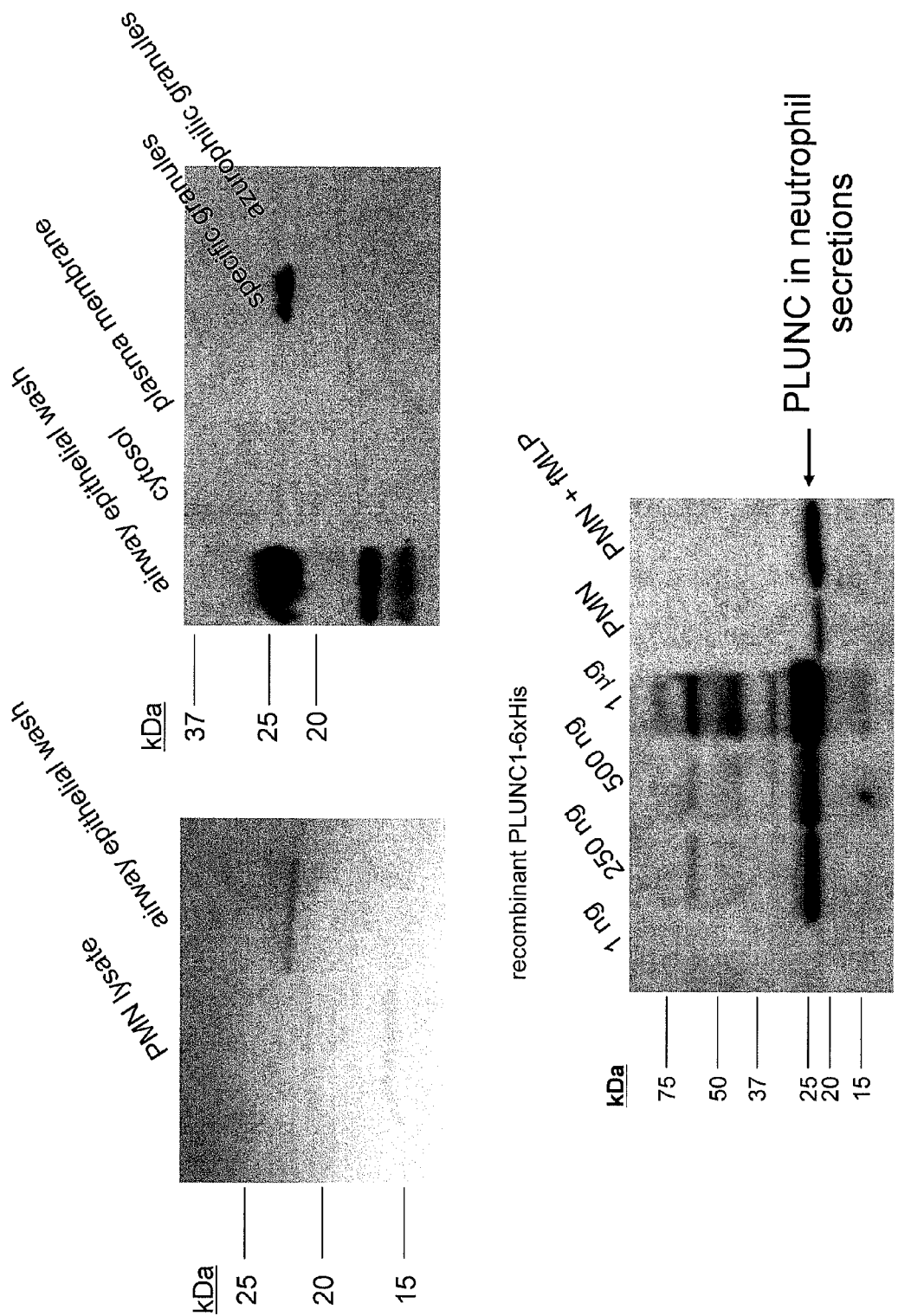
FIG. 2. Illustrates PLUNC is a secretory product of neutrophil secondary ("specific") granules.
Figure 7:
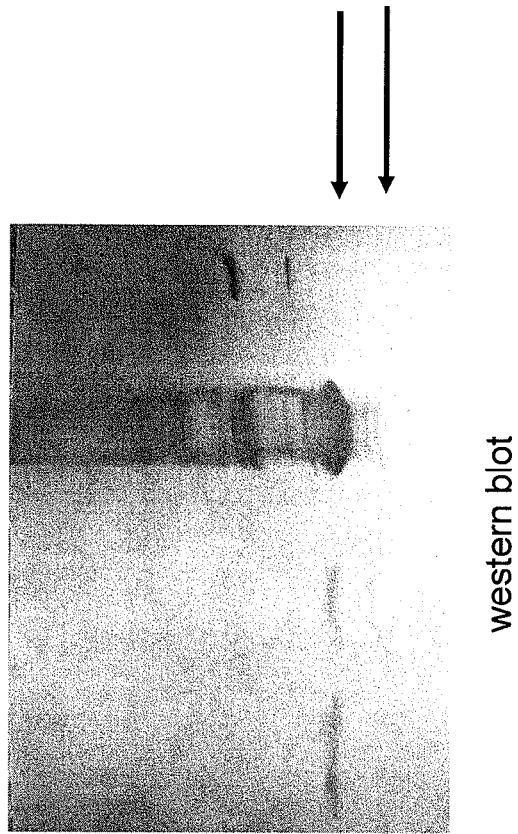
FIG. 7. Illustrates two forms of PLUNC protein are detectable in middle ear aspirates.
Figure 8:
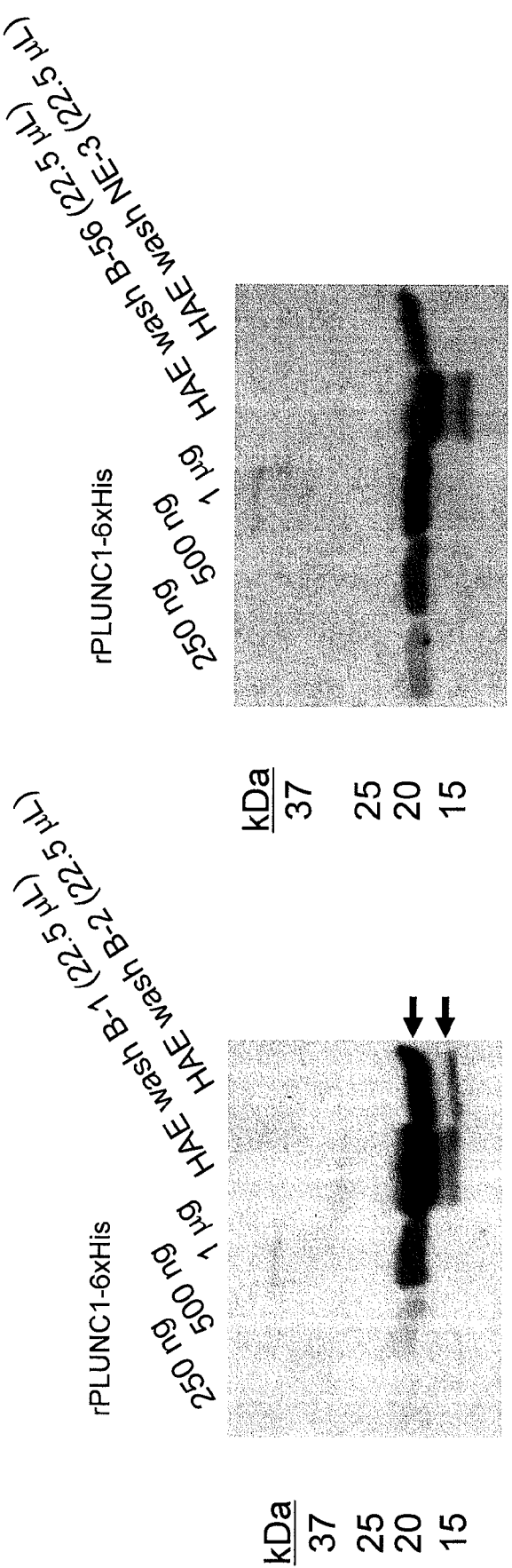
FIG. 8. Illustrates two forms of PLUNC protein are detectable in airway secretions.
Figure 9:
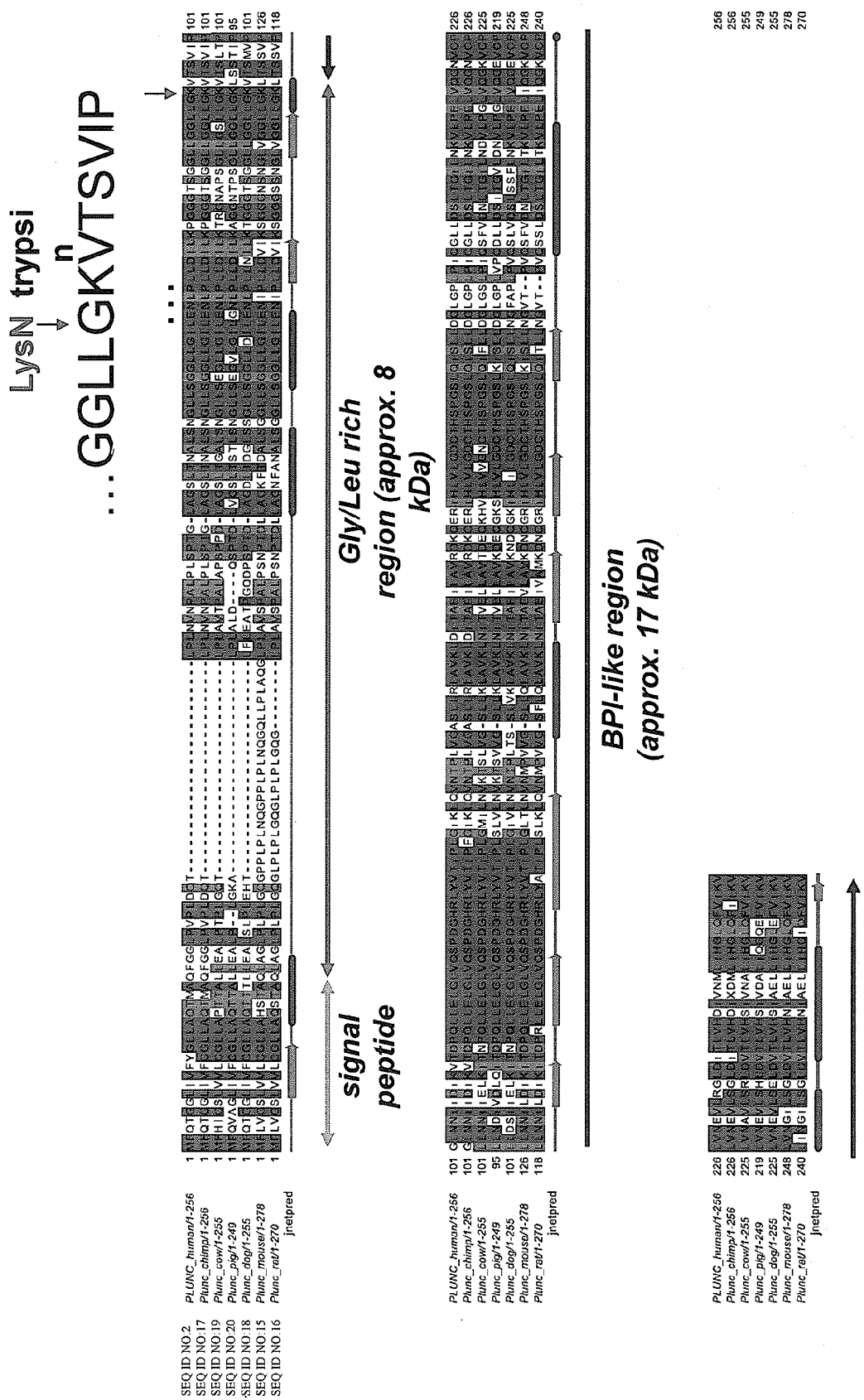
FIG. 9. Illustrates a site for enzymatic cleavage of PLUNC by trypsin.
Figure 10:
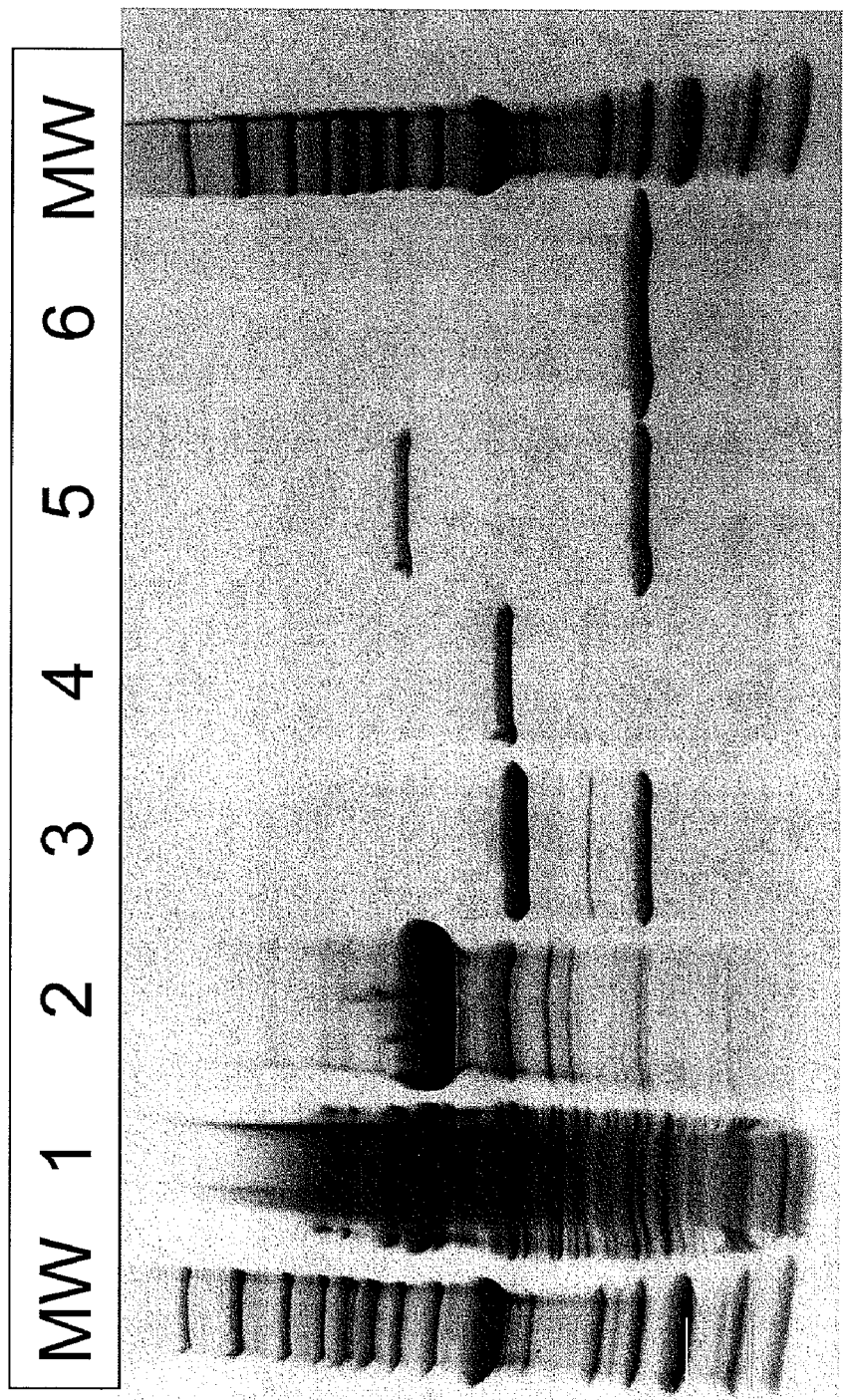
FIG. 10. Shows a coomassie stained SDS-PAGE gel demonstrating expression and purification of recombinant human PLUNC. Recombinant PLUNC protein, possessing an N-terminal maltose-binding protein (MBP) tag and a C-terminal 6×His tag, was expressed in *E. coli*. After centrifugation, the crude bacterial lysate (Lane 1) was passed over amylose resin and bound fusion protein was eluted from the resin using maltose. The recovered elution fraction (Lane 2) indicated a predominant product of approximately 69 kDa, consistent with the predicted size of the MBP-PLUNC-6×His fusion protein. Fusion protein was further purified by gel filtration, followed by a 16 hour cleavage with Factor Xa protease to remove the MBP tag. Factor Xa treatment gave rise to two cleavage products, MBP at 43 kDa and PLUNC-6×His at approximately 26 kDa (Lane 3). After passing the cleavage products over nickel resin, MBP was observed in the flowthrough fraction (Lane 4), while the elution fractions contained PLUNC-6×His and any remaining uncleaved His-tagged fusion protein (Lane 5). A final gel filtration step was used to separate PLUNC-6×His from the uncleaved protein (Lane 6). MW=molecular weight ladder (BenchMark Unstained Protein Standard; BioRad).
Figure 11:
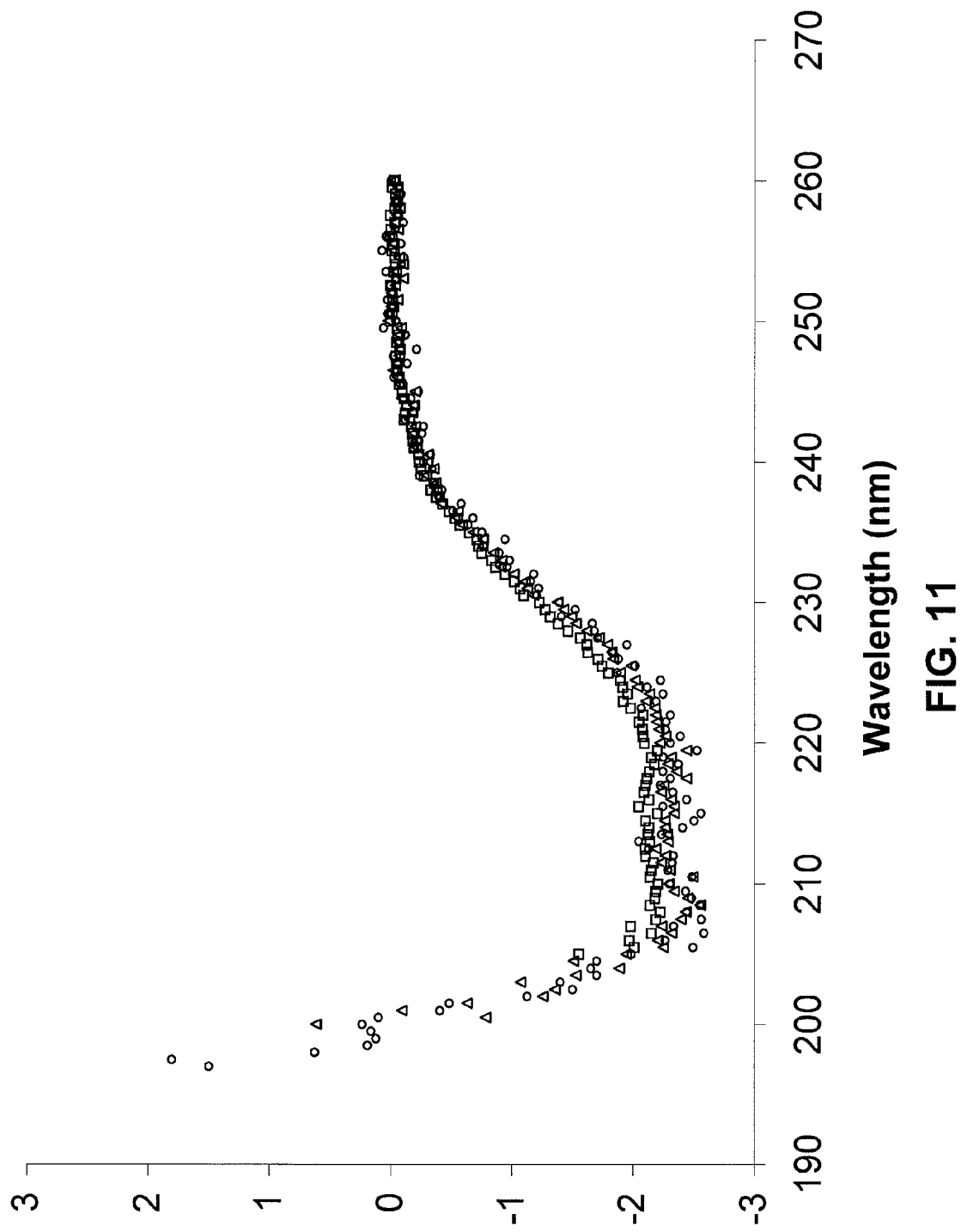
FIG. 11. Shows a circular dichroism spectra of recombinant human PLUNC. Molar ellipticities in the far-UV range (197-260 nm) are plotted for PLUNC at 0.54 mg/mL, 1.08 mg/mL, and 2.16 mg/mL. Analysis of this data using the K2d server predicts that the secondary structure of PLUNC is 24-33% alpha-helical, ~15% beta-sheet, and 51-61% random.

Proteinaceous compositions of the invention will typically include all or part of a PLUNC polypeptide. In certain aspects, the proteinaceous composition will comprise a polypeptide having an amino acid sequence similar to first 100 or so N-terminal amino acids of a PLUNC polypeptide. PLUNC has structural properties suggesting it may be a bi-functional secreted protein. Western blots of PLUNC protein in secretions from airway epithelia (FIG. 8), neutrophils (FIG. 2), and middle ear aspirates (FIG. 7), demonstrate two immunoreactive forms of the protein. One of ~25 kD in size consistent with the full length protein, and a second lower molecular weight form of ~17 kD suggests a C-terminal fragment. End sequencing of the 17 kD fragment and confirmed that it represents a C-terminal cleavage product of the full length secreted protein (FIG. 9). As shown in FIG. 9, cleavage between G and K residues in the protein releases an N-terminal hydrophobic peptide and the C-terminal fragment that contains the region of the protein that is most similar to the neutrophil product BPI, a protein known to bind endotoxin and exhibit antimicrobial activities (FIG. 10). The inventors contend that PLUNC is a novel bi-functional protein with surfactant properties residing in the N-terminal portion of the molecule (FIG. 11).

Proteinaceous compositions of the invention may include surface tension lowering polypeptides or peptides including or derived from PLUNC polypeptides.

The present invention relates generally to proteins useful for lowering surface tension. In certain embodiments, the present invention concerns novel compositions comprising all or part of a polypeptide of the PLUNC family, in particular polypeptides having all or portions of a sequence as set forth in SEQ ID NO:2, SEQ ID NO:4, SEQ ID NO:6, SEQ ID NO:8, SEQ ID NO:10, SEQ ID NO:12 or SEQ ID NO:14. As used herein, a "proteinaceous molecule," "proteinaceous composition," "proteinaceous compound," "proteinaceous chain" or "proteinaceous material" generally refers, but is not limited to, a protein of greater than about 80 amino acids or the full length protein; a polypeptide of greater than about 100 amino acids; and/or a peptide of from about 5 to about 120 amino acids. In certain aspects the polypeptides of the invention include at least or at most 25, 50, 75, 100, 125, 150, 175, 200 or 225 amino acids, including all values and ranges there between, of the N-terminus of a PLUNC polypeptide (e.g., SEQ ID NO:2, SEQ ID NO:4, SEQ ID NO:6, SEQ ID NO:8, SEQ ID NO:10, SEQ ID NO:12 or SEQ ID NO:14) or a sequence that is at least 50, 60, 70, 80, 90, 95, 99, or 100% identical to such an amino acid sequences, including all percentages there between to SEQ ID NO:2, SEQ ID NO:4, SEQ ID NO:6, SEQ ID NO:8, SEQ ID NO:10, SEQ ID NO:12 or SEQ ID NO:14. All the "proteinaceous" terms described above may be used interchangeably herein.

In certain embodiments the size of the at least one proteinaceous molecule may comprise, but is not limited to at most or at least about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, or greater amino acid molecule residues, and any range derivable therein.

As used herein, an "amino acid molecule" refers to any amino acid, amino acid derivative or amino acid mimetic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moiety. In certain embodiments, the sequence of residues of the proteinaceous molecule may be interrupted by one or more non-amino molecule moiety. Accordingly, the term "proteinaceous composition" encompasses amino molecule sequences comprising at least one of the 20 common amino acids in naturally synthesized proteins, or at least one modified or unusual amino acid.

In certain embodiments, the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, administered to, or given an organism according to the methods and amounts described herein or readily determinable by a professional. Such untoward or undesirable effects include those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and amino acid sequences for various genes of the PLUNC family have been previously disclosed, and may be found at computerized databases known to those of ordinary skill in the art. One such database is the National Center for Biotechnology Information's Genbank and GenPept databases (www.ncbi.nlm.nih.gov/). The coding regions for these known genes may be amplified and/or expressed using the techniques disclosed herein or as would be know to those of skill in the art, see Sambrook et al. (2001) for exemplary methods.

Variant polypeptides or peptides may be designed with enhanced antimicrobial and/or immune modulatory properties, i.e., amino acid substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. Since it is the interactive capacity and nature of a protein that defines that protein's biological activity, certain amino acid substitutions can be made in a protein sequence, and its underlying DNA coding sequence which potentially create a peptide with superior characteristics.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. It is known in the art that certain amino acids may be substituted by other amino acids having a similar hydropathic index or score and still result in a protein with similar biological activity, i.e., still obtain a biological functionally equivalent protein.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is notable that the PLUNC predicted amino acid sequences contain remarkably hydrophobic segments.

Amino acid substitutions are generally based on the relative similarity of the amino acid side-chain substituents, for example, their hydrophobicity, hydrophilicity, charge, size, and the like but may nevertheless be made to highlight a particular property of the peptide, for example surfactant properties. Exemplary substitutions that take various of the foregoing characteristics into consideration are well known to those of skill in the art and include the substitution of: arginine and lysine; glutamate and aspartate; serine and threonine; glutamine and asparagine; and valine, leucine and isoleucine.

A. Protein Purification

Polypeptide and peptide purification techniques are well known to those of skill in the art. These techniques involve, at one level, the crude fractionation of the milieu to polypeptide and non-polypeptide fractions. Source materials may include bacteria, insect cells, eukaryotic cells or mammalian cells expressing a polypeptide to be purified. In certain aspects, the cell may be an insect cell infected with a baculovirus expression vector. Having separated the polypeptide from other proteins, the polypeptide of interest may be further purified using chromatographic, immunologic, and/or electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is fast protein liquid chromatography or HPLC.

Certain aspects of the present invention concern the purification, and in particular embodiments, the substantial purification, of an encoded polypeptide. The term "purified polypeptide" as used herein, is intended to refer to a composition, isolatable from other components, wherein the polypeptide is purified to any degree relative to its naturally-obtainable state. A purified polypeptide therefore also refers to a polypeptide, free from the environment in which it may naturally occur.

Generally, "purified" will refer to a polypeptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more peptides in the composition. The term "purified to homogeneity" is used to mean that the composition has been purified such that there is single protein species based on the particular test of purity employed for example SDS-PAGE or HPLC.

Various methods for quantifying the degree of purification of the peptide will be known to those of skill in the art in light of the present disclosure. These include, for example, assessing the amount of polypeptide within a fraction by SDS/PAGE analysis.

There is no general requirement that the polypeptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below. For exemplary methods see Current Protocols in Protein Science, 2003, which is incorporated herein by reference.

In particular embodiments Hexa (6×)-His (6His) tagged proteins may be purified using nickel affinity chromatography alone or in conjunction with other purification methods described herein or in the art (Sambrook et al., 2001).

B. Fusion Proteins

The polypeptides of the instant application may be combined with fusion partners to produce fusion proteins. It is envisioned that such constructs might include combinations of a surfactant polypeptide with a partner also exhibiting some level of surfactant or complementary activity. Such a construct generally has all or a substantial portion of the native molecule or functional segment thereof, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification if such removal is desired. Other useful fusions include linking of functional domains, such as active sites from enzymes, glycosylation domains, cellular targeting signals or transmembrane regions.

As used in this application, the term "an isolated nucleic acid encoding a polypeptide surfactant" refers to a nucleic acid molecule that has been isolated free of total cellular nucleic acid. The term "functionally equivalent codon" is used herein to refer to codons that encode the same amino acid, such as the six codons for arginine or serine (Table 1, below), and also refers to codons that encode biologically equivalent amino acids, as discussed herein.

Allowing for the degeneracy of the genetic code, sequences that have at least about 50%, usually at least about 60%, more usually about 70%, most usually about 80%, or at least about 90% or about 95% of nucleotides that are identical to the nucleotides of a gene encoding an antimicrobial polypeptide of the PLUNC family or variant thereof will be sequences that are encompassed by the present invention. Nucleic acid sequences of the present invention may also be functionally defined as sequences that are capable of hybridizing to a nucleic acid segment encoding an antimicrobial polypeptide of the PLUNC family or variant thereof.

The DNA segments of the present invention include those encoding biologically functional equivalent surfactant polypeptides or peptides, as described above. Functionally equivalent proteins or peptides may be created via the application of recombinant DNA technology, in which changes in the protein structure may be engineered, based on considerations of the properties of the amino acids being exchanged, or as a result of natural selection. Changes designed by man may be introduced through the application of site-directed mutagenesis techniques or may be introduced randomly and screened later for the desired function.

TABLE 1

| Amino Acids | Three letter | One letter | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

C. Peptide Synthesis

The polypeptides and/or peptides of the invention may be chemically synthesized. An example of a method for chemical synthesis of such a polypeptide or peptide is as follows. Using the solid phase peptide synthesis method of Sheppard et al. (1981) an automated peptide synthesizer (Pharmacia LKB Biotechnology Co., LKB Biotynk 4170) adds N,N'-dicyclohexylcarbodiimide to amino acids whose amine functional groups are protected by 9-fluorenylmethoxycarbonyl groups, producing anhydrides of the desired amino acid (Fmoc-amino acids). An Fmoc amino acid corresponding to the C-terminal amino acid of the desired peptide is affixed to Ultrosyn A resin (Pharmacia LKB Biotechnology Co.) through its carboxyl group, using dimethylaminopyridine as a catalyst. The resin is then washed with dimethylformamide containing piperidine resulting in the removal of the protective amine group of the C-terminal amino acid. A Fmoc-amino acid anhydride corresponding to the next residue in the peptide sequence is then added to the substrate and allowed to couple with the unprotected amino acid affixed to the resin. The protective amine group is subsequently removed from the second amino acid and the above process is repeated with additional residues added to the peptide in a like manner until the sequence is completed. After the peptide is completed, the protective groups, other than the acetoamidomethyl group are removed and the peptide is released from the resin with a solvent consisting of, for example, 94% (by weight) trifluoroacetic acid, 5% phenol, and 1% ethaniol. The synthesized peptide is subsequently purified using high-performance liquid chromatography or other peptide purification technique know to one of ordinary skill in the art.

III. Therapeutic Uses of Surfactant Peptides

This invention includes, but is not limited to, methods to lower the surface tension of a target liquid-air interface. The surfactant properties of the polypeptides disclosed allow them to be included in formulations to lower surface tension and increase dispersion of a liquid over a surface, and any adverse physiological responses. The purified polypeptide may be used without further modifications or it may be diluted in a pharmaceutically acceptable carrier. It is contemplated that the invention may be administered to humans or animals, included in pharmaceutical preparations, medicinal and pharmaceutical products, cosmetic products, hygienic products, cleaning products and cleaning agents, as well as any material to which the polypeptides could be sprayed on or adhered to wherein the lowering of surface tension or surfactant effects on such a material is desired.

The proper dosage of a PLUNC polypeptide to effect the lowering of surface tension and results there from depends upon a number of factors including the types and location of the target surface, the environment into which the polypeptide is being introduced, and the time that the polypeptide is envisioned to remain in a given area.

A. Pharmaceutical Therapy

It is further contemplated that the surfactant polypeptides of the invention may be used in combination with or to enhance the activity of other surfactants or pharmaceuticals. Combinations of the polypeptide with other agents may be useful to allow surfactants and/or antibiotics to be used at lower doses, to enhance the activity of agent, or to effectuate a synergism between the components such that the combination is more effective than the sum of the efficacy of either component independently. Antibiotics which may be used in combination therapy include, but are not limited to penicillin, ampicillin, amoxycillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, and ethambutol.

Contacting a surface in vivo may be achieved by administering to an animal (including a human patient) that has, or is suspected to have a need for surfactant or antimicrobial therapy, a therapeutically effective amount of pharmacologically acceptable polypeptide or peptide formulation of the invention alone, or in combination with a therapeutic amount of a pharmacologically acceptable formulation of an additional agent. The methods and compositions of the invention may be applied to a site, such as a wound or burn, or to the eye, ear, lungs, nasal epithelia or other sites. In certain embodiments, formulations may be administered by, but limited to, inhalation, ingestion, and/or topical administration.

Antimicrobial peptides, such as BPI, PLUNC, Bombinins; Cecropins; LL-37; Magainins; Styelins; Clavanins; Melittin; Protegrin; Tachyplesins; Defensins; Insect defensins; alpha-, beta- and theta-Defensins; Plant defensins; Drosomycin; PR-39; Bac5; Bac7; Drosocin; Metchnikowin; Bactenecin; or Ranalexin are described in Koczulla and Bals, 2003, which is incorporated herein by reference.

Where a surfactant polypeptide or peptide is used in combination with antimicrobial agents or antibiotics, an "effective amount of an antimicrobial agent or antibiotic" means an amount, or dose, within the range normally given or prescribed, or a lowered dose as made available by a combination therapy with a surfactant PLUNC. Such ranges are well established in routine clinical practice and will thus be known to those of skill in the art or adjustable by such. As this invention provides for enhanced microbial and/or bacterial killing, it will be appreciated that effective amounts of an antimicrobial agent or antibiotic may be used that are lower than the standard doses previously recommended when the antimicrobial or antibiotic is combined with a surfactant composition of the invention.

The ID50/IC50 ratio required for safe use of the proposed surfactant polypeptide or peptide in combination with antimicrobial agents will be assessed by determining the ID50 (median lethal toxic dosage) and the IC50 (median effective therapeutic dosage) in experimental animals. The optimal dose for human subjects is then defined by fine-tuning the range in clinical trials. In the case of ID50, the antimicrobial polypeptide or peptide is usually administered to mice or rats (topically or orally) at several doses (usually 4-5) in the lethal rage. The dose in mg/kg is plotted against % mortality and the dose at 50% represents the ID50 (Klaassen, 1990). The IC50 is determined in a similar fashion as described by Cleeland and Squires (1991). In terms of modulating inflammatory responses, measures of the relative levels of release of inflammatory cytokines or stimulation of signaling by the NF-kappaB pathway might also be assessed.

In a clinical trial, the therapeutic dose would be determined by maximizing the benefit to the patient, whilst minimizing any side-effects or associated toxicities. Unless otherwise stated, these ranges refer to the amount of an agent to be administered orally, topically or by inhalation.

In the treatment of animals or human patients with combination therapy, there are various appropriate formulations and treatment regimens that may be used. For example, the surfactant polypeptide or peptide, and second agent(s) may be administered to an animal simultaneously, e.g., in the form of a single composition that includes the surfactant polypeptide and second agent, or by using at least two distinct compositions. The surfactant agent could also be administered to the animal prior to the second agent or the second agent may be given prior to the surfactant polypeptide.

Multiple combinations may also be used, such as more than one surfactant used with one or more second agent. Different classes of second agents and surfactant may be combined, naturally following the general guidelines known in the art regarding drug interactions.

Further embodiments of the invention include therapeutic kits that comprise, in suitable container means, a pharmaceutical formulation of at least one surfactant polypeptide and a pharmaceutical formulation, optionally with at least one antimicrobial agent or antibiotic. The surfactant and antimicrobial agent or antibiotic may be contained within a single container means, or a plurality of distinct containers may be employed.

Depending on the circumstances, surfactants may be employed in inhalant, oral, or topical treatment regimens.

B. Respiratory Therapy

The treatment regimens described herein can be combined with respiratory therapies. In certain embodiments, surfactant administration is performed on a patient, for example infants, who are intubated and maintained on ventilation, either conventional ventilation or high frequency ventilation, for a period of time or for the entire duration of the treatment. In a further aspect, a patient in need of surfactant therapy is identified and then administered a PLUNC therapy described herein. Also, patients with a mucociliary deficiency Primary Ciliary Dyskinesia (PCD), Cystic Fibrosis, Pseudohypoaldosteronism (PHA), chronic obstructive pulmonary disease (COPD), or the like may be treated with PLUNC enhanced therapies, e.g., in combination with chest physiotherapies typically used to treat such conditions.

Primary ciliary dyskinesia (PCD), also known as "immotile cilia syndrome" or "Kartagener Syndrome", is considered an unusual cause of persistent wheezing and cough in children. In addition to a chronic cough, this disease is also associated with recurrent or persistent infections of the lung, sinuses, and ears. Occurring in approximately 1 in 15,000 births, PCD is an inherited disease that causes impaired clearance of bacteria from the lung, paranasal sinuses, and middle ear. Half of the patients with PCD have their internal organs reversed, and men are usually infertile.

Occurring in all races, cystic fibrosis (CF) is the most common, inherited disease of Caucasians, and affects many parts of the body, including the lungs, paranasal sinuses, skin, pancreas, intestines, liver, and male reproductive tract. Historically, the diagnosis of CF has been based on the presence of typical clinical features and positive laboratory studies, including abnormal sweat tests or two identified mutant CF genes. However, it is clear that milder or variant forms of the disease exist, in which patients can have lung disease but normal or borderline elevated sweat tests or no identifiable mutant CF genes.

Pseudohypoaldosteronism (PHA) is a rare disease that causes increased lung fluids, and patients can have recurrent episodes of chest congestion and persistent cough.

Chronic obstructive pulmonary disease (COPD) affects 15 million patients in the U.S. and is the sixth leading cause of death. It is characterized by the retention of mucus secretions in the lungs. Many patients diagnosed with COPD have a disorder called chronic bronchitis (CB), and 600,000 patients are hospitalized each year due to an acute exacerbation of CB. Cystic fibrosis and Primary Ciliary Dyskinesia (PCD) are other examples of lung disorders which assume a clinical profile similar to COPD. Ciliary dyskinesia, whether primary or secondary, results in retained secretions that can only be cleared by coughing.

In healthy lungs, inhaled insoluble material such as bacteria, viruses, antigens, and toxins deposit in the tracheobronchial airway mucus and are removed from the lung in a matter of hours by mucociliary clearance (MCC). When MCC is overwhelmed or impaired, some mucus can be removed by mechanical or cough clearance (CC). Impairment of MCC typically leads to the accumulation of mucus in the airways, and this in turn is associated with acute infections, chronic bacterial colonization, and chronic inflammation.

In other embodiments, alternative modes of administration can be utilized, as well as alternative surfactant formulations. For example, surfactant can be formulated for aerosolization (nebulization) and administered via nasal continuous positive airway pressure (CPAP), nasal or naso-pharyngeal prongs in combination with low-flow oxygen, or via face mask or oxygen hood.

In certain embodiments, aerosolized pulmonary surfactant can be administered as provided in U.S. application Ser. No. 11/130,783, filed May 17, 2005, incorporated herein by reference in its entirety and for all purposes. Administration can be in conjunction with another noninvasive pulmonary respiratory therapy involving the administration of positive airway pressure. The term "noninvasive pulmonary respiratory therapy" refers to respiratory therapy which does not use mechanical ventilation and can include CPAP, bilevel positive airway pressure (BiPAP), synchronized intermittent mandatory ventilation (SIMV), and the like. The employment of such therapies involves the use of various respiratory gases, as would be appreciated by the skilled artisan. Respiratory gases used for noninvasive pulmonary respiratory therapy are sometimes referred to herein as "CPAP gas," "CPAP air," "nCPAP", "ventilation gas," "ventilation air," or simply "air." However, those terms are intended to include any type of gas normally used for noninvasive pulmonary respiratory therapy, including but not limited to gases and gaseous combinations listed above for use as the conditioning gas. In certain embodiments, the gas used for noninvasive pulmonary respiratory therapy is the same as the conditioning gas. In other embodiments, the respective gases are different from one another.

In certain embodiments, the pulmonary delivery methods are employed in conjunction with CPAP. It has been shown that use of CPAP allows for an increase in functional residual capacity and improved oxygenation. The larynx is dilated and supraglottic airway resistance is normal. There is also an improvement of the synchrony of respiratory thoracoabdominal movements and enhanced Hering-Breuer inflation reflex following airway occlusion. CPAP has been shown to be useful in treating various conditions such as sleep apnea, snoring, ARDS, IRDS, and the like.

In one aspect a pressure source and a delivery device or delivery apparatus are required. CPAP-producing airflow is typically generated in the vicinity of the nasal airways by converting kinetic energy from a jet of fresh humidified gas into a positive airway pressure. A continuous flow rate of breathing gas of about 5 to about 12 liters/minute generates a corresponding CPAP of about 2 to about 10 cm $H_2O$. Various modifications can be applied to the CPAP or other respiratory therapy systems to individualize the amount of pressure based on the patient's need.

Typically, flow rates and pressures suitable for achieving CPAP are based upon the characteristics of the patient being treated. Suitable flow rates and pressures can be readily calculated by the attending clinician. A variety of flow rates for the ventilating gas, including low, moderate and high flow rates can be used. Alternatively, the aerosol can be supplied without added positive pressure, i.e., without CPAP as a simultaneous respiratory therapy.

Typically, the air flow being delivered to the patient has a moisture level which will prevent unacceptable levels of drying of the lungs and airways. Thus, the generating air is often humidified by bubbling through a hydrator, or the like to achieve a relative humidity of greater that about 70%. The humidity may also be greater than about 85% or 98%.

The aerosol stream generated in accordance aerosolized delivery may be delivered to the patient via a nasal delivery device which can involve, for example masks, single nasal prongs, binasal prongs, nasopharyngeal prongs, nasal cannulae and the like. The delivery device is chosen so as to minimize trauma, maintain a seal to avoid waste of aerosol, and minimize the work the patient must perform to breathe.

When used as an aerosol preparation, the surfactant composition can be supplied in finely divided form, optionally in combination with a suitable propellant. Useful propellants are typically gases at ambient conditions and are condensed under pressure including, for example, lower alkanes and fluorinated alkanes, such as freon. In certain embodiments wherein the surfactant composition is delivered as an aerosol, the aerosol can be packaged in a suitable container under pressure.

Suitable dosage of the surfactant, whether aerosolized or delivered as a liquid or dry powder will be dependent on the patient's age and severity of the disorder and will be readily ascertainable by the attending clinician. The actual dosage of surfactant will of course vary according to factors such as the extent of exposure and particular status of the subject (e.g., the subject's age, size, fitness, extent of symptoms, susceptibility factors, and the like). By "effective dose" herein is meant a dose that produces effects for which it is administered.

When the surfactant is supplied to prematurely born infants as a liquid, an aliquot of the surfactant composition is delivered, preferably by intratracheal instillation, to provide an effective dose of surfactant in the lungs of the treated patient. A single surfactant dose may range from, for example, about 20 to about 300 mg total phospholipidid (TPL)/kg, or from about 60 to about 175 mg TPL/kg. It being understood, of course, that the exact dose of surfactant will depend upon factors such as the age and condition of the patient, the severity of the condition being treated, and other factors well within the skill of the attending clinician. In certain embodiments wherein the surfactant composition is delivered as an aerosol, such as disclosed in U.S. application Ser. No. 11/130, 783, filed May 17, 2005, the effective dose of lung surfactant can be, for example, from about 1 mg TPL/kg surfactant to about 1000 mg TPL/kg surfactant, or from about 2 mg TPL/kg surfactant to about 175 mg TPL/kg surfactant. In certain embodiments wherein the surfactant composition is delivered as a dry powder formulation, the effective dose of lung surfactant can be, for example, from about 1 mg TPL/kg surfactant to about 1000 mg or more TPL/kg surfactant, or from about 2 mg TPL/kg surfactant to about 175 mg TPL/kg surfactant. Other methods of delivery include lavage, lung wash, and the like. When so employed dose ranges are well within the skill of one in the art.

The frequency of dosing can vary, but typically is once every 2-3 days. In other embodiments, the patient is dosed more frequently, e.g., every 6-8 hours, twice daily, or once daily, or less frequently, e.g., twice weekly or even once weekly. In other embodiments, the patient can be dosed more frequently early in the treatment regimen, and with decreasing frequency later in the treatment regimen, e.g., once every other day for one week, followed by twice weekly until the end of the treatment period. Depending on the dosage form, e.g., aerosol or dry powder as compared with liquid instillate, the patient can be dosed continuously for part or all of the treatment period.

In other embodiments, a patient can be treated with other therapeutic, prophylactic or complementary agents, such as steroids, nitric oxide, antioxidants or reactive oxygen scavengers, bronchodilators, diuretics, antimicrobial or anti-infective agents, anti-hypertensive agents, or anti-inflammatory agents (e.g., PLA2 inhibitors, protease or elastase inhibitors, PDE-4 inhibitors, to name a few), as would be appreciated by one of skill in the art. Such treatment can include concomitant administration of the surfactant with other therapeutic, prophylactic or complementary agents. Concomitant administration can involve concurrent (i.e., at the same time), prior, or subsequent administration of the complementary agent with respect to the administration of the surfactant. When administered in combination, each component can be administered at the same time or sequentially in any order at different points in time. Thus, each component can be administered separately but sufficiently closely in time so as to provide the desired therapeutic effect. Concomitant administration of a surfactant with other therapeutic, prophylactic or complementary agents means administration of the surfactant and other agents at such time that both will have a therapeutic effect. A person of ordinary skill in the art, would have no difficulty determining the appropriate timing, sequence and dosages of administration for particular drugs of the present invention.

C. Surfactants

Products that may be mentioned as pulmonary surfactant preparations are Curosurf® (Poractant Alfa), a natural surfactant from homogenized porcine lungs; Survanta®, extract of bovine lungs; Alveofact® (Bovactant), extract of bovine lungs; Exosurf® (Colfosceril Palmitate), a synthetic phospholipid containing excipients; Surfacten® (Surfactant-TA), a pulmonary surfactant extracted from bovine lungs; Infasurf® (Calfactant), a surfactant extracted from calf lungs; Alec® (Pumactant), an artificial surfactant of DPPC and PG; and BLES®, a bovine lipid extract surfactant, to name a few.

Suitable pulmonary surfactant proteins are both the proteins obtained from natural sources, such as pulmonary lavage or extraction from amniotic fluid, and the proteins prepared by genetic engineering or chemical synthesis. In particular the pulmonary surfactant proteins designated by SP-B (Surfactant Protein-B) and SP-C (Surfactant Protein-C) and their modified derivatives may be used as pulmonary surfactants. The amino acid sequences of these pulmonary surfactant proteins, their isolation or preparation by genetic engineering are known (e.g., from WO 8603408, EP 0251449, WO 8904326, WO 8706943, WO 8803170, WO 9100871, EP 0368823 and EP 0348967). Modified derivatives of the pulmonary surfactant proteins designated by SP-C, which differ from human SP-C by the replacement of a few amino acids, are described, for example, in WO 9118015 and WO 9532992. Particularly to be emphasized in this connection are the recombinant SP-C (rSP-C) derivatives which are disclosed in WO 9532992, in particular those which differ from human SP-C in positions 4 and 5 by the substitution of cysteine by phenylalanine and in position 32 by the substitution of methionine by isoleucine (designated as rSP-C (FF/1) or Lusupultide or Venticute®). Other pulmonary surfactant proteins include those described in EP 0593094 and WO 9222315. The pulmonary surfactant may also comprise mixtures of different pulmonary surfactant proteins. In EP 0100910, EP 0110498, EP 0119056, EP 0145005 and EP 0286011 phospholipid compositions with and without pulmonary surfactant proteins are described which are likewise suitable as components of the preparations and methods described herein.

In one aspect, a surfactant can comprise a lipid. Lipids that may be used include the following classes of lipids: fatty acids and derivatives, mono-, di- and triglycerides, phospholipids, sphingolipids, cholesterol and steroid derivatives, terpenes, prostaglandins and vitamins. Fatty acids and derivatives thereof may include saturated and unsaturated fatty acids, odd and even number fatty acids, cis and trans isomers, and fatty acid derivatives including alcohols, esters, anhydrides, hydroxy fatty acids, and salts of fatty acids. Saturated and unsaturated fatty acids that may be used include molecules that have between 12 carbon atoms and 22 carbon atoms in either linear or branched form. Examples of saturated fatty acids that may be used include lauric, myristic, palmitic, and stearic acids. Examples of unsaturated fatty acids that may be used include lauric, physeteric, myristoleic, palmitoleic, petroselinic, and oleic acids. Examples of branched fatty acids that may be used include isolauric, isomyristic, isopalmitic, and isostearic acids and isoprenoids. Fatty acid derivatives include 12(((7'-diethylaminocoumarin-3 yl)carbonyl)methylamino)-octadecanoic acid; N-[12(((7'diethylaminocoumarin-3 yl) carbonyl)methylamino) octadecanoyl]aminopalmitic acid, N succinyl-dioleoylphosphatidylethanol amine and palmitoylhomocysteine; and/or combinations thereof. Mono, di- and triglycerides or derivatives thereof that may be used include molecules that have fatty acids or mixtures of fatty acids between 6 and 24 carbon atoms, digalactosyldiglyceride, 1,2-dioleoyl-snglycerol; 1,2-dipalmitoyl-sn-3 succinylglycerol; and 1,3-dipalmitoyl-2-succinylglycerol.

In one aspect, the surfactant comprises a phospholipid. Phospholipids that may be used include phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and .beta.-acyl-y-alkyl phospholipids. Examples of phosphatidylcholines include such as dioleoylphosphatidylcholine, dimyristoylphosphatidylcholine (DMPC), dipentadecanoylphosphatidylcholine dilauroylphosphatidylcholine, dipalmitoylphosphatidylcholine (DPPQ, distearoylphosphatidylcholine (DSPQ, diarachidoylphosphatidylcholine (DAPC), dibehenoylphosphatidylcholine (DBPQ, ditricosanoylphosphatidylcholine (DTPQ, dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used. Examples of phosphatidylethanolamines include dicaprylphosphatidylethanolamine, dioctanoylphosphatidylethanolamine, dilauroylphosphatidylethanolamine, dimyristoylphosphatidylethanolamine (DMPE), dipalmitoylphosphatidylethanolamine (DPPE), dipalmitoleoylphosphatidylethanolamine, distearoylphosphatidylethanolamine (DSPE), dioleoylphosphatidylethanolamine, and dilineoylphosphatidylethanolamine. Examples of phosphatidylglycerols include dicaprylphosphatidylglycerol, dioctanoylphosphatidylglycerol, dilauroylphosphatidylglycerol, dimyristoylphosphatidylglycerol (DMPG), dipalmitoylphosphatidylglycerol (DPPG), dipalmitoleoylphosphatidylglycerol, distearoylphosphatidylglycerol (DSPG), dioleoylphosphatidylglycerol, and dilineoylphosphatidylglycerol. Preferred phospholipids include DMPC, DPPC, DAPC, DSPC, DTPC, DBPC, DLPC, DMPG, DPPG, DSPG, DMPE, DPPE, and DSPE, and most preferably DPPC, DAPC and DSPC.

Sphingolipids that may be used include ceramides, sphingomyelins, cerebrosides, gangliosides, sulfatides and lysosulfatides. Examples of sphinglolipids include the gangliosides GM1 and GM2.

Steroids which may be used include cholesterol, cholesterol sulfate, cholesterol hemisuccinate, 6-(5-cholesterol 3.beta.-yloxy) hexyl-6-amino-6-deoxy-1-thio-.alpha.-Dgalactopyranoside, 6-(5-cholesten-3-yloxy)hexyl-6-amino-6-deoxy]-1-thio-(.alpha.-D mannopyranoside and cholesteryl (4'-trimethyl 35 ammonio)butanoate.

Additional lipid compounds that may be used include tocopherol and derivatives, and oils and derivatized oils such as stearlyamine.

A variety of cationic lipids such as DOTMA, N-[1-(2,3-dioleoyloxy)propylN,N,N-trimethylammonium chloride; DOTAP, 1,2-dioleoyloxy-3-(trimethylammonio) propane; and DOTB, 1,2-dioleoyl-3-(4'-trimethyl-ammonio) butanoyl-sn glycerol may be used.

A variety of other surfactants may be used including ethoxylated sorbitan esters, sorbitan esters, fatty acid salts, sugar esters, pluronics, tetronics, ethylene oxides, butylene oxides, propylene oxides, anionic surfactants, cationic surfactants, mono and diacyl glycerols, mono and diacyl ethylene glycols, mono and diacyl sorbitols, mono and diacyl glycerol succinates, alkyl acyl phosphatides, fatty alcohols, fatty amines and their salts, fatty ethers, fatty esters, fatty amides, fatty carbonates, cholesterol esters, cholesterol amides and cholesterol ethers.

Examples of anionic or cationic surfactants include aluminum monostearate, ammonium lauryl sulfate, calcium stearate, dioctyl calcium sulfosuccinate, dioctyl potassium sulfosuccinate, dioctyl sodium sulfosuccinate, emulsifying wax, magnesium lauryl sulfate, potassium oleate, sodium caster oil, sodium cetostearyl sulfate, sodium lauryl ether sulfate, sodium lauryl sulfate, sodium lauryl sulfbacetate, sodium oleate, sodium stearate, sodium stearyl fumarate, sodium tetradecyl sulfate, zinc oleate, zinc stearate, benzalconium chloride, cetrimide, cetrimide bromide, and cetylpyridinium chloride.

IV. Pharmaceutical Compositions

The phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the compositions, vectors or cells of the present invention, its use in therapeutic compositions is contemplated. Supplementary active ingredients also can be incorporated into the compositions.

In various embodiments, the surfactant polypeptides and any other agents that might be delivered may be formulated and administered in any pharmacologically acceptable vehicle, such as nebulizable, parenteral, topical, aerosal, liposomal, nasal, instillant, or ophthalmic preparations. In certain embodiments, formulations may be designed for ingestion, inhalation, instillation, or topical administration. It is further envisioned that formulations of surfactant polypeptides and any other agents that might be delivered may be formulated and administered in a manner that does not require that they be in a single pharmaceutically acceptable carrier. In those situations, it would be clear to one of ordinary skill in the art the types of diluents that would be proper for the proposed use of the surfactant and any secondary agents required.

The active compositions of the present invention may include classic pharmaceutical preparations. Administration of these compositions according to the present invention will be via any common route so long as the target tissue or surface is available via that route. This includes oral, nasal, buccal, respiratory, or topical. Such compositions would normally be administered as pharmaceutically acceptable compositions, described supra.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms.

The surfactant may be used without further modifications or it may be diluted in a pharmaceutically acceptable carrier. The surfactants may be used independently or in combination with antimicrobial agents. Because of the stability of the surfactant it is contemplated that the invention may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the lowering of surface tension or its results is desired.

V. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein, are examples, and are not intended as limitations on the scope of the invention. Changes therein and other uses which are encompassed within the spirit of the invention as defined by the scope of the claims will occur to those skilled in the art.

Example 1

Surfactant Comprising a PLUNC Polypeptide

Figure 3:
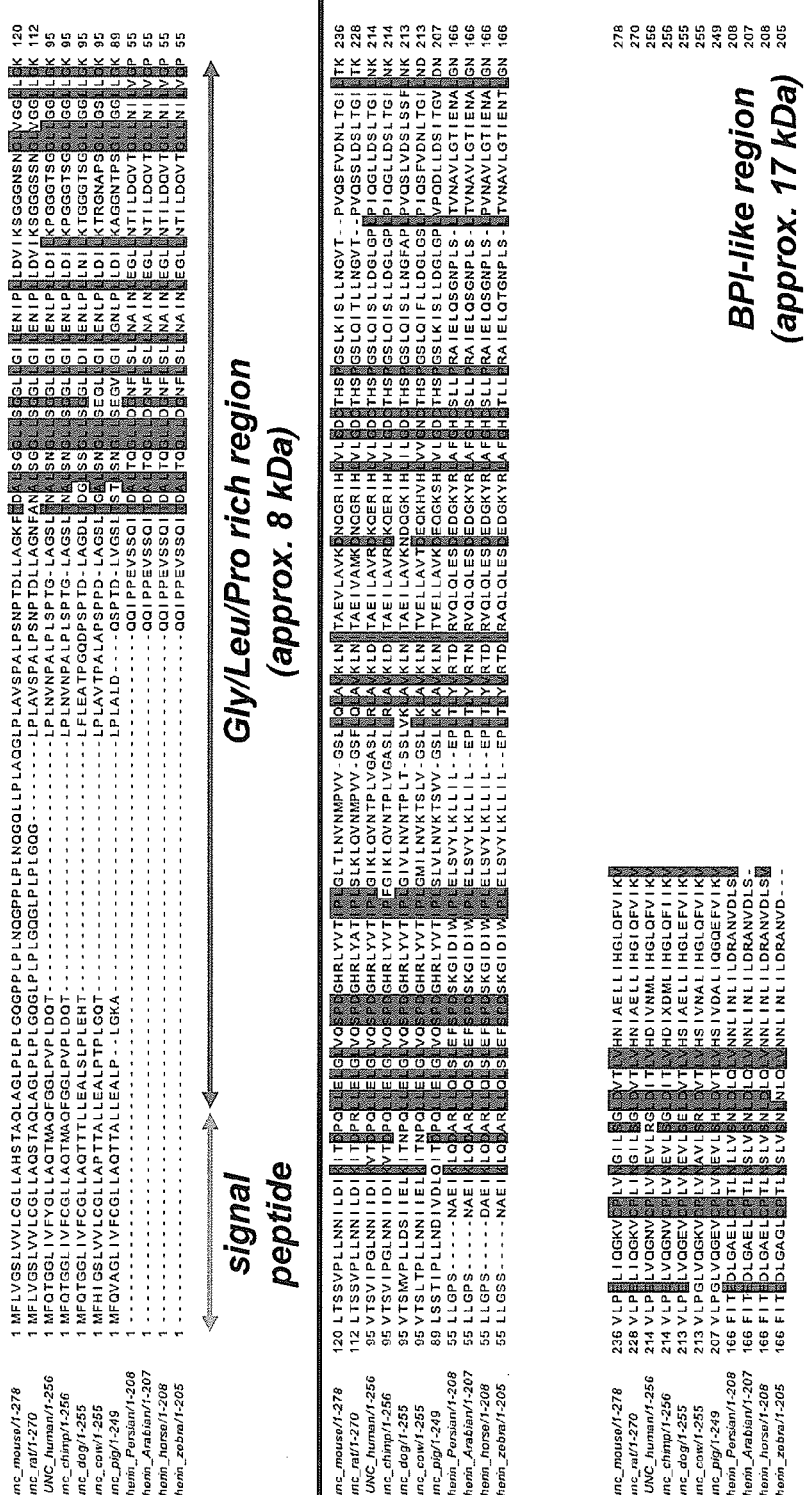
FIG. 3. Illustrates PLUNC/Latherin homology. Regions of identity indicated by shading.
Figure 4:
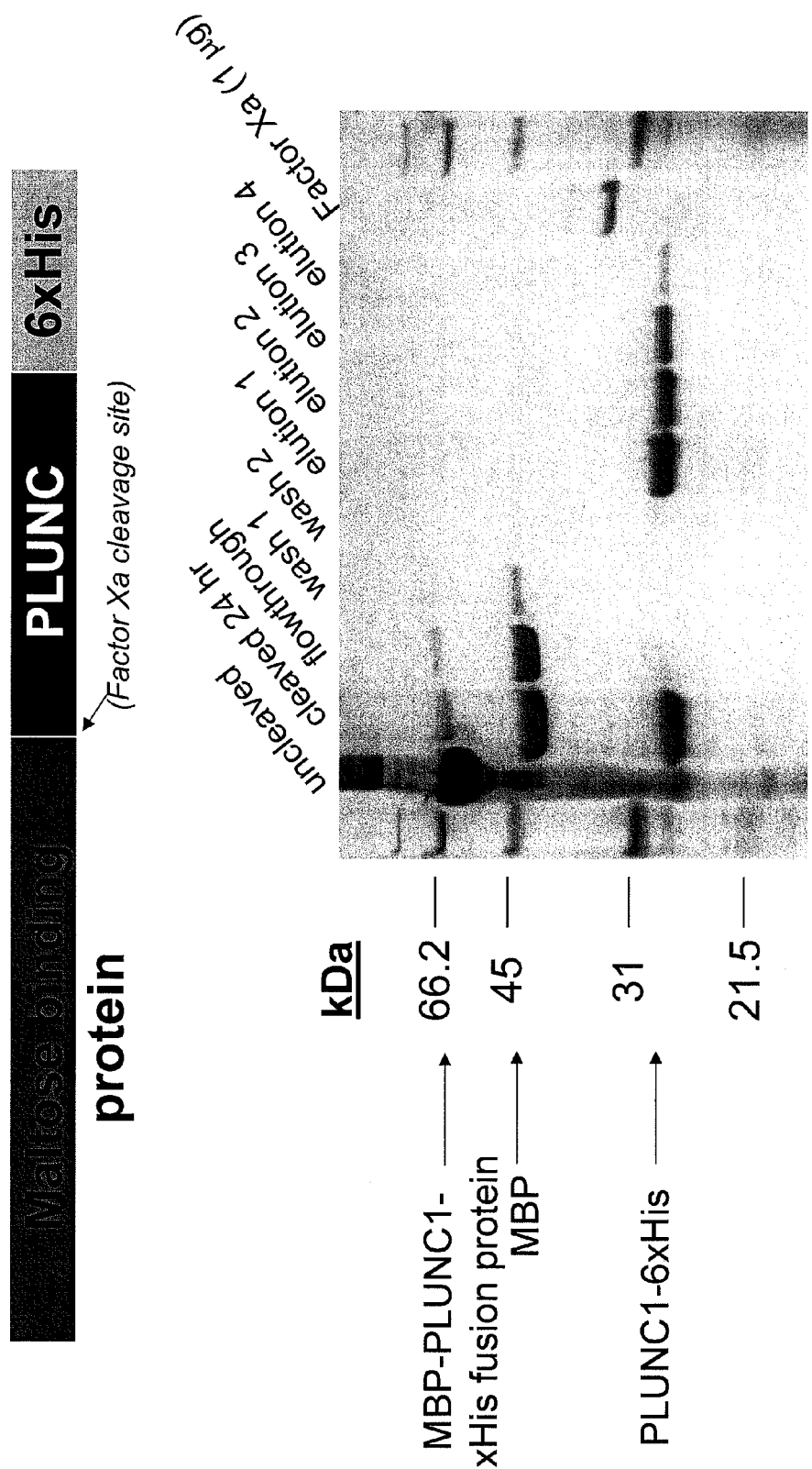
FIG. 4. Illustrates and example of recombinant PLUNC protein production in E. coli.
Figure 5:
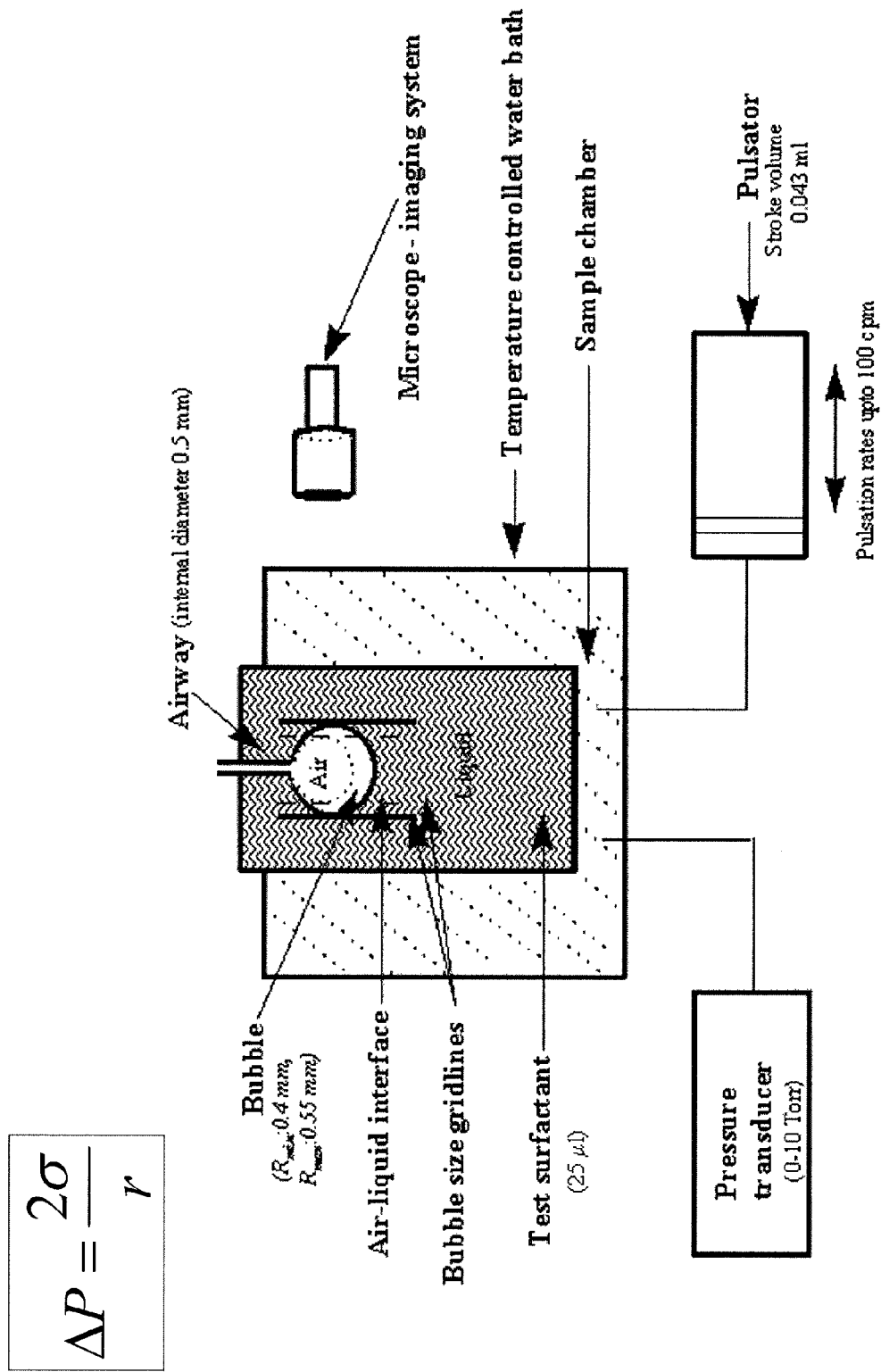
FIG. 5. Illustrates a Pulsating Bubble Surfactometer (PBS).
Figure 6A:
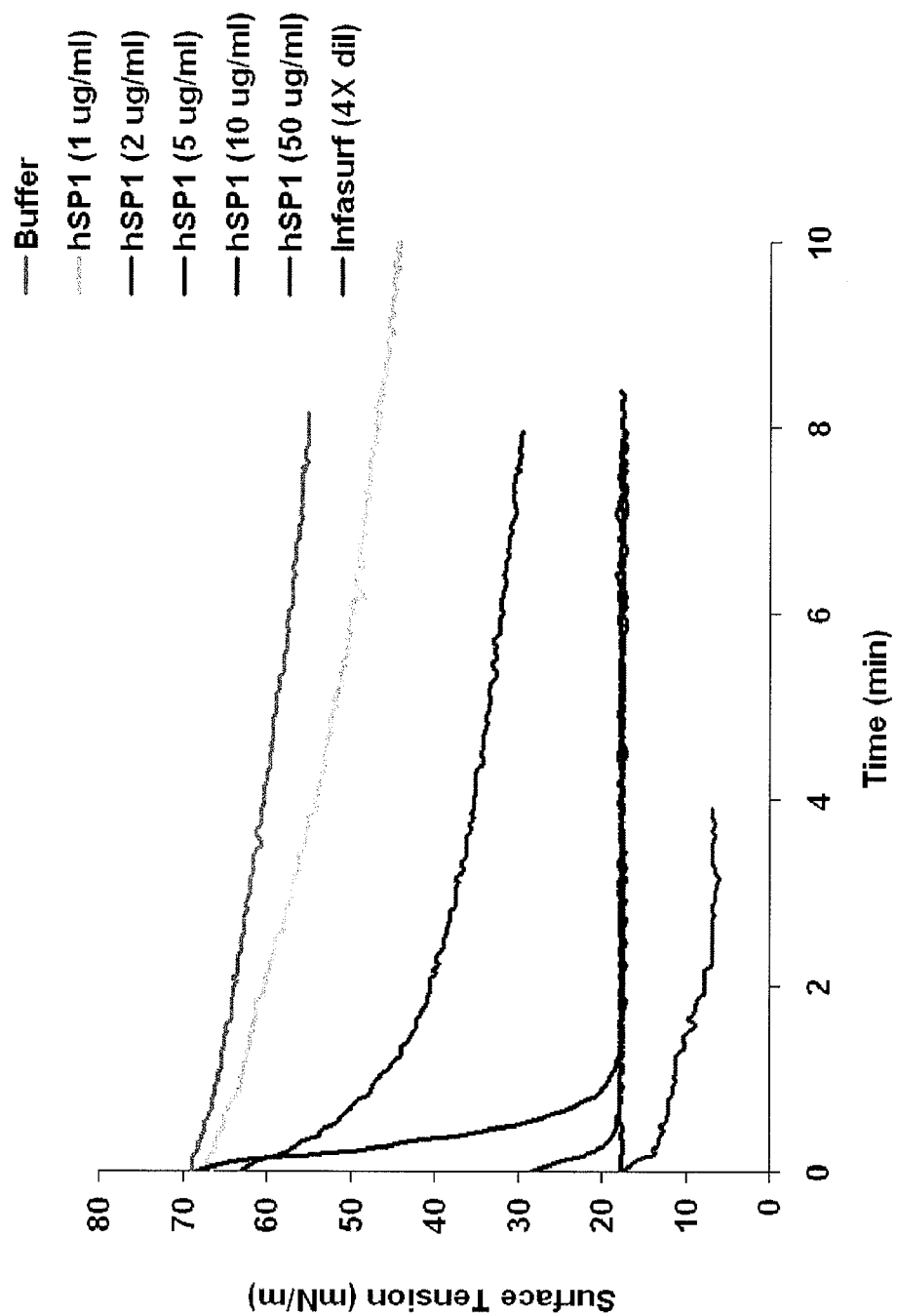
FIGS. 6A-6D. Illustrates physiologically relevant concentrations of PLUNC (hSP1, ~10 µg/ml) reduce the minimum surface tension achievable of a Tris or phosphate buffer solution to less than 20 mN/m.
Figure 6B:
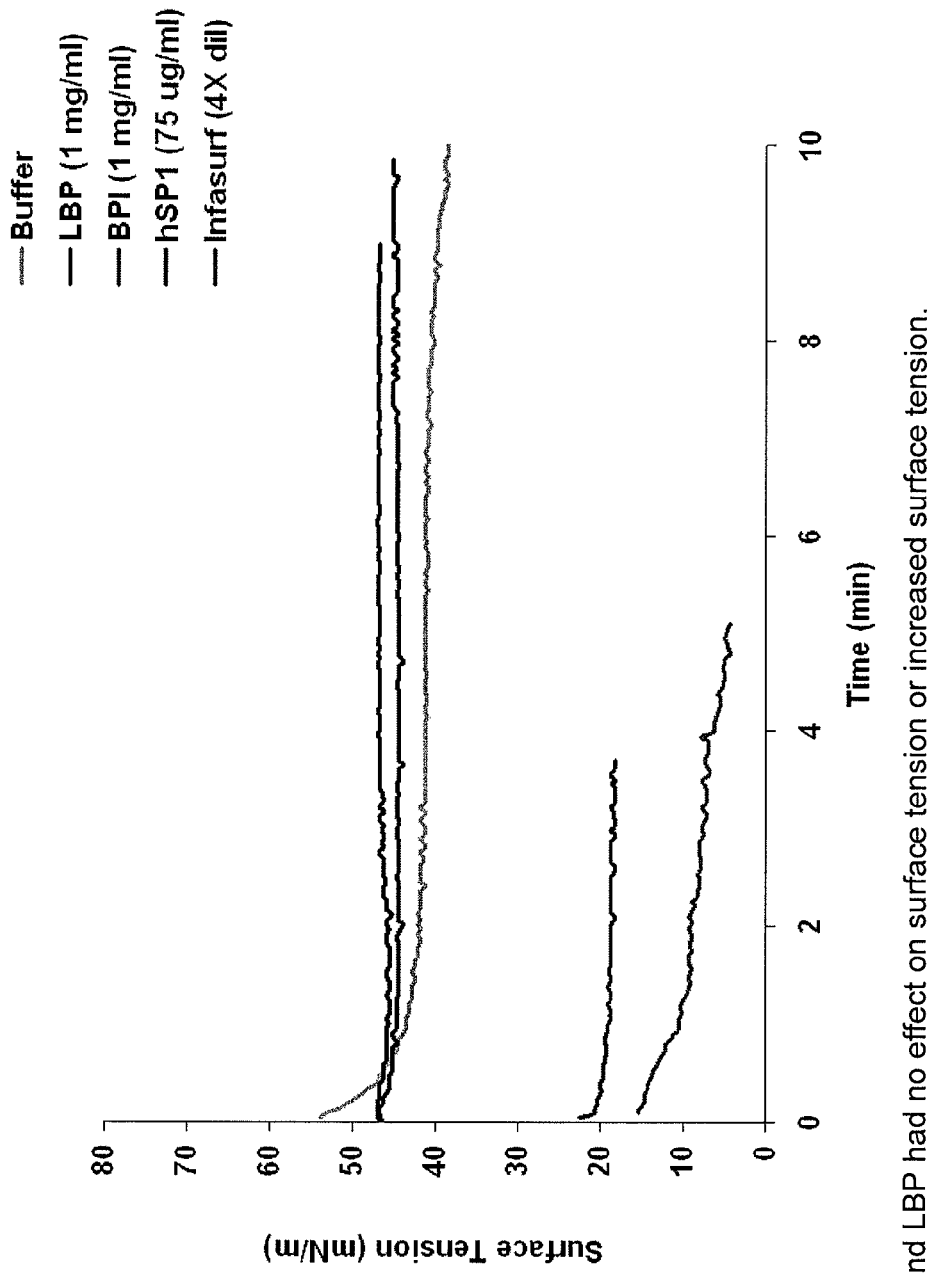

Gene profiling studies performed previously indicated that the PLUNC gene product is among the most frequently represented transcripts in cDNA libraries constructed from human airway epithelia (Scheetz et al., 2004), suggesting that PLUNC protein is extremely abundant in the conducting airways. A feature of the primary amino acid sequence of PLUNC is the hydrophobic nature of the protein. Secreted hydrophobic proteins are quite unusual in multicellular organisms. Examples include the pulmonary surfactant proteins B and C. The inventors performed BLAST searches and noted that PLUNC shares homology with an equine protein termed "latherin" (FIG. 3). Latherin is a secreted protein present in the sweat of horses that has demonstrated surfactant properties (Beeley et al., 1986). The inventors reasoned that PLUNC might also exhibit surfactant properties and prepared a recombinant human PLUNC protein with a C-terminal 6H is tag using an E. coli expression system (FIG. 4). The surface tension properties of recombinant PLUNC were evaluated using a pulsating bubble surfactometer (FIG. 5). PLUNC showed dose-dependent surface tension lowering properties (FIGS. 6A-D), a property not shared by two related proteins from this gene family, bactericidal permeability-increasing protein (BPI) and LPS binding protein (LBP) (FIG. 6B).

Figure 6C:
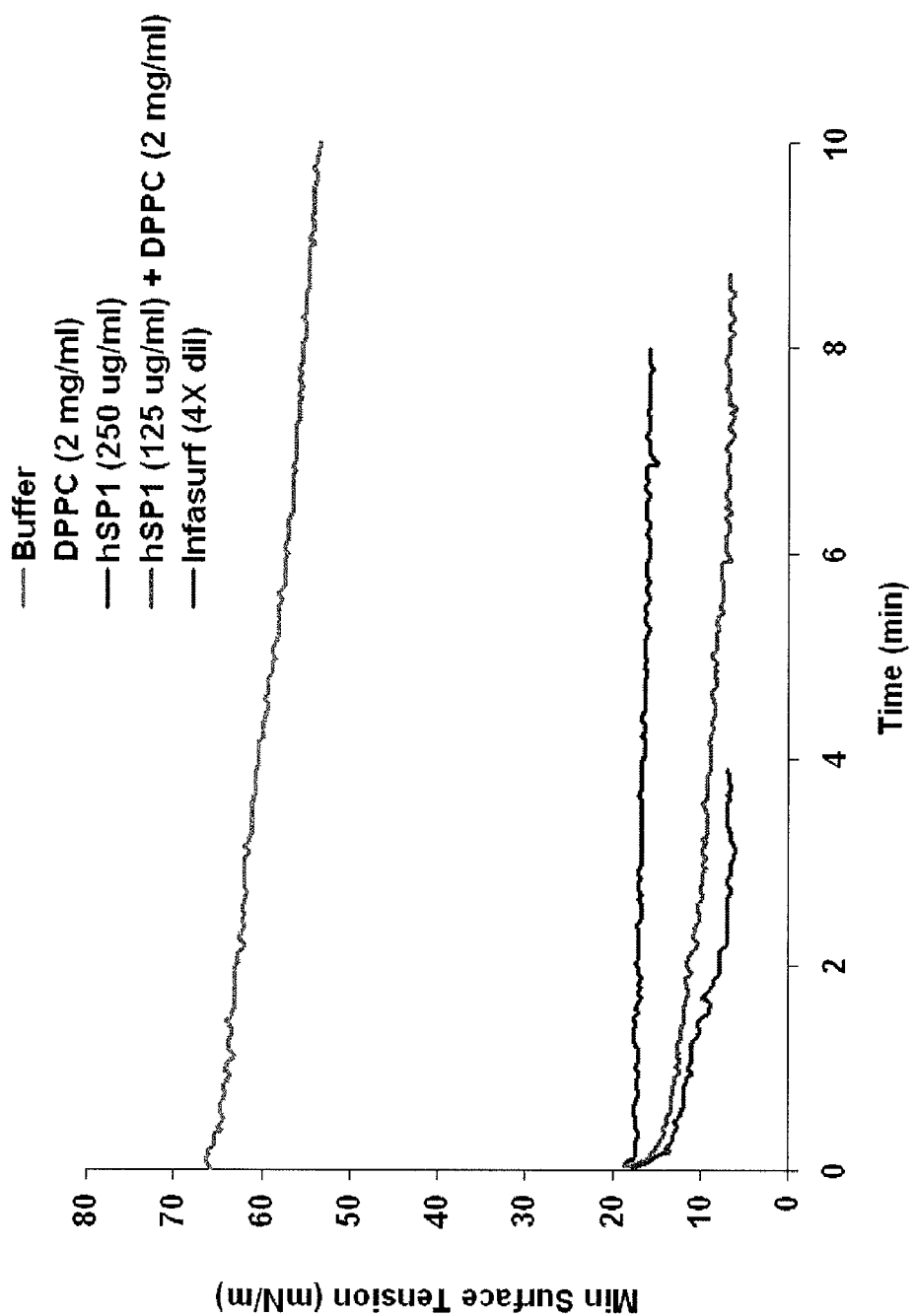
Figure 6D:
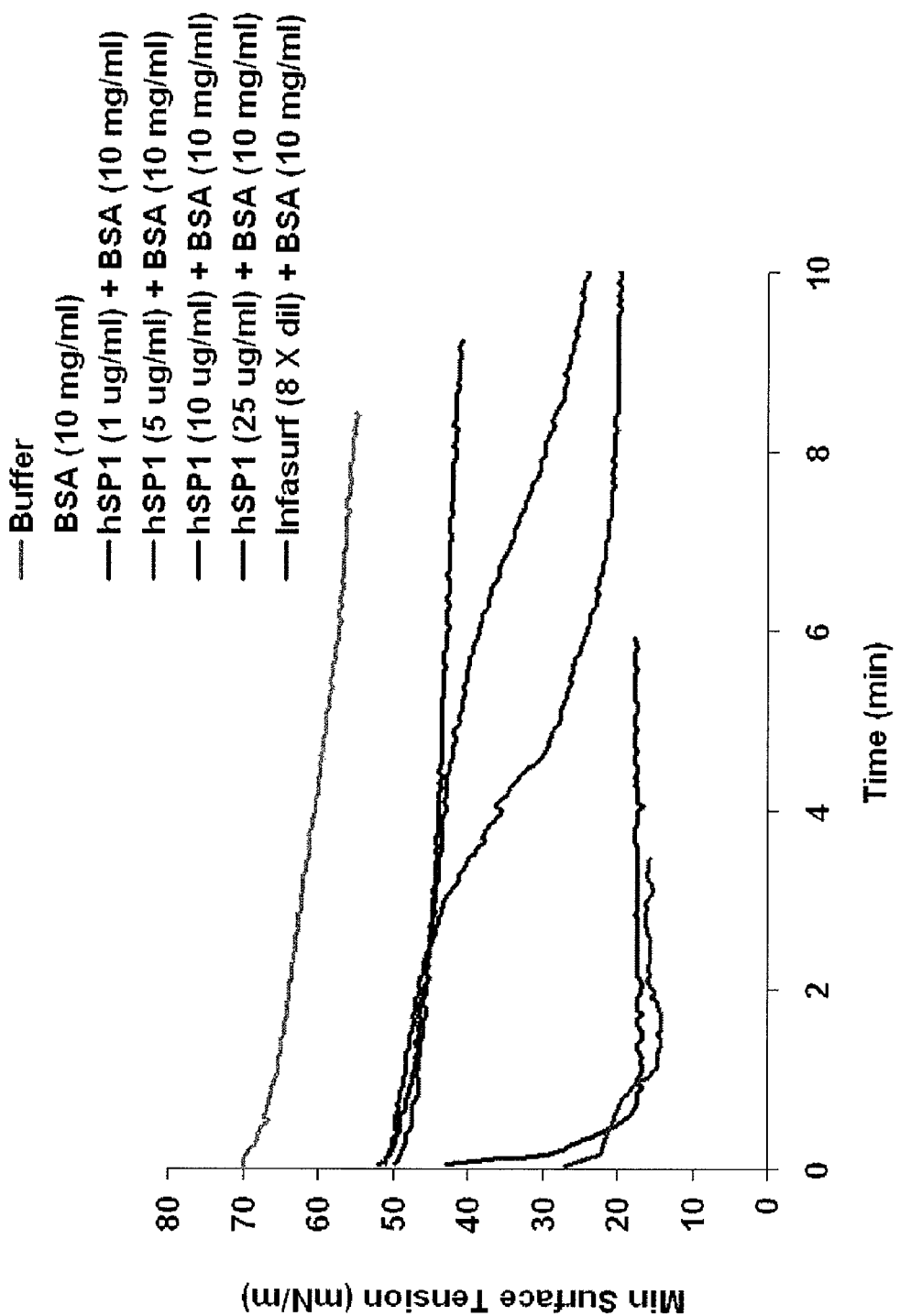

PLUNC has been shown, herein, to have surfactant properties. Furthermore, addition of a lipid component of pulmonary surfactant (DPPC) to PLUNC caused a further lowering of surface tension (FIG. 6C). This finding is similar to that reported for the pulmonary surfactant protein B. Furthermore, the addition of bovine serum albumin to a PLUNC solution inhibits its surface tension lowering properties, a feature shared by the therapeutic pulmonary surfactant Infasurf™ (FIG. 6D). The finding that PLUNC has surface tension lowering properties is novel and unexpected and was not predicted by the existing literature.

Studies indicate that PLUNC has surface tension lowering properties in the Eustachian tube (FIG. 7) and small airways. In this way, PLUNC may be used in therapeutic applications for surface tension lowering. Furthermore, the surfactant activity of the protein may enhance spreading of antimicrobial proteins and concentrate them at interfaces where there activities are needed, such as the airway lining liquid. In addition, this surfactant activity may aid the spreading, motility, and function of innate and adaptive immune cells at the liquid-air interface.

Furthermore, PLUNC has structural properties suggesting it may be a bi-functional secreted protein. On further analysis of the western blots of PLUNC protein in secretions from airway epithelia (FIG. 8), neutrophils (FIG. 2), and middle ear aspirates (FIG. 7), two immunoreactive forms of the protein were identified. One of ~25 kD in size consistent with the full length protein, and a second lower molecular weight form of ~17 kD suggests a C-terminal fragment. End sequencing of the 17 kD fragment was obtained and it confirmed that it represents a C-terminal cleavage product of the full length secreted protein (FIG. 9). As shown in FIG. 9, cleavage between G and K residues in the protein releases an N-terminal hydrophobic peptide and the C-terminal fragment that contains the region of the protein that is most similar to the neutrophil product BPI, a protein known to bind endotoxin and exhibit antimicrobial activities. The inventors contemplate that PLUNC is a novel bi-functional protein with the surfactant properties residing in the N-terminal portion of the molecule and anti-inflammatory and antimicrobial properties residing in the C-terminal fragment. It is possible that the hydrophobic N-terminus sterically hinders the activity of the C-terminal region in the full-length molecule.

Recombinant PLUNC protein was expressed in E. coli, as a fusion protein containing a cleavable N-terminal maltose binding protein (MBP) tag as well as a C-terminal 6×His tag. The MBP tag served to increase solubility of the markedly hydrophobic PLUNC protein, as well as to provide an epitope that could be utilized for purification of the recombinant protein. After purification of the fusion protein and cleavage of the MBP tag, a tendency for the remaining PLUNC-6×His product to precipitate was observed; thus, 0.005% Tween-20 (v/v) was present at most stages in the purification process in order to help maintain the stability of PLUNC in solution. However, to prevent interference from Tween-20 in ensuing biophysical analyses of PLUNC-6×His, Tween-20 was removed from the buffers at the final purification step. As shown in Lane 6 of FIG. 10, full-length PLUNC-6×His was obtained at the expected size of approximately 26 kDa, estimated to be ≧95% pure. The identity of this recombinant protein as PLUNC was verified by N-terminal sequencing and molecular weight determination using matrix assisted laser desroption/ionization—time of flight mass spectroscopy (MALDI-TOF), as well as by immunoblotting with anti-PLUNC antiserum (not shown).

Circular dichroism was used to investigate secondary structure of this recombinant PLUNC protein. The circular dichroism signal was negative in the 200-240 nm range, with dips around 208 and 222 nm indicating presence of secondary structure with some degree of alpha helices. Analysis of the circular dichroism data using the K2d CD secondary structure server resulted in a prediction of 24-33% alpha-helical, about 15% beta-sheet and 51-61% random coil structure for PLUNC. In comparison, the N-terminal region of BPI, to which PLUNC is believed to be similar (Bingle and Craven, 2002), is 27% alpha-helical, 46% beta-sheet and 27% random coil, while its C-terminal region (residues 250-456) is 24% alpha-helical, 44% beta-sheet and 32% random coil.

In studying the possible function of the PLUNC protein, the inventors considered its relationship to an equine PLUNC family member known as latherin, the only PLUNC homolog to have a described function to date. Latherin was originally isolated from horse sweat, and subsequently shown to display significant surface activity in a battery of in vitro assays (Beeley et al., 1986; Goubran Botros et al., 2001). On this basis, it was proposed that latherin is a surfactant protein. Like latherin, PLUNC is notably hydrophobic, with hydrophobic residues making up approximately 42.3% of its amino acid sequence. This is comparable to the observed hydrophobicity for latherin of 40.1%.

Figure 12A:
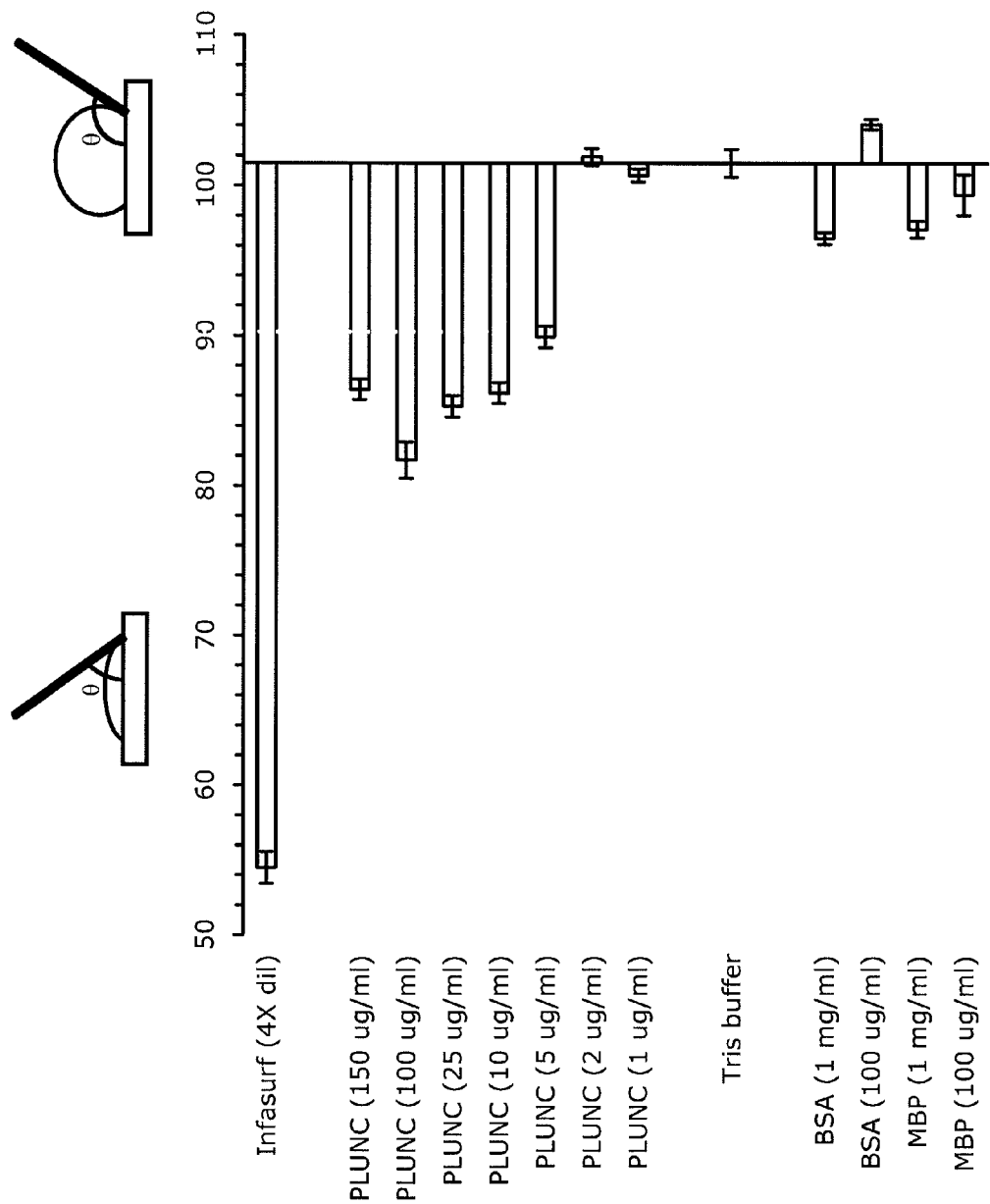
FIGS. 12A-12C. Illustrate contact angle measurements suggest that PLUNC possesses surface activity. Advancing contact angles measured by the sessile drop technique for various solutions dispensed onto (FIG. 12A) siliconized glass (hydrophobic) and (FIG. 12B) unmodified glass (hydrophilic) surfaces. Bars depict the mean values for contact angles (in degrees) measured one minute after drops were dispensed onto the solid surface. Error bars represent the standard error about the mean (n=6). Contact angles ($\theta$) of less than 90° (dotted line in FIG. 12A indicates wetting of the surface by the drop, whereas contact angles greater than 90° (to the right of the vertical line) indicate that a sample is "non-wetting". The solid vertical line separates the solutions that have greater wetting ability than buffer alone (bars pointing left) from the ones that have lesser wetting ability (bars pointing right). Measurements that are significantly different from buffer, as determined by Student's two-tailed t-test ($\alpha$=0.05) are indicated by an asterisk, with p-values shown in parentheses. On a hydrophobic surface, PLUNC solutions transition from "non-wetting" to "wetting" at concentrations greater than 10 µg/mL. On a hydrophilic surface, PLUNC enhances wetting when at lower concentrations (1-2 µg/ml), while higher PLUNC concentrations (5-150 µg/mL) appear to reduce wetting ability. Infasurf, a commercial lung surfactant, displays significant wetting ability on both hydrophilic and hydrophobic surfaces.
Figure 12B:
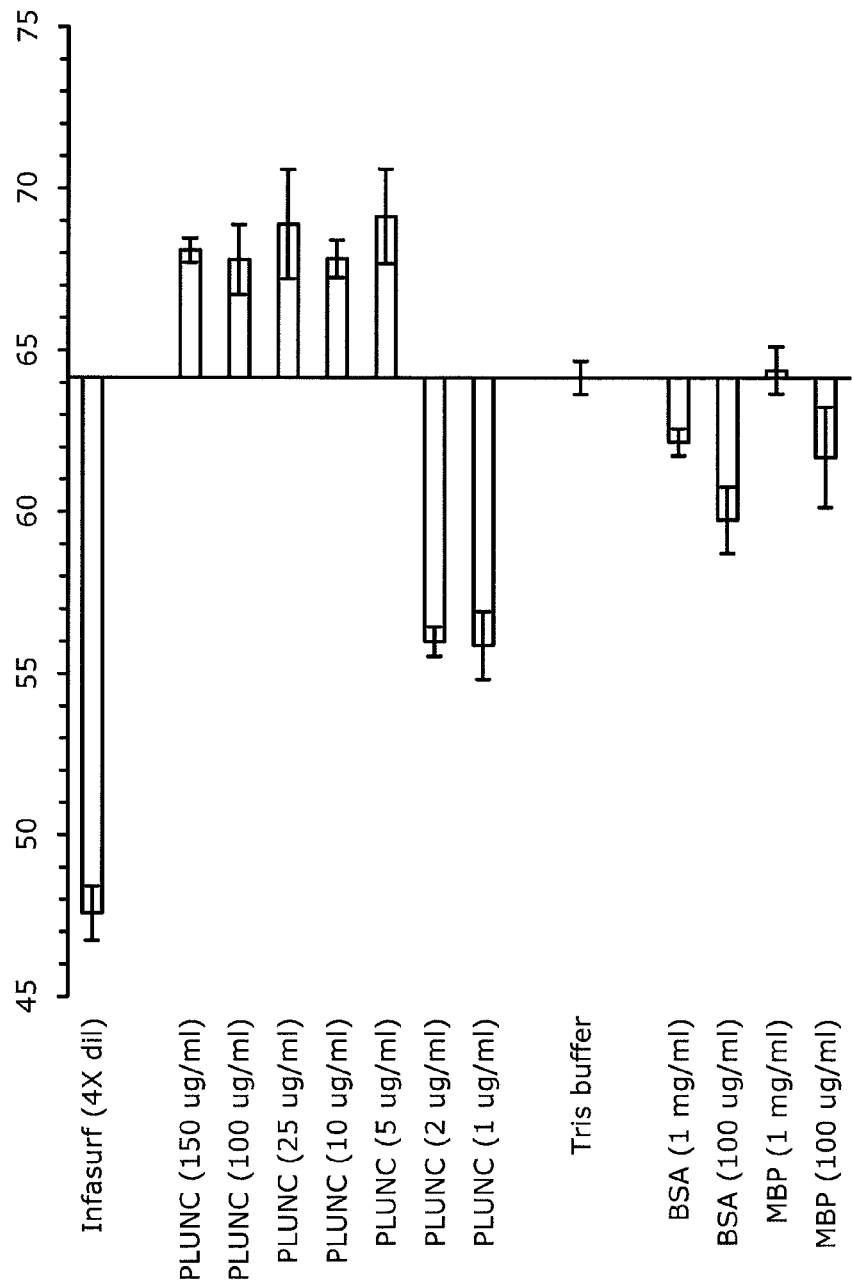

Given this interesting similarity, the inventors contemplated that PLUNC might play a surfactant-like role in airway fluids. To test this possibility, the effects of PLUNC on the surface activity of fluids at solid-liquid interfaces were assessed. As shown in FIG. 12, advancing contact angles for drops of various solutions on two types of surfaces were measured. Samples were first studied on a hydrophobic surface (siliconized glass) (FIG. 12A). In these experiments, the buffer control (20 mM Tris, 50 mM NaCl, pH 7.3) exhibited a mean contact angle of $101.5°\pm0.9$. In contrast, a solution containing purified recombinant His-tagged PLUNC at 150 µg/mL (the highest concentration tested) produced a statistically significant reduction of the contact angle to $86.4°\pm0.7$, an effect that was diminished as the PLUNC concentration decreased. Contact angles observed for the control proteins BSA and MBP (both at the relatively high concentration of 1 mg/mL) were very similar to those for buffer, suggesting that the effects observed for PLUNC were relatively potent and specific to that protein.

Figure 12C:
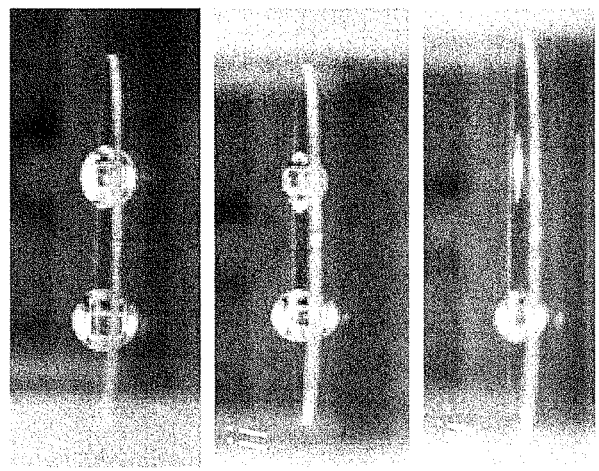

In these studies, "non-wetting" (i.e., non-spreading) solutions, such as buffer, exhibited advancing contact angles of greater than 90°, while "wetting" solutions (such as Infasurf, a commercial pulmonary surfactant preparation extracted from bovine lung) produced contact angles of less than 90°. Importantly, the presence of PLUNC in an aqueous solution appeared to cause contact angles to shift below this critical 90° angle, with PLUNC-containing solutions shifting from non-wetting to wetting behavior at concentrations between 5 and 10 µg/mL. The effects of PLUNC on surface spreading were particularly apparent in time course studies. As depicted in FIG. 12C, a drop of Tris buffered solution dispensed onto a hydrophobic surface exhibited very little surface spreading over a 45 minute time course, with some loss of volume due to evaporation. In contrast, a drop of a PLUNC-containing solution displayed nearly complete spreading over the same time period.

When solutions were dispensed onto a hydrophilic surface (glass) (FIG. 12B), all solutions were observed to spread over the glass surface (as evidenced by contact angles of less than 90°). However, at PLUNC concentrations greater than 5 µg/mL, contact angles were increased with respect to the buffer control, suggesting that PLUNC at these concentrations interfered to some extent with the spreading behavior of the aqueous solutions. Below this 5 µg/mL concentration, the presence of PLUNC protein appeared to enhance the wetting ability of the solution.

Figure 13:
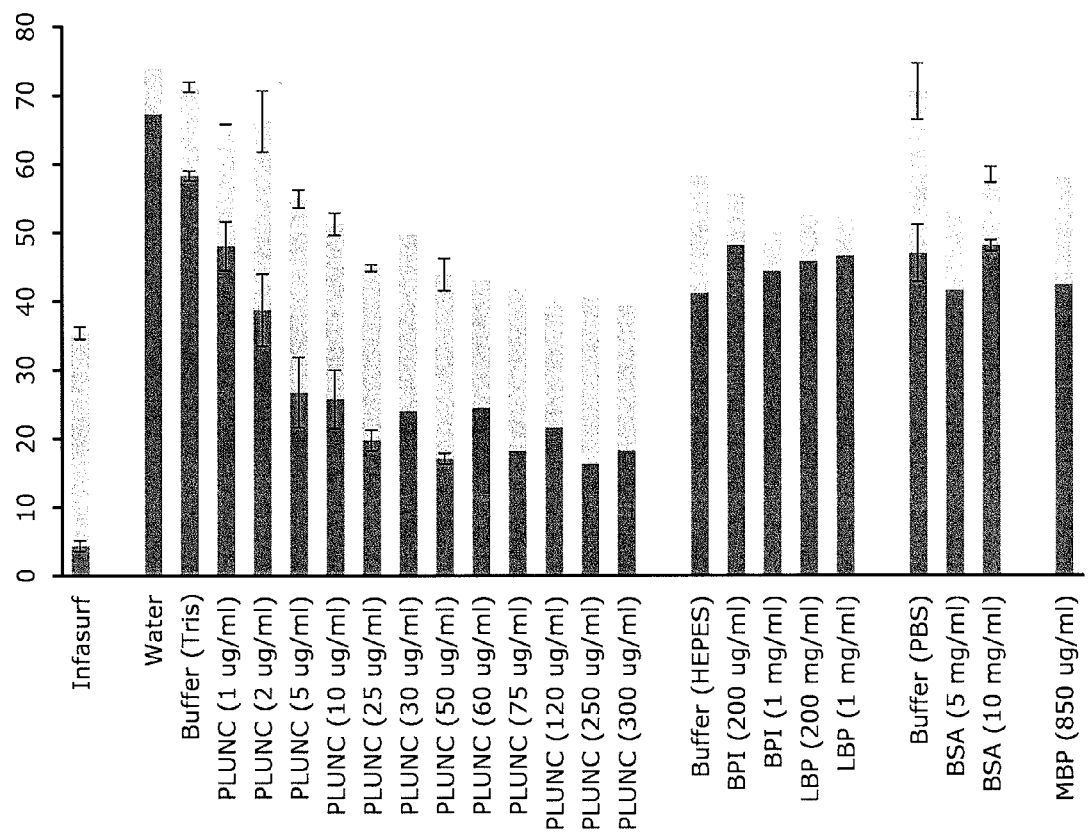
FIG. 13. Shows the reduction of surface tension at an air-liquid interface by PLUNC protein. The pulsating bubble surfactometer was used to measure dynamic surface tension in solutions containing increasing concentrations of recombinant His-tagged PLUNC. For each sample, the minimum surface achieved at 5 minutes of pulsation is shown as a gray bar. The range, representing the difference between the minimum and maximum surface tensions at the 5 minute time point, is depicted in white. Error bars, where present, represent the standard error about the mean (n=3 experiments).

The inventors then used a pulsating bubble surfactometer to study PLUNC effects at an air-liquid interface (FIG. 13). In these studies, the inventors observed that PLUNC significantly and rapidly reduced the minimum surface tension of a Tris-buffered solution, to a minimum value of approximately 18 mN/m. This effect was dose-dependent, with concentrations of only 5 µg/mL to 10 µg/mL required to observe maximal effects. Minimum surface tension could not be decreased beyond this value, no matter how much the PLUNC concentration was increased. As a positive control we also tested the effects of Infasurf, which contains a mixture of lipids and the surfactant proteins SP-B and SP-C. After 3-4 minutes of pulsation, minimum surface tensions of Infasurf preparations reached approximately 3 mN/m, consistent with potent surfactant activity.

Figure 14:
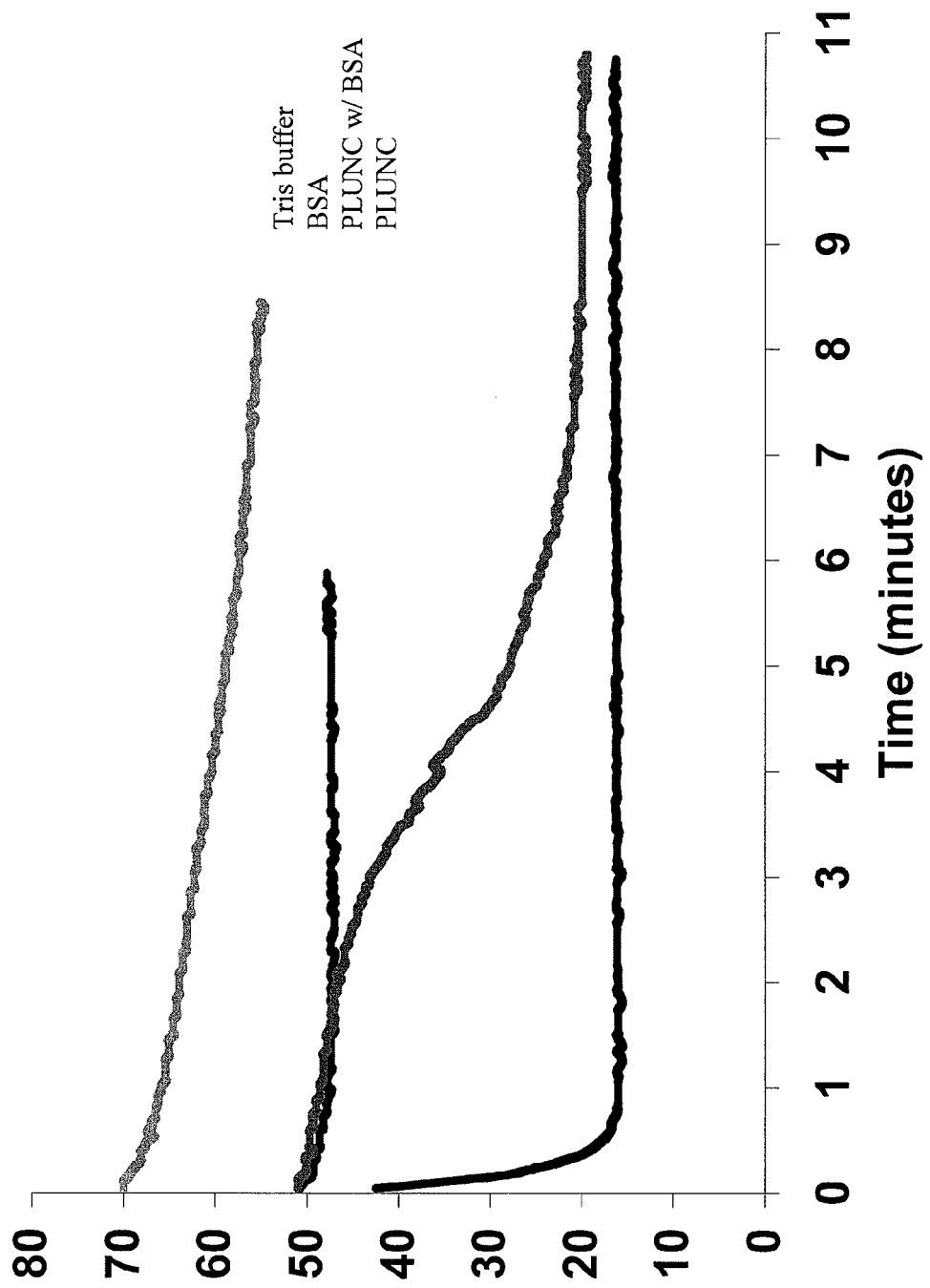
FIG. 14. Shows PLUNC interaction with albumin in the pulsating bubble surfactometer. The pulsating bubble surfactometer was used to measure dynamic surface tension in solutions containing mixtures of PLUNC-6×His and bovine serum albumin (BSA). Plotted values represent surface tension minima over time for Tris buffer (cyan), BSA at 10 mg/mL (red), PLUNC at 10 µg/mL (purple) or PLUNC (10 µg/mL) with BSA (10 mg/mL) (green). In the presence of BSA, it takes longer for PLUNC to reach its saturation value for minimum surface tension.

Interestingly, the PLUNC relatives BPI and LBP had no significant effects on minimum surface tension even at concentrations as high as 1 mg/mL, suggesting that surface tension reduction is not a general property of all LT/LBP family members and is instead unique to the PLUNC protein. Similarly, it was observed that highly concentrated solutions of BSA (5 mg/mL and 10 mg/mL) had only very modest effects on minimum surface tension. As the concentration of BSA used in these studies was orders of magnitude greater than the tested PLUNC concentrations, this strongly argues for a potent and specific surfactant activity by the PLUNC protein. The inventors also examined the interaction between PLUNC and BSA, which, like many plasma proteins, has a well documented role in inhibiting pulmonary surfactant components (Banerjee, 2004). In mixtures of PLUNC and BSA, BSA effects appeared to dominate early on in the surfactometer runs, but these effects were always eventually overcome by the surface tension lowering activities of PLUNC (FIG. 14). This pattern indicates that PLUNC effectively competes with BSA for space at the air-liquid interface.

The inventors also considered the range of surface tension values in the surfactometer studies. This represents the difference between maximum and minimum surface tension observed for each test solution during cycling. An effective surfactant will exhibit a broad range, reflecting an ability to rapidly adjust surface tension throughout pulsation, while a poor surfactant will exhibit a relatively small range. As shown in FIG. 13, PLUNC-6×His displayed dose-dependent surface tension lowering activity and exhibited ranges similar to those of the known surfactant Infasurf, and contrasted with the narrow ranges observed for control proteins including BPI, LBP, BSA and MBP.

Materials and Methods

Expression and purification of recombinant PLUNC-6× His. The cDNA for human PLUNC(NCBI accession number NM_016583) was cloned into the plasmid vector pMAL-c2x (New England Biolabs). Full-length fusion protein, containing a cleavable N-terminal maltose binding protein (MBP) tag and a C-terminal 6×His tag, was expressed in the *E. coli* strain BL21 Star (DE3) (Invitrogen Corp, Carlsbad, Calif.) and the protein purified by passing over amylose resin (New England Biolabs Inc., Ipswich, Mass.). MBP-tagged fusion protein was eluted from the amylose resin using Tris buffer (20 mM Tris, 50 mM NaCl, 0.005% Tween-20, pH 7.3) containing 10 mM maltose. Eluted fusion protein was concentrated to approximately 2 mg/ml under nitrogen pressure (40-50 psi) with stirring, using an Amicon Ultrafiltration membrane (30,000 MWCO; Millipore, Billerica, Mass.). Protein was then further resolved by passage through a Superdex 75 gel filtration column (Amersham; GE Healthcare, Pittsburg, Pa.). The resulting chromatogram indicated the presence of two peaks, corresponding to two distinct populations of recovered fusion protein. Both populations contained MBP-PLUNC-6×His (confirmed by Coomassie staining of the fractions on SDS-PAGE gels); however, the higher molecular weight portion (represented by the first peak) appeared to be resistant to cleavage by Factor Xa protease (New England Biolabs, Inc., Ipswich, Mass.). Fractions corresponding to the second peak were pooled and concentrated to approximately 1 mg/mL using Amicon Ultra-15 centrifugal filter units (30,000 MWCO; Millipore, Billerica, Mass.), followed by removal of the MBP tag by Factor Xa cleavage carried out for approximately 16 hours at 4° C. The cleavage products were passed over nickel resin (Ni Sepharose 6 Fast Flow; GE Healthcare Biosciences Corp., Piscataway, N.J.), and pure PLUNC-6×His eluted from the resin using Tris buffer (20 mM Tris, 50 mM NaCl, pH 7.3) containing 500 mM imidazole. As a final purification step, the protein was again passed over a Superdex 75 gel filtration column and fractions containing pure (≧95%) PLUNC-6×His were pooled and concentrated using Amicon Ultra-15 centrifugal filter units (10,000 MWCO; Millipore, Billerica, Mass.). Throughout the purification procedure, concentration estimates were calculated using absorbance at 280 nm (extinction coefficient 68,000 $M^{-1}$ $cm^{-1}$). Concentration estimates at the final purification step were obtained using the Bradford assay (Pierce Biotechnology, Inc., Rockford, Ill.).

Circular dichroism. Circular dichroism spectra were recorded for recombinant PLUNC in the range 197-260 nm using an Aviv 62DS spectrometer (Aviv Associates Inc., Lakewood, N.J.) and a quartz cuvette of 1 mm path length (Starna Cells, Atascadero, Calif.). Spectra were collected 5 times per sample and averaged for 3 different concentrations of PLUNC (0.54 mg/ml, 1.08 mg/ml and 2.16 mg/ml). Concentrations for the circular dichroism samples were estimated by Beer-Lambert's law using absorbance at 280 nm and a calculated extinction coefficient of 1490 $M^{-1}$ $cm^{-1}$. The percentage of secondary structure was calculated by deconvoluting the circular dichroism spectra using the online K2d CD secondary structure server, based on an unsupervised neural network algorithm (Andrade et al., 1993; Merelo et al., 1994).

Contact angle measurements. For wettability studies, 3-10 μL drops of solutions containing PLUNC, control proteins or Infasurf were dispensed onto Fisherbrand microscope glass cover slides (12-545-10, ThermoFisher Scientific, Pittsburgh, Pa.) or siliconized glass cover slides (Hampton Research, Aliso Viejo, Calif.). Advancing contact angles were measured by the sessile drop technique at room temperature, using a Ramé-Hart NRL 100-00 goniometer (Ramé-Hart Instrument Co., Mountain Lakes, N.J.). For each sample, 3 replicates were performed, in 2 different spots on the coverslide, for a total of 6 measurements per sample. Contact angle measurements were collected at 1, 2 and 3 minutes after drop formation. Measurements for each time point were averaged to obtain the mean contact angle for each sample, as well as to calculate standard error about the mean. For all samples, contact angles were observed to decrease with time, suggesting possible evaporative effects as the experiment was not done in a controlled humidified chamber. The trends were identical for the samples at any given time point, only the 1 minute measurements are reported here.

Pulsating bubble surfactometer. Surface tension effects were measured using a pulsating bubble surfactometer (General Transco, Inc., Largo, Fla.), originally described by Enhorning (Enhorning, 1977). To measure dynamic surface tension, a test solution was loaded into a disposable sample chamber, within which a spherical air bubble was formed that maintained contact with outside air. The air bubble was pulsated at a rate of 20 pulses per minute, between a defined minimum bubble radius of 0.4 mm and a maximum bubble radius of 0.55 mm (representing a 50% surface area change). Changes in pressure across the bubble interface were recorded and used to calculate surface tension values throughout cycling according to the Law of Laplace. For these studies, Infasurf® (Forest Pharmaceuticals, Inc., St. Louis, Mo.) was diluted 4-fold prior to loading into the surfactometer. Bovine serum albumin (BSA) for these studies was obtained from Sigma-Aldrich (St. Louis, Mo.) and maltose-binding protein (MBP) was obtained from New England Biolabs, Inc. (Ipswich, Mass.). Recombinant human BPI and LBP were generously provided by Dr. Jerrold Weiss at the University of Iowa. All proteins were maintained in a Tris buffer (20 mM Tris, 50 mM NaCl, pH 7.3), with the exception of BPI and LBP, which were maintained in HEPES buffer. Data were collected using the software supplied with the instrument and transferred to a computer for analysis. The minimum and maximum surface tension values for each pulsation cycle were extracted and plotted. To compare all samples simultaneously, surface tension values after 5 minutes of pulsation were used.

REFERENCES

The following references, to the extent that they provide exemplary procedural or other details supplementary to those set forth herein, are specifically incorporated herein by reference.

U.S. application Ser. No. 11/130,783
U.S. Pat. No. 4,554,101
Andrade et al., *Protein engineering* 6(4): 383-390, 1993.
Banerjee, *Colloids and surfaces* 34(2): 95-104, 2004.
Beamer et al., *Biochem. Pharmacol.*, 57:225-229, 1999.
Beamer et al., *Protein Sci.*, 7:906-914, 1998.
Beamer et al., *Science*, 276:1861-1864, 1997.
Beeley et al., *Biochem J.* 235:645-50, 1986.
Bingle and Bingle, *Biochim. Biophys. Acta*, 1493:363-367, 2000.
Bingle and Craven, *Hum. Molec. Genet.*, 11:937-943, 2002.
Bingle and Gorr, *Intl. J. Biochem. Cell Biol.*, 36(11):2144-2152, 2004.
Bingle et al., *Protein Sci.*, 13(2): 422-430, 2004.
Bruce et al., *Curr. Opin. Struct. Biol.*, 8:426-434, 1998.
Cleeland and Squires, In: *Antibiotics in Laboratory Medicine*, Satterfield (Ed), Williams & Wilkins, Philadelphia, 1991.
Current Protocols in Protein Science, John Wiley & Sons, Edited by: Coligan et al., 2003.
Dear et al. *EMBO J.*, 10, 2813-2819, 1991.
Elsbach and Weiss, *Curr. Opin. Immunol.*, 10:45-49, 1998.
Enhoming, *J. Appl. Physiol.*, 1977, 43:198-203, 1977.
European Pat. 0100910
European Pat. 0110498
European Pat. 0119056
European Pat. 0145005
European Pat. 0251449
European Pat. 0286011
European Pat. 0348967
European Pat. 0368823
European Pat. 0593094
Ghafouri et al., *Proteomics*, 2:112-120, 2002.
Goubran et al., *European J. Biochemistry/FEBS*, 268(10): 3126-3136, 2001.
Huuskinen et al. *J. Lipid Res.*, 40:1123-1130, 1999.
Kelley et al., *J. Mol. Biol.*, 299:499-520, 2000.
King et al., *Am. J. Physiol.* 1972, 223:715-726,
Kyte and Doolittle, *J. Mol. Biol.*, 57(1):105-32, 1982.
LeClair et al., *Biochem. Biophys. Res. Commun.*, 284:792-797, 2001.

LeClair et al., *Genomics*, 2002.
Leclair, *Biochem. Soc. Trans.*, 31:801-805, 2003.
Levy, *Antimicrob. Agents Chemother.*, 44:2925-2931, 2000.
Lindahl et al., *Electrophoresis*, 22:1795-1800, 2001.
Merelo et al., *Neurocomputing*, 6:443-454, 1994.
PCT Appln. WO 8603408
PCT Appln. WO 8706943
PCT Appln. WO 8803170
PCT Appln. WO 8904326
PCT Appln. WO 9100871
PCT Appln. WO 9118015
PCT Appln. WO 9222315
PCT Appln. WO 9532992
Reynolds, In: *Integrated host defense against infections*, Crystal et al. (Eds.), The Lung, 2nd Ed., NY, Raven Press, Ltd., 2353-2365, 1997.
Revak et al., *Am. Rev. Respir. Dis.*, 1986, 134:1258-1265
Robertson, *Lung*, 1980, 158:57-68
Sambrook et al., In: *Molecular cloning*, Cold Spring Harbor Laboratory Press, Cold Spring Harbor, N.Y., 2001.
Scheetz et al., *Physiol Genomics*, 17(1): 69-77, 2004.
Schumann et al., *Science*, 249:1429, 1990.
Schutte et al., *Proc. Natl. Acad. Sci.*, 99:2129-2133, 2002.
Sheppard et al., *J. Chem. Society*, 538, 1981.
Shimazu et al., *J. Exp. Med.*, 189:1777-1782, 1999.
Sung et al., *J. Biol. Chem.*, 277:12762-12769, 2002.
Tall, *Annu. Rev. Biochem.*, 64:235-257, 1995.
Welsh et al., In: *The Metabolic and Molecular Basis of Inherited Disease*, Scriver et al., (Eds.), 8th Ed., NY, McGraw-Hill, Inc., 5121-5189, 2001.
Weston et al. *J. Biol. Chem.*, 274:13698-13703, 1999.

What is claimed is:

1. A therapeutic method of lowering surface tension at a liquid-air interface comprising administering to a subject in need thereof an amount of an isolated palate, lung and nasal epithelial clone (PLUNC) polypeptide sufficient to lower the surface tension at the liquid-air interface, wherein said subject suffers from cystic fibrosis or chronic obstructive pulmonary disorder, and wherein the PLUNC polypeptide comprises at least 10 consecutive residues from amino acids 21 to 256 of SEQ ID NO:2.

2. The method of claim 1, wherein the PLUNC polypeptide comprises an amino acid sequence of 10 to 200 consecutive amino acids of amino acids 21 to 256 of SEQ ID NO:2.

3. The method of claim 1, wherein PLUNC polypeptide is administered at a dose of 1 μg to 100 mg per kg of body weight.

4. The method of claim 1, wherein the liquid-air interface is part of the respiratory system or auditory system of a subject.

5. The method of claim 4, wherein the liquid-air interface is present in a subject's upper respiratory system, trachea, mouth, or lungs.

6. The method of claim 4, wherein the liquid-air interface is present in a subject's Eustachian tubes.

7. The method of claim 4, wherein administration is by endotracheal administration.

8. The method of claim 4, wherein administration is by inhalation.

9. The method of claim 4, further comprising a second therapy.

10. The method of claim 9, wherein the second therapy is a respiratory therapy.

11. The method of claim 10, wherein the respiratory therapy is conventional ventilation, high frequency ventilation, or continuous positive airway pressure.

12. The method of claim 9, wherein the second therapy is administration of one or more therapeutic agents.

13. The method of claim 12, wherein the other therapeutic agents are nitric oxide, steroids, antioxidants, vitamins, vitamin derivatives, reactive oxygen scavengers, bronchodilators, diuretics, antimicrobial agents, anti-infective agents, anti-hypertensive agents or anti-inflammatory agents.

14. The method of claim 1, further comprising administering a pulmonary surfactant.

15. The method of claim 14, wherein the pulmonary surfactant is Poractant Alfa, Beractant, Bovactant, Colfosceril Palmitate, Surfactant-Ta, Calfactant, Pumactant, Lusupultide or Sinapultide.

16. The method of claim 1, further comprising administering an antibiotic to said subject.

17. The method of claim 16, wherein the antibiotic therapy comprises administration of penicillin, ampicillin, amoxycillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraaminosalicylic acid, or ethambutol.

18. A method of enhancing effectiveness of anti-microbial agents comprising administering to a subject in need thereof a palate, lung and nasal epithelial clone (PLUNC) polypeptide comprising at least 10 consecutive residues of amino acids 21 to 256 of SEQ ID NO:2 and an anti-microbial, wherein the PLUNC polypeptide lowers the surface tension of a liquid-air interface and enhances dispersion of the anti-microbial, wherein said subject suffers from cystic fibrosis or chronic obstructive pulmonary disorder.

19. The method of claim 18, wherein the PLUNC polypeptide is an amino terminal fragment of a PLUNC polypeptide comprises an amino acid sequence of 10 to 200 amino acids of the amino terminal sequence of SEQ ID NO:2.

20. A method of enhancing effectiveness of a surfactant comprising administering to a subject in need thereof a palate, lung and nasal epithelial clone (PLUNC) polypeptide comprising at least 10 consecutive residues of amino acids 21 to 256 of SEQ ID NO:2 and a surfactant, wherein the PLUNC polypeptide lowers the surface tension of a liquid-air interface produced by the surfactant alone, and wherein said subject suffers from cystic fibrosis or chronic obstructive pulmonary disorder.

21. The method of claim 1, wherein the PLUNC polypeptide comprises amino acids 21 to 256 of SEQ ID NO:2.

22. The method of claim 18, wherein the PLUNC polypeptide comprises amino acids 21 to 256 of SEQ ID NO:2.

23. The method of claim 20, wherein the PLUNC polypeptide is an amino terminal fragment of a PLUNC polypeptide comprises an amino acid sequence of 10 to 200 amino acids of the amino terminal sequence of SEQ ID NO:2.

24. The method of claim 20, wherein the PLUNC polypeptide comprises amino acids sequence 21 to 256 of SEQ ID NO:2.

* * * * *

SEQUENCE LISTING

<160> NUMBER OF SEQ ID NOS: 24

<210> SEQ ID NO 1
<211> LENGTH: 1011
<212> TYPE: DNA
<213> ORGANISM: Homo sapiens

<400> SEQUENCE: 1

```
aggacagctg ctgagacctc taagaagtcc agatactaag agcaaagatg tttcaaactg      60
ggggcctcat tgtcttctac gggctgttag cccagaccat ggcccagttt ggaggcctgc     120
ccgtgcccct ggaccagacc ctgcccttga atgtgaatcc agccctgccc ttgagtccca     180
caggtcttgc aggaagcttg acaaatgccc tcagcaatgg cctgctgtct gggggcctgt     240
tgggcattct ggaaaacctt ccgctcctgg acatcctgaa gcctggagga ggtacttctg     300
gtggcctcct tgggggactg cttggaaaag tgacgtcagt gattcctggc ctgaacaaca     360
tcattgacat aaaggtcact gaccccccagc tgctggaact tggccttgtg cagagccctg     420
atggccaccg tctctatgtc accatccctc tcggcataaa gctccaagtg aatacgcccc     480
tggtcggtgc aagtctgttg aggctggctg tgaagctgga catcactgca gaaatcttag     540
ctgtgagaga taagcaggag aggatccacc tggtccttgg tgactgcacc cattcccctg     600
gaagcctgca aatttctctg cttgatggac ttggccccct ccccattcaa ggtcttctgg     660
acagcctcac agggatcttg aataaagtcc tgcctgagtt ggttaagggc aacgtgtgcc     720
ctctggtcaa tgaggttctc agaggcttgg acatcaccct ggtgcatgac attgttaaca     780
tgctgatcca cggactacag tttgtcatca aggtctaagc cttccaggaa ggggctggcc     840
tctgctgagc tgcttcccag tgctcacaga tggctggccc atgtgctgga agatgacaca     900
gttgccttct ctccgaggaa cctgccccct ctcctttccc accaggcgtg tgtaacatcc     960
catgtgcctc acctaataaa atggctcttc ttatgcaaaa aaaaaaaaa a              1011
```

<210> SEQ ID NO 2
<211> LENGTH: 256
<212> TYPE: PRT
<213> ORGANISM: Homo sapiens

<400> SEQUENCE: 2

```
Met Phe Gln Thr Gly Gly Leu Ile Val Phe Tyr Gly Leu Leu Ala Gln
 1               5                  10                  15

Thr Met Ala Gln Phe Gly Gly Leu Pro Val Pro Leu Asp Gln Thr Leu
            20                  25                  30
```

```
Pro Leu Asn Val Asn Pro Ala Leu Pro Leu Ser Pro Thr Gly Leu Ala
         35                  40                  45

Gly Ser Leu Thr Asn Ala Leu Ser Asn Gly Leu Leu Ser Gly Gly Leu
     50                  55                  60

Leu Gly Ile Leu Glu Asn Leu Pro Leu Leu Asp Ile Leu Lys Pro Gly
 65                  70                  75                  80

Gly Gly Thr Ser Gly Gly Leu Leu Gly Gly Leu Gly Lys Val Thr
                 85                  90                  95

Ser Val Ile Pro Gly Leu Asn Asn Ile Ile Asp Ile Lys Val Thr Asp
             100                 105                 110

Pro Gln Leu Leu Glu Leu Gly Leu Val Gln Ser Pro Asp Gly His Arg
         115                 120                 125

Leu Tyr Val Thr Ile Pro Leu Gly Ile Lys Leu Gln Val Asn Thr Pro
     130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                 165                 170                 175

Leu Gly Asp Cys Thr His Ser Pro Gly Ser Leu Gln Ile Ser Leu Leu
             180                 185                 190

Asp Gly Leu Gly Pro Leu Pro Ile Gln Gly Leu Leu Asp Ser Leu Thr
         195                 200                 205

Gly Ile Leu Asn Lys Val Leu Pro Glu Leu Val Lys Gly Asn Val Cys
     210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                 245                 250                 255

<210> SEQ ID NO 3
<211> LENGTH: 1646
<212> TYPE: DNA
<213> ORGANISM: Homo sapiens

<400> SEQUENCE: 3
gcccgggaga ggagaggagc gggccgagga ctccagcgtg cccaggtctg gcatcctgca    60
cttgctgccc tctgacacct gggaagatgg ccggcccgtg gaccttcacc cttctctgtg   120
gtttgctggc agccaccttg atccaagcca ccctcagtcc cactgcagtt ctcatcctcg   180
gcccaaaagt catcaaagaa aagctgacac aggagctgaa ggaccacaac gccaccagca   240
tcctgcagca gctgccgctg tcagtgccat gcgggaaaaa gccagccgga ggcatccctg   300
tgctgggcag cctggtgaac accgtcctga agcacatcat ctggctgaag gtcatcacag   360
ctaacatcct ccagctgcag gtgaagccct cggccaatga ccaggagctg ctagtcaaga   420 tcccccctgga catggtggct ggattcaaca cgcccctggt caagaccatc gtggagttcc   480
acatgacgac tgaggcccaa gccaccatcc gcatggacac cagtgcaagt ggccccaccc   540
gcctggtcct cagtgactgt gccaccagcc atgggagcct gcgcatccaa ctgctgcata   600
agctctcctt cctggtgaac gccttagcta agcaggtcat gaacctccta gtgccatccc   660
tgcccaatct agtgaaaaac cagctgtgtc ccgtgatcga ggcttccttc aatggcatgt   720
atgcagacct cctgcagctg gtgaaggtgc ccatttccct cagcattgac cgtctggagt   780
ttgaccttct gtatcctgcc atcaagggtg acaccattca gctctacctg ggggccaagt   840
tgttggactc acagggaaag gtgaccaagt ggttcaataa ctctgcagct tccctgacaa   900
```

-continued

```
tgcccaccct ggacaacatc ccgttcagcc tcatcgtgag tcaggacgtg gtgaaagctg      960
cagtggctgc tgtgctctct ccagaagaat tcatggtcct gttggactct gtgcttcctg     1020
agagtgccca tcggctgaag tcaagcatcg ggctgatcaa tgaaaaggct gcagataagc     1080
tgggatctac ccagatcgtg aagatcctaa ctcaggacac tcccgagttt tttatagacc     1140
aaggccatgc caaggtggcc caactgatcg tgctggaagt gtttccctcc agtgaagccc     1200
tccgcccttt gttcaccctg ggcatcgaag ccagctcgga agctcagttt tacaccaaag     1260
gtgaccaact tatactcaac ttgaataaca tcagctctga tcggatccag ctgatgaact     1320
ctgggattgg ctggttccaa cctgatgttc tgaaaaacat catcactgag atcatccact     1380
ccatcctgct gccgaaccag aatggcaaat taagatctgg ggtcccagtg tcattggtga     1440
aggccttggg attcgaggca gctgagtcct cactgaccaa ggatgccctt gtgcttactc     1500
cagcctcctt gtggaaaccc agctctcctg tctcccagtg aagacttgga tggcagccat     1560
cagggaaggc tgggtcccag ctgggagtat gggtgtgagc tctatagacc atccctctct     1620
gcaatcaata aacacttgcc tgtgat                                          1646
```

<210> SEQ ID NO 4
<211> LENGTH: 484
<212> TYPE: PRT
<213> ORGANISM: Homo sapiens

<400> SEQUENCE: 4

```
Met Ala Gly Pro Trp Thr Phe Thr Leu Leu Cys Gly Leu Leu Ala Ala
  1               5                  10                  15

Thr Leu Ile Gln Ala Thr Leu Ser Pro Thr Ala Val Leu Ile Leu Gly
             20                  25                  30

Pro Lys Val Ile Lys Glu Lys Leu Thr Gln Glu Leu Lys Asp His Asn
         35                  40                  45

Ala Thr Ser Ile Leu Gln Gln Leu Pro Leu Leu Ser Ala Met Arg Glu
     50                  55                  60

Lys Pro Ala Gly Gly Ile Pro Val Leu Gly Ser Leu Val Asn Thr Val
 65                  70                  75                  80

Leu Lys His Ile Ile Trp Leu Lys Val Ile Thr Ala Asn Ile Leu Gln
                 85                  90                  95

Leu Gln Val Lys Pro Ser Ala Asn Asp Gln Glu Leu Leu Val Lys Ile
            100                 105                 110

Pro Leu Asp Met Val Ala Gly Phe Asn Thr Pro Leu Val Lys Thr Ile
        115                 120                 125

Val Glu Phe His Met Thr Thr Glu Ala Gln Ala Thr Ile Arg Met Asp
    130                 135                 140

Thr Ser Ala Ser Gly Pro Thr Arg Leu Val Leu Ser Asp Cys Ala Thr
145                 150                 155                 160

Ser His Gly Ser Leu Arg Ile Gln Leu Leu His Lys Leu Ser Phe Leu
                165                 170                 175

Val Asn Ala Leu Ala Lys Gln Val Met Asn Leu Leu Val Pro Ser Leu
            180                 185                 190

Pro Asn Leu Val Lys Asn Gln Leu Cys Pro Val Ile Glu Ala Ser Phe
        195                 200                 205

Asn Gly Met Tyr Ala Asp Leu Leu Gln Leu Val Lys Val Pro Ile Ser
    210                 215                 220

Leu Ser Ile Asp Arg Leu Glu Phe Asp Leu Leu Tyr Pro Ala Ile Lys
225                 230                 235                 240
```

```
Gly Asp Thr Ile Gln Leu Tyr Leu Gly Ala Lys Leu Leu Asp Ser Gln
                245                 250                 255

Gly Lys Val Thr Lys Trp Phe Asn Asn Ser Ala Ala Ser Leu Thr Met
            260                 265                 270

Pro Thr Leu Asp Asn Ile Pro Phe Ser Leu Ile Val Ser Gln Asp Val
        275                 280                 285

Val Lys Ala Ala Val Ala Ala Val Leu Ser Pro Glu Glu Phe Met Val
    290                 295                 300

Leu Leu Asp Ser Val Leu Pro Glu Ser Ala His Arg Leu Lys Ser Ser
305                 310                 315                 320

Ile Gly Leu Ile Asn Glu Lys Ala Ala Asp Lys Leu Gly Ser Thr Gln
                325                 330                 335

Ile Val Lys Ile Leu Thr Gln Asp Thr Pro Glu Phe Phe Ile Asp Gln
            340                 345                 350

Gly His Ala Lys Val Ala Gln Leu Ile Val Leu Glu Val Phe Pro Ser
        355                 360                 365

Ser Glu Ala Leu Arg Pro Leu Phe Thr Leu Gly Ile Glu Ala Ser Ser
    370                 375                 380

Glu Ala Gln Phe Tyr Thr Lys Gly Asp Gln Leu Ile Leu Asn Leu Asn
385                 390                 395                 400

Asn Ile Ser Ser Asp Arg Ile Gln Leu Met Asn Ser Gly Ile Gly Trp
                405                 410                 415

Phe Gln Pro Asp Val Leu Lys Asn Ile Ile Thr Glu Ile Ile His Ser
            420                 425                 430

Ile Leu Leu Pro Asn Gln Asn Gly Lys Leu Arg Ser Gly Val Pro Val
        435                 440                 445

Ser Leu Val Lys Ala Leu Gly Phe Glu Ala Ala Glu Ser Ser Leu Thr
    450                 455                 460

Lys Asp Ala Leu Val Leu Thr Pro Ala Ser Leu Trp Lys Pro Ser Ser
465                 470                 475                 480

Pro Val Ser Gln

<210> SEQ ID NO 5
<211> LENGTH: 1041
<212> TYPE: DNA
<213> ORGANISM: Homo sapiens

<400> SEQUENCE: 5
agcagactgt gcagtggggc aaggatttca tgagcatcct cctctaaacg cgtgtcaaga      60
caaaagatgc ttcagctttg gaaacttgtt ctcctgtgcg gcgtgctcac tgggacctca     120
gagtctcttc ttgacaatct tggcaatgac ctaagcaatg tcgtggataa gctggaacct     180
gttcttcacg agggacttga cacagttgac aatactctta aaggcatcct tgagaaactg     240
aaggtcgacc taggagtgct tcagaaatcc agtgcttggc aactggccaa gcagaaggcc     300
caggaagctg agaaattgct gaacaatgtc atttctaagc tgcttccaac taacacggac     360 attttgggt tgaaaatcag caactccctc atcctggatg tcaaagctga accgatcgat     420
gatggcaaag gccttaacct gagcttccct gtcaccgcga atgtcactgt ggccgggccc     480
atcattggcc agattatcaa cctgaaagcc tccttggacc tcctgaccgc agtcacaatt     540
gaaactgatc cccagacaca ccagcctgtt gccgtcctgg agaatgcgc cagtgaccca     600 accagcatct cactttcctt gctggacaaa cacagccaaa tcatcaacaa gttcgtgaat     660
agcgtgatca acacgctgaa agcactgta cctccctgc tgcagaagga gatatgtcca     720
ctgatccgca tcttcatcca ctccctggat gtgaatgtca ttcagcaggt cgtcgataat     780
```

```
cctcagcaca aaacccagct gcaaaccctc atctgaagag gacgaatgag gaggaccact    840
gtggtgcatg ctgattggtt cccagtggct tgccccaccc ccttatagca tctccctcca    900
ggaagctgct gccaccacct aaccagcgtg aaagcctgag tcccaccaga aggaccttcc    960
cagatacccc ttctcctcac agtcagaaca gcagcctcta cacatgttgt cctgcccctg   1020
gcaataaagg cccatttctg c                                             1041
```

```
<210> SEQ ID NO 6
<211> LENGTH: 249
<212> TYPE: PRT
<213> ORGANISM: Homo sapiens

<400> SEQUENCE: 6

Met Leu Gln Leu Trp Lys Leu Val Leu Leu Cys Gly Val Leu Thr Gly
 1               5                  10                  15

Thr Ser Glu Ser Leu Leu Asp Asn Leu Gly Asn Asp Leu Ser Asn Val
                20                  25                  30

Val Asp Lys Leu Glu Pro Val Leu His Glu Gly Leu Glu Thr Val Asp
            35                  40                  45

Asn Thr Leu Lys Gly Ile Leu Glu Lys Leu Lys Val Asp Leu Gly Val
        50                  55                  60

Leu Gln Lys Ser Ser Ala Trp Gln Leu Ala Lys Gln Lys Ala Gln Glu
 65                  70                  75                  80

Ala Glu Lys Leu Leu Asn Asn Val Ile Ser Lys Leu Leu Pro Thr Asn
                 85                  90                  95

Thr Asp Ile Phe Gly Leu Lys Ile Ser Asn Ser Leu Ile Leu Asp Val
                100                 105                 110

Lys Ala Glu Pro Ile Asp Asp Gly Lys Gly Leu Asn Leu Ser Phe Pro
            115                 120                 125

Val Thr Ala Asn Val Thr Val Ala Gly Pro Ile Ile Gly Gln Ile Ile
        130                 135                 140

Asn Leu Lys Ala Ser Leu Asp Leu Leu Thr Ala Val Thr Ile Glu Thr
145                 150                 155                 160

Asp Pro Gln Thr His Gln Pro Val Ala Val Leu Gly Glu Cys Ala Ser
                165                 170                 175

Asp Pro Thr Ser Ile Ser Leu Ser Leu Leu Asp Lys His Ser Gln Ile
            180                 185                 190

Ile Asn Lys Phe Val Asn Ser Val Ile Asn Thr Leu Lys Ser Thr Val
        195                 200                 205

Ser Ser Leu Leu Gln Lys Glu Ile Cys Pro Leu Ile Arg Ile Phe Ile
210                 215                 220

His Ser Leu Asp Val Asn Val Ile Gln Gln Val Val Asp Asn Pro Gln
225                 230                 235                 240

His Lys Thr Gln Leu Gln Thr Leu Ile
                245
```

```
<210> SEQ ID NO 7
<211> LENGTH: 1112
<212> TYPE: DNA
<213> ORGANISM: Homo sapiens

<400> SEQUENCE: 7
agggttccac atgttgctct cccaatgtga gcaagccctg gtggcagcgc agggtccag     60 tgcagccccct ccccacagca tgctgggggc taattctgat gtcatctttc tgcagaaaac   120
cattagacca tccctccaga ctgccaccct caaagccgtc tgcccaggcc ccatctgaca   180
```

-continued

```
ctcttgacat ctgcaggtcc cagaccctat gatgtgtcca ctctggaggc tcctcatctt    240
cctcgggttg ctggccttgc ccttggcacc acacaagcag ccttggcctg gcctggccca    300
agcccacaga gacaacaaat ccaccctggc aagaattatt gctcagggcc tcataaagca    360
caacgcagaa agccgaattc agaacatcca ctttggggac agactgaatg cctcagcaca    420
agtggcccca gggctggtgg gctggctaat cagcggcagg aaacaccagc agcagcaaga    480
gagcagcatc aacatcacca acattcagct ggactgtggt gggatccaga tatcattcca    540
taaggagtgg ttctcggcaa atatctcact tgaatttgac cttgaattga daccgtcctt    600
cgataacaac atcgtaaaga tgtgtgcaca tatgagcatc gttgtggagt tctggctgga    660
gaaagacgag tttggccgga gggatctggt gataggcaaa tgcgatgcag agcccagcag    720
tgtccatgtg gccatcctca ctgaggctat cccaccaaag atgaatcagt ttctctacaa    780
cctcaaagag aatctgcaaa aagttctccc acacatggta gaaagtcagg tatgtcctct    840
gatcggtgaa atcctcgggc agctggatgt gaaactgttg aaaagcctca tagaacagga    900
ggctgctcat gaaccaaccc accatgaaac cagccaaccc tctgcatgcc aggctggaga    960
gtcccccagc tgacttctgc tgatcagaag gaaagtccca atcttgcaac cttaagtctc    1020
ccttagagtg gggcttctgc taccctaaaa actttacccc aggctctgtg gacataccat    1080
cctctcctac aataaactct agctctgaaa aa                                  1112
```

<210> SEQ ID NO 8
<211> LENGTH: 254
<212> TYPE: PRT
<213> ORGANISM: Homo sapiens

<400> SEQUENCE: 8

```
Met Met Cys Pro Leu Trp Arg Leu Leu Ile Phe Leu Gly Leu Leu Ala
 1               5                  10                  15

Leu Pro Leu Ala Pro His Lys Gln Pro Trp Pro Gly Leu Ala Gln Ala
             20                  25                  30

His Arg Asp Asn Lys Ser Thr Leu Ala Arg Ile Ile Ala Gln Gly Leu
         35                  40                  45

Ile Lys His Asn Ala Glu Ser Arg Ile Gln Asn Ile His Phe Gly Asp
     50                  55                  60

Arg Leu Asn Ala Ser Ala Gln Val Ala Pro Gly Leu Val Gly Trp Leu
 65                  70                  75                  80

Ile Ser Gly Arg Lys His Gln Gln Gln Glu Ser Ser Ile Asn Ile
                 85                  90                  95

Thr Asn Ile Gln Leu Asp Cys Gly Gly Ile Gln Ile Ser Phe His Lys
            100                 105                 110

Glu Trp Phe Ser Ala Asn Ile Ser Leu Glu Phe Asp Leu Glu Leu Arg
        115                 120                 125

Pro Ser Phe Asp Asn Asn Ile Val Lys Met Cys Ala His Met Ser Ile
    130                 135                 140

Val Val Glu Phe Trp Leu Glu Lys Asp Glu Phe Gly Arg Arg Asp Leu
145                 150                 155                 160

Val Ile Gly Lys Cys Asp Ala Glu Pro Ser Ser Val His Val Ala Ile
                165                 170                 175

Leu Thr Glu Ala Ile Pro Pro Lys Met Asn Gln Phe Leu Tyr Asn Leu
            180                 185                 190

Lys Glu Asn Leu Gln Lys Val Leu Pro His Met Val Glu Ser Gln Val
        195                 200                 205
```

Cys Pro Leu Ile Gly Glu Ile Leu Gly Gln Leu Asp Val Lys Leu Leu
        210                 215                 220

Lys Ser Leu Ile Glu Gln Glu Ala Ala His Glu Pro Thr His His Glu
225                 230                 235                 240

Thr Ser Gln Pro Ser Ala Cys Gln Ala Gly Glu Ser Pro Ser
                245                 250

<210> SEQ ID NO 9
<211> LENGTH: 1377
<212> TYPE: DNA
<213> ORGANISM: Homo sapiens

<400> SEQUENCE: 9

| | |
|---|---|
| atggcttggg caagtaggct gggcctgctg ctggcactgc tgctgcccgt ggtcggtgcc | 60 |
| tccacgccag gcaccgtggt ccgactcaac aaggcagcat tgagctacgt gtctgaaatt | 120 |
| gggaaagccc ctctccagcg ggccctgcag gtcactgtcc ctcatttcct ggactggagt | 180 |
| ggagaggcgc ttcagcccac caggatccgg attctgaatg tccatgtgcc ccgcctccac | 240 |
| ctgaaattca ttgctggttt cggagtgcgc ctgctggcag cagctaattt tactttcaag | 300 |
| gtctttcgcg ccccagagcc cctggagctg acgctgcctg tggaactgct ggctgacacc | 360 |
| cgcgtgaccc agagctccat caggacccct gtggtcagca tctctgcctg ctctttattc | 420 |
| tcgggccacg ccaacgagtt tgatggcagt aacagcacct cccacgcgct gctggtcctg | 480 |
| gtgcagaagc acattaaagc tgtcttgagt aacaagctgt gcctgagcat ctccaacctg | 540 |
| gtgcagggtg tcaatgtcca cctgggcacc ttaattggcc tcaacccgt gggtcctgag | 600 |
| tcccagatcc gctattccat ggtcagtgtg cccactgtca ccagtgacta catttccctg | 660 |
| gaagtcaatg ctgttctctt cctgctgggc aagcccatca tcctgcccac ggatgccacc | 720 |
| ccttttgtgt tgccaaggca tgtgggtacc gagggctcca tggccaccgt gggcctctcc | 780 |
| cagcagctgt ttgactctgc gctcctgctg ctgcagaagg ccggtgccct caacctggac | 840 |
| atcacagggc agctgaggtc ggatgacaac ctgctgaaca cctctgctct gggccggctc | 900 |
| atcccggagg tggcccgcca gtttcccgag cccatgcctg tggtgctcaa ggtgcggctg | 960 |
| ggtgccacac ctgtggccat gctccacaca aacaacgcca cctgcggct gcagcccttc | 1020 |
| gtggaggtcc tggccacagc ctccaactcg gctttccagt ccctcttctc cctggatgtg | 1080 |
| gtagtgaact tgagactcca gctctctgtg tccaaggtga agcttcaggg gaccacgtct | 1140 |
| gtgctggggg atgtccagct cacggtggcc tcctccaacg tgggcttcat tgatacagat | 1200 |
| caggtgcgca cactgatggg caccgttttt gagaagcccc tgctggacca tctcaatgct | 1260 |
| ctcttggcca tgggaattgc cctccctggt gtggtcaacc tccactatgt cgcccctgag | 1320 |
| atctttgtct atgagggcta cgtggtgata tccagtggac tcttctacca gagctga | 1377 |

<210> SEQ ID NO 10
<211> LENGTH: 458
<212> TYPE: PRT
<213> ORGANISM: Homo sapiens

<400> SEQUENCE: 10

Met Ala Trp Ala Ser Arg Leu Gly Leu Leu Ala Leu Leu Leu Pro
  1               5                  10                  15

Val Val Gly Ala Ser Thr Pro Gly Thr Val Val Arg Leu Asn Lys Ala
                20                  25                  30

Ala Leu Ser Tyr Val Ser Glu Ile Gly Lys Ala Pro Leu Gln Arg Ala
            35                  40                  45

-continued

Leu Gln Val Thr Val Pro His Phe Leu Asp Trp Ser Gly Glu Ala Leu
 50                  55                  60

Gln Pro Thr Arg Ile Arg Ile Leu Asn Val His Val Pro Arg Leu His
 65                  70                  75                  80

Leu Lys Phe Ile Ala Gly Phe Gly Val Arg Leu Leu Ala Ala Ala Asn
                 85                  90                  95

Phe Thr Phe Lys Val Phe Arg Ala Pro Glu Pro Leu Glu Leu Thr Leu
            100                 105                 110

Pro Val Glu Leu Leu Ala Asp Thr Arg Val Thr Gln Ser Ser Ile Arg
            115                 120                 125

Thr Pro Val Val Ser Ile Ser Ala Cys Ser Leu Phe Ser Gly His Ala
        130                 135                 140

Asn Glu Phe Asp Gly Ser Asn Ser Thr Ser His Ala Leu Leu Val Leu
145                 150                 155                 160

Val Gln Lys His Ile Lys Ala Val Leu Ser Asn Lys Leu Cys Leu Ser
                165                 170                 175

Ile Ser Asn Leu Val Gln Gly Val Asn Val His Leu Gly Thr Leu Ile
            180                 185                 190

Gly Leu Asn Pro Val Gly Pro Glu Ser Gln Ile Arg Tyr Ser Met Val
        195                 200                 205

Ser Val Pro Thr Val Thr Ser Asp Tyr Ile Ser Leu Glu Val Asn Ala
    210                 215                 220

Val Leu Phe Leu Gly Lys Pro Ile Ile Leu Pro Thr Asp Ala Thr
225                 230                 235                 240

Pro Phe Val Leu Pro Arg His Val Gly Thr Gly Ser Met Ala Thr
                245                 250                 255

Val Gly Leu Ser Gln Gln Leu Phe Asp Ser Ala Leu Leu Leu Gln
            260                 265                 270

Lys Ala Gly Ala Leu Asn Leu Asp Ile Thr Gly Gln Leu Arg Ser Asp
        275                 280                 285

Asp Asn Leu Leu Asn Thr Ser Ala Leu Gly Arg Leu Ile Pro Glu Val
    290                 295                 300

Ala Arg Gln Phe Pro Glu Pro Met Pro Val Val Leu Lys Val Arg Leu
305                 310                 315                 320

Gly Ala Thr Pro Val Ala Met Leu His Thr Asn Asn Ala Thr Leu Arg
                325                 330                 335

Leu Gln Pro Phe Val Glu Val Leu Ala Thr Ala Ser Asn Ser Ala Phe
            340                 345                 350

Gln Ser Leu Phe Ser Leu Asp Val Val Asn Leu Arg Leu Gln Leu
        355                 360                 365

Ser Val Ser Lys Val Lys Leu Gln Gly Thr Thr Ser Val Leu Gly Asp
    370                 375                 380

Val Gln Leu Thr Val Ala Ser Ser Asn Val Gly Phe Ile Asp Thr Asp
385                 390                 395                 400

Gln Val Arg Thr Leu Met Gly Thr Val Phe Glu Lys Pro Leu Leu Asp
                405                 410                 415

His Leu Asn Ala Leu Leu Ala Met Gly Ile Ala Leu Pro Gly Val Val
            420                 425                 430

Asn Leu His Tyr Val Ala Pro Glu Ile Phe Val Tyr Glu Gly Tyr Val
        435                 440                 445

Val Ile Ser Ser Gly Leu Phe Tyr Gln Ser
    450                 455

<210> SEQ ID NO 11

```
<211> LENGTH: 1454
<212> TYPE: DNA
<213> ORGANISM: Homo sapiens

<400> SEQUENCE: 11
atgcagccag tcatgctggc cctgtggtcc ctgcttctgc tctggggcct ggcgactcca      60
tgccaggagc tgctagagac ggtgggcacg ctcgctcgga ttgacaagga tgaactcggc     120
aaagccatcc agaactcact ggttgggggag cccattctgc agaatgtgct gggatcggtc    180
acagctgtga accggggcct cttgggctca ggagggctgc ttggaggagg cggcttgctg     240
ggccacggag gggttttttgg cgttgtcgag gagctctctg gtctgaagat tgaggagctc     300
acgctgccaa aggtgttgct gaagctgctg ccgggatttg gggtgcagct gagcctgcac     360
accaaagtgg gcatgcattg ctccggcccc cttggtggcc ttctgcagct ggctgcggag     420
gtgaacgtga catcgcgggt ggcgctggcc gtgagctcaa ggggcacacc catccttatc     480
ctcaagcgct gcagcacgct cctgggccac atcagcctgt tctcagggct gctgcccaca     540
ccactctttg gggtcgtgga acagatgctc ttcaaggtgc ttccgggact gctgtgcccc     600
gtggtggaca gtgtgctggg tgtggtgaat gagctcctgg gggctgtgct gggcctggtg     660
tccccttggg ctcttgggtc cgtggaattc tctctggcca cattgcctct catctccaac     720
cagtacatag aactggacat caaccctatc gtgaagagtg tagctggtga tatcattgac     780
ttccccaagt cccgtgcccc agccaaggtg ccccccaaga aggaccacac atcccaggtg     840
atggtgccac tgtacctctt caacaccacg tttggactcc tgcagaccaa cggcgccctc     900
gacatggaca tcaccctga gctggttccc agcgatgtcc cactgacaac tacagacctg     960
gcagctttgc tccctgaggc cctggggaag ctgcccctgc accagcaact cctactgttc    1020
ctgcgggtga gggaagctcc cacggtcaca ctccacaaca agaaggcctt ggtctccctc    1080
ccagccaaca tccatgtgct gttctatgtc cctaagggga ccctgaatc cctctttgag    1140 ctgaactccg tcatgactgt gcgtgcccag ctggctccct cggctaccaa gctgcacatc    1200
tccctgtccc tggaacggct cagtgtcaag gtggcctcct cctttaccca tgcctttgac    1260
ggatcgcgtt tagaagaatg gctcagccat gtggtcgggg cagtgtatgc accaaagctt    1320
aacgtggccc tggatgttgg aattccctg cctaaggttc ttaatatcaa ttttttccaat    1380 tcagttctgg agatcgtaga gaatgctgtt gtgctgaccg tggcatcctg aggctgagac    1440
atggccacca gcct                                                      1454

<210> SEQ ID NO 12
<211> LENGTH: 476
<212> TYPE: PRT
<213> ORGANISM: Homo sapiens

<400> SEQUENCE: 12
```

Met Gln Pro Val Met Leu Ala Leu Trp Ser Leu Leu Leu Trp Gly
 1               5                  10                  15

Leu Ala Thr Pro Cys Gln Glu Leu Leu Glu Thr Val Gly Thr Leu Ala
                20                  25                  30

Arg Ile Asp Lys Asp Glu Leu Gly Lys Ala Ile Gln Asn Ser Leu Val
            35                  40                  45

Gly Glu Pro Ile Leu Gln Asn Val Leu Gly Ser Val Thr Ala Val Asn
        50                  55                  60

Arg Gly Leu Leu Gly Ser Gly Gly Leu Leu Gly Gly Gly Leu Leu
    65                  70                  75                  80

Gly His Gly Gly Val Phe Gly Val Val Glu Glu Leu Ser Gly Leu Lys

```
                    85                  90                  95
Ile Glu Glu Leu Thr Leu Pro Lys Val Leu Lys Leu Leu Pro Gly
                100                 105                 110

Phe Gly Val Gln Leu Ser Leu His Thr Lys Val Gly Met His Cys Ser
            115                 120                 125

Gly Pro Leu Gly Gly Leu Leu Gln Leu Ala Ala Glu Val Asn Val Thr
130                 135                 140

Ser Arg Val Ala Leu Ala Val Ser Ser Arg Gly Thr Pro Ile Leu Ile
145                 150                 155                 160

Leu Lys Arg Cys Ser Thr Leu Leu Gly His Ile Ser Leu Phe Ser Gly
                165                 170                 175

Leu Leu Pro Thr Pro Leu Phe Gly Val Glu Gln Met Leu Phe Lys
                180                 185                 190

Val Leu Pro Gly Leu Leu Cys Pro Val Val Asp Ser Val Leu Gly Val
                195                 200                 205

Val Asn Glu Leu Leu Gly Ala Val Leu Gly Leu Val Ser Leu Gly Ala
                210                 215                 220

Leu Gly Ser Val Glu Phe Ser Leu Ala Thr Leu Pro Leu Ile Ser Asn
225                 230                 235                 240

Gln Tyr Ile Glu Leu Asp Ile Asn Pro Ile Val Lys Ser Val Ala Gly
                245                 250                 255

Asp Ile Ile Asp Phe Pro Lys Ser Arg Ala Pro Ala Lys Val Pro Pro
                260                 265                 270

Lys Lys Asp His Thr Ser Gln Val Met Val Pro Leu Tyr Leu Phe Asn
                275                 280                 285

Thr Thr Phe Gly Leu Leu Gln Thr Asn Gly Ala Leu Asp Met Asp Ile
290                 295                 300

Thr Pro Glu Leu Val Pro Ser Asp Val Pro Leu Thr Thr Asp Leu
305                 310                 315                 320

Ala Ala Leu Leu Pro Glu Ala Leu Gly Lys Leu Pro Leu His Gln Gln
                325                 330                 335

Leu Leu Leu Phe Leu Arg Val Arg Glu Ala Pro Thr Val Thr Leu His
                340                 345                 350

Asn Lys Lys Ala Leu Val Ser Leu Pro Ala Asn Ile His Val Leu Phe
                355                 360                 365

Tyr Val Pro Lys Gly Thr Pro Glu Ser Leu Phe Glu Leu Asn Ser Val
                370                 375                 380

Met Thr Val Arg Ala Gln Leu Ala Pro Ser Ala Thr Lys Leu His Ile
385                 390                 395                 400

Ser Leu Ser Leu Glu Arg Leu Ser Val Lys Val Ala Ser Ser Phe Thr
                405                 410                 415

His Ala Phe Asp Gly Ser Arg Leu Glu Glu Trp Leu Ser His Val Val
                420                 425                 430

Gly Ala Val Tyr Ala Pro Lys Leu Asn Val Ala Leu Asp Val Gly Ile
                435                 440                 445

Pro Leu Pro Lys Val Leu Asn Ile Asn Phe Ser Asn Ser Val Leu Glu
                450                 455                 460

Ile Val Glu Asn Ala Val Val Leu Thr Val Ala Ser
465                 470                 475

<210> SEQ ID NO 13
<211> LENGTH: 2059
<212> TYPE: DNA
<213> ORGANISM: Homo sapiens
```

<400> SEQUENCE: 13

```
atgctgcagc aaagtgatgc tctccactcg gccctgagag aggtgccctt gggtgttggt      60
gatattccct acaatgactt ccatgtccga ggaccccccc cagtatatac caacggcaaa     120
aaacttgatg gtatttacca gtatggtcac attgagacca cgacaacac tgctcagctg      180
gggggcaaat accgatatgg tgagatcctt gagtccgagg aagcatcag ggacctccga      240
aacagtggct atcgcagtgc cgagaatgca tatgaggcc acaggggcct cgggcgatac      300
agggcagcac ctgtgggcag gcttcaccgg cgagagctgc agcctggaga atcccacct      360
ggagttgcca ctgggcggt gggcccaggt ggtttgctgg cactggagg catgctggca      420
gctgatggca tcctcgcagg ccaaggtggc ctgctcggcg gaggtggtct ccttggtgat    480
ggaggacttc ttggaggagg gggtgtcctg gcgtgctcg gcgagggtgg catcctcagc     540
actgtgcaag gcatcacggg gctgcgtatc gtggagctga ccctccctcg ggtgtccgtg    600
cggctcctgc ccggcgtggg tgtctacctg agcttgtaca cccgtgtggc catcaacggg    660
aagagtctta ttggcttcct ggacatcgca gtagaagtga acatcacagc caaggtccgg    720
ctgaccatgg accgcacggg ttatcctcgg ctggtcattg agcgatgtga caccctccta    780
ggggcatca aagtcaagct gctgcgaggg cttctcccca atctcgtgga caatttagtg     840
aaccgagtcc tggccgacgt cctccctgac ttgctctgcc ccatcgtgga tgtggtgctg    900
ggtcttgtca atgaccagct gggcctcgtg gattctctga ttcctctggg gatattggga    960
agtgtccagt acaccttctc cagcctcccg cttgtgaccg gggaattcct ggagctggac   1020
ctcaacacgc tggttgggga ggctggagga ggactcatcg actacccatt ggggtggcca   1080
gctgtgtctc ccaagccgat gccagagctg cctcccatgg gtgacaacac caagtcccag   1140
ctggccatgt ctgccaactt cctgggctca gtgctgactc tactgcagaa gcagcatgct   1200
ctagacctgg atatcaccaa tggcatgttt gaagagcttc ctccacttac cacagccaca   1260
ctgggagccc tgatccccaa ggtgttccag cagtaccccg agtcctgccc acttatcatc   1320
aggatccagg tgctgaaccc accatctgtg atgctgcaga aggacaaagc gctggtgaag   1380
gtgttggcca ctgccgaggt catggtctcc cagcccaaag acctggagac taccatctgc   1440
ctcattgacg tggacacaga attcttggcc tcattttcca cagaaggaga taagctcatg   1500
attgatgcca agctggagaa gaccagcctc aacctcagaa cctcaaacgt gggcaacttt   1560
gatattggcc tcatggaggt gctggtggag aagattttg acctggcatt catgcccgca    1620
atgaacgctg tgctgggttc tggcgtccct ctccccaaaa tcctcaacat cgactttagc   1680
aatgcagaca ttgacgtgtt ggaggacctt ttggtgctga gcgcatgagt gacagaggca   1740
gagatgctgc tgcaactgga agaagctgga accagtccca gagaggctcg gcctggaaac   1800
agtcccctgc ccagagtccc ctcagcctcc atgacaggtc cctccctggc ccccaacccc   1860
tcttcctccc ttgccccaac cctgagaaag ggtccagcca ctaccctgtt ggcaaacatt   1920
cccttccatg gtcagcctgc caggaggagg ggagtcacct tggggctgga ggcctctcag   1980
accccatcct gacagcaggt tgagtattcc cactttcaat aaaagactcc actttcccgg   2040
caaaaaaaaa aaaaaaaa                                                  2059
```

<210> SEQ ID NO 14
<211> LENGTH: 575
<212> TYPE: PRT
<213> ORGANISM: Homo sapiens

<400> SEQUENCE: 14

```
Met Leu Gln Gln Ser Asp Ala Leu His Ser Ala Leu Arg Glu Val Pro
 1               5                  10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
            35                  40                  45

Gly His Ile Glu Thr Asn Asp Asn Thr Ala Gln Leu Gly Gly Lys Tyr
        50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
            100                 105                 110

Leu Gln Pro Gly Glu Ile Pro Pro Gly Val Ala Thr Gly Ala Val Gly
        115                 120                 125

Pro Gly Gly Leu Leu Gly Thr Gly Gly Met Leu Ala Ala Asp Gly Ile
    130                 135                 140

Leu Ala Gly Gln Gly Gly Leu Leu Gly Gly Gly Leu Leu Gly Asp
145                 150                 155                 160

Gly Gly Leu Leu Gly Gly Gly Val Leu Gly Val Leu Gly Glu Gly
                165                 170                 175

Gly Ile Leu Ser Thr Val Gln Gly Ile Thr Gly Leu Arg Ile Val Glu
            180                 185                 190

Leu Thr Leu Pro Arg Val Ser Val Arg Leu Leu Pro Gly Val Gly Val
        195                 200                 205

Tyr Leu Ser Leu Tyr Thr Arg Val Ala Ile Asn Gly Lys Ser Leu Ile
210                 215                 220

Gly Phe Leu Asp Ile Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Asn Arg Val Leu Ala Asp Val Leu
        275                 280                 285

Pro Asp Leu Leu Cys Pro Ile Val Asp Val Leu Gly Leu Val Asn
    290                 295                 300

Asp Gln Leu Gly Leu Val Asp Ser Leu Ile Pro Leu Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Leu
            340                 345                 350

Ile Asp Tyr Pro Leu Gly Trp Pro Ala Val Ser Pro Lys Pro Met Pro
        355                 360                 365

Glu Leu Pro Pro Met Gly Asp Asn Thr Lys Ser Gln Leu Ala Met Ser
    370                 375                 380

Ala Asn Phe Leu Gly Ser Val Leu Thr Leu Gln Lys Gln His Ala
385                 390                 395                 400

Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
            420                 425                 430
```

```
Pro Glu Ser Cys Pro Leu Ile Ile Arg Ile Gln Val Leu Asn Pro Pro
            435                 440                 445

Ser Val Met Leu Gln Lys Asp Lys Ala Leu Val Lys Val Leu Ala Thr
    450                 455                 460

Ala Glu Val Met Val Ser Gln Pro Lys Asp Leu Glu Thr Thr Ile Cys
465                 470                 475                 480

Leu Ile Asp Val Asp Thr Glu Phe Leu Ala Ser Phe Ser Thr Glu Gly
                485                 490                 495

Asp Lys Leu Met Ile Asp Ala Lys Leu Glu Lys Thr Ser Leu Asn Leu
            500                 505                 510

Arg Thr Ser Asn Val Gly Asn Phe Asp Ile Gly Leu Met Glu Val Leu
        515                 520                 525

Val Glu Lys Ile Phe Asp Leu Ala Phe Met Pro Ala Met Asn Ala Val
    530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 15
<211> LENGTH: 278
<212> TYPE: PRT
<213> ORGANISM: Mus musculus

<400> SEQUENCE: 15

Met Phe Leu Val Gly Ser Leu Val Val Leu Cys Gly Leu Leu Ala His
1               5                   10                  15

Ser Thr Ala Gln Leu Ala Gly Leu Pro Leu Pro Leu Gly Gln Gly Pro
            20                  25                  30

Pro Leu Pro Leu Asn Gln Gly Pro Pro Leu Pro Leu Asn Gln Gly Gln
        35                  40                  45

Leu Leu Pro Leu Ala Gln Gly Leu Pro Leu Ala Val Ser Pro Ala Leu
    50                  55                  60

Pro Ser Asn Pro Thr Asp Leu Leu Ala Gly Lys Phe Thr Asp Ala Leu
65                  70                  75                  80

Ser Gly Gly Leu Leu Ser Gly Leu Leu Gly Ile Leu Glu Asn Ile
                85                  90                  95

Pro Leu Leu Asp Val Ile Lys Ser Gly Gly Asn Ser Asn Gly Leu
            100                 105                 110

Val Gly Gly Leu Leu Gly Lys Leu Thr Ser Ser Val Pro Leu Leu Asn
        115                 120                 125

Asn Ile Leu Asp Ile Lys Ile Thr Asp Pro Gln Leu Leu Glu Leu Gly
130                 135                 140

Leu Val Gln Ser Pro Asp Gly His Arg Leu Tyr Val Thr Ile Pro Leu
145                 150                 155                 160

Gly Leu Thr Leu Asn Val Asn Met Pro Val Val Gly Ser Leu Leu Gln
                165                 170                 175

Leu Ala Val Lys Leu Asn Ile Thr Ala Glu Val Leu Ala Val Lys Asp
            180                 185                 190

Asn Gln Gly Arg Ile His Leu Val Leu Gly Asp Cys Thr His Ser Pro
        195                 200                 205

Gly Ser Leu Lys Ile Ser Leu Leu Asn Gly Val Thr Pro Val Gln Ser
    210                 215                 220

Phe Val Asp Asn Leu Thr Gly Ile Leu Thr Lys Val Leu Pro Glu Leu
225                 230                 235                 240
```

```
Ile Gln Gly Lys Val Cys Pro Leu Val Asn Gly Ile Leu Ser Gly Leu
                245                 250                 255

Asp Val Thr Leu Val His Asn Ile Ala Glu Leu Leu Ile His Gly Leu
            260                 265                 270

Gln Phe Val Ile Lys Val
        275

<210> SEQ ID NO 16
<211> LENGTH: 270
<212> TYPE: PRT
<213> ORGANISM: Rattus norvegicus

<400> SEQUENCE: 16

Met Phe Leu Val Gly Ser Leu Val Val Leu Cys Gly Leu Leu Ala Gln
 1               5                  10                  15

Ser Thr Ala Gln Leu Ala Gly Leu Pro Leu Pro Leu Gly Gln Gly Leu
            20                  25                  30

Pro Leu Pro Leu Gly Gln Gly Leu Pro Leu Pro Leu Gly Gln Gly Leu
        35                  40                  45

Pro Leu Ala Val Ser Pro Ala Leu Pro Ser Asn Pro Thr Asp Leu Leu
    50                  55                  60

Ala Gly Asn Phe Ala Asn Ala Leu Ser Gly Gly Leu Leu Ser Gly Gly
65                  70                  75                  80

Leu Leu Gly Ile Leu Glu Asn Ile Pro Leu Leu Asp Val Ile Lys Ser
                85                  90                  95

Gly Gly Gly Ser Ser Asn Gly Leu Val Gly Gly Leu Leu Gly Lys Leu
            100                 105                 110

Thr Ser Ser Val Pro Leu Leu Asn Asn Ile Leu Asp Ile Lys Ile Thr
        115                 120                 125

Asp Pro Arg Leu Leu Glu Leu Gly Leu Val Gln Ser Pro Asp Gly His
    130                 135                 140

Arg Leu Tyr Ala Thr Ile Pro Leu Ser Leu Lys Leu Gln Val Asn Met
145                 150                 155                 160

Pro Val Val Gly Ser Phe Leu Gln Leu Ala Val Lys Leu Asn Ile Thr
                165                 170                 175

Ala Glu Ile Val Ala Met Lys Asp Asn Gln Gly Arg Ile His Leu Val
            180                 185                 190

Leu Gly Asp Cys Thr His Ser Pro Gly Ser Leu Gln Ile Thr Leu Leu
        195                 200                 205

Asn Gly Val Thr Pro Val Gln Ser Ser Leu Asp Ser Leu Thr Gly Ile
    210                 215                 220

Leu Thr Lys Val Leu Pro Glu Leu Ile Gln Gly Lys Val Cys Pro Leu
225                 230                 235                 240

Ile Asn Gly Ile Leu Ser Gly Leu Asp Val Thr Leu Val His Asn Ile
                245                 250                 255

Ala Glu Leu Leu Ile Gly His Ile Gln Phe Val Ile Lys Val
            260                 265                 270

<210> SEQ ID NO 17
<211> LENGTH: 256
<212> TYPE: PRT
<213> ORGANISM: Pan troglodytes
<220> FEATURE:
<221> NAME/KEY: misc_feature
<222> LOCATION: (243)..(243)
<223> OTHER INFORMATION: Xaa can be any naturally occurring amino acid

<400> SEQUENCE: 17
```

Met Phe Gln Thr Gly Gly Leu Ile Val Phe Cys Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
            35                  40                  45

Gly Ser Leu Thr Asn Ala Leu Ser Asn Gly Leu Leu Ser Gly Gly Leu
        50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Leu Leu Gly Lys Val Thr
                85                  90                  95

Ser Val Ile Pro Gly Leu Asn Asn Ile Ile Asp Ile Lys Val Thr Asp
                100                 105                 110

Pro Gln Leu Leu Glu Leu Gly Leu Val Gln Ser Pro Asp Gly His Arg
            115                 120                 125

Leu Tyr Val Thr Ile Pro Phe Gly Ile Lys Leu Gln Val Asn Thr Pro
        130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Ser Gly Leu Asp Ile Thr Leu Val His
225                 230                 235                 240

Asp Ile Xaa Asp Met Leu Ile His Gly Leu Gln Phe Ile Ile Lys Val
                245                 250                 255

<210> SEQ ID NO 18
<211> LENGTH: 255
<212> TYPE: PRT
<213> ORGANISM: Canis familiaris

<400> SEQUENCE: 18

Met Phe Gln Thr Gly Gly Leu Ile Val Phe Cys Gly Leu Leu Ala Gln
1               5                   10                  15

Thr Thr Thr Leu Leu Glu Ala Leu Ser Leu Pro Leu Glu His Thr Leu
            20                  25                  30

Phe Leu Glu Ala Thr Pro Gly Gln Asp Pro Ser Pro Thr Asp Leu Ala
            35                  40                  45

Gly Asp Leu Thr Asp Gly Leu Ser Ser Gly Leu Leu Ser Gly Gly Leu
        50                  55                  60

Leu Asp Ile Leu Glu Asn Leu Pro Leu Leu Asn Ile Leu Lys Thr Gly
65                  70                  75                  80

Gly Gly Thr Ser Gly Gly Leu Leu Gly Leu Leu Gly Lys Val Thr
                85                  90                  95

Ser Met Val Pro Leu Leu Asp Ser Ile Ile Glu Leu Lys Ile Thr Asn
                100                 105                 110

Pro Gln Leu Leu Glu Leu Gly Leu Val Gln Ser Pro Asp Gly His Arg
            115                 120                 125

```
Leu Tyr Val Thr Ile Pro Leu Gly Ile Val Leu Asn Val Asn Thr Pro
    130                 135                 140
Leu Thr Ser Ser Leu Val Lys Leu Ala Val Lys Leu Asn Ile Thr Ala
145                 150                 155                 160
Glu Ile Leu Ala Val Lys Asn Asp Gln Gly Lys Ile His Leu Ile Leu
                165                 170                 175
Gly Asp Cys Thr His Ser Pro Gly Ser Leu Gln Ile Ser Leu Leu Asn
            180                 185                 190
Gly Phe Ala Pro Leu Pro Val Gln Ser Leu Val Asp Ser Leu Ser Ser
        195                 200                 205
Phe Leu Asn Lys Val Leu Pro Glu Leu Val Gln Gly Glu Val Cys Pro
    210                 215                 220
Leu Val Asn Glu Val Leu Ser Glu Leu Asp Val Thr Leu Val His Ser
225                 230                 235                 240
Ile Ala Glu Leu Leu Ile Gly His Leu Glu Phe Val Ile Lys Val
                245                 250                 255

<210> SEQ ID NO 19
<211> LENGTH: 255
<212> TYPE: PRT
<213> ORGANISM: Bos taurus

<400> SEQUENCE: 19

Met Phe His Ile Gly Ser Leu Val Val Leu Cys Gly Leu Leu Ala Pro
1               5                   10                  15
Thr Thr Ala Leu Leu Glu Ala Leu Pro Thr Pro Leu Gly Gln Thr Leu
            20                  25                  30
Pro Leu Ala Val Thr Pro Ala Leu Ala Pro Ser Pro Pro Asp Leu Ala
        35                  40                  45
Gly Ser Leu Thr Gly Ala Leu Ser Asn Gly Leu Leu Ser Glu Gly Leu
    50                  55                  60
Leu Gly Ile Leu Glu Asn Leu Pro Leu Leu Asp Ile Leu Lys Thr Arg
65                  70                  75                  80
Gly Asn Ala Pro Ser Gly Leu Leu Gly Ser Leu Leu Gly Lys Val Thr
                85                  90                  95
Ser Leu Thr Pro Leu Leu Asn Asn Ile Ile Glu Leu Lys Ile Thr Asn
            100                 105                 110
Pro Gln Leu Leu Glu Leu Gly Leu Val Gln Ser Pro Asp Gly His Arg
        115                 120                 125
Leu Tyr Val Thr Ile Pro Leu Gly Met Ile Leu Asn Val Lys Thr Ser
    130                 135                 140
Leu Val Gly Ser Leu Leu Lys Leu Ala Val Lys Leu Asn Ile Thr Val
145                 150                 155                 160
Glu Leu Leu Ala Val Thr Asp Glu Gln Lys His Val His Leu Val Val
                165                 170                 175
Gly Asn Gly Thr His Ser Pro Gly Ser Leu Gln Ile Phe Leu Leu Asp
            180                 185                 190
Gly Leu Gly Ser Leu Pro Ile Gln Ser Phe Val Asp Asn Leu Thr Gly
        195                 200                 205
Ile Leu Asn Asp Val Leu Pro Gly Leu Val Gln Gly Lys Val Cys Pro
    210                 215                 220
Leu Val Asn Ala Val Leu Ser Arg Leu Asp Val Thr Leu Val His Ser
225                 230                 235                 240
Ile Val Asn Ala Leu Ile Gly His Leu Gln Phe Val Ile Lys Val
                245                 250                 255
```

<210> SEQ ID NO 20
<211> LENGTH: 249
<212> TYPE: PRT
<213> ORGANISM: Sus scrofa

<400> SEQUENCE: 20

```
Met Phe Gln Val Ala Gly Leu Ile Val Phe Cys Gly Leu Leu Ala Gln
 1               5                  10                  15

Thr Thr Ala Leu Leu Glu Ala Leu Pro Leu Gly Lys Ala Leu Pro Leu
             20                  25                  30

Ala Leu Asp Gln Ser Pro Thr Asp Leu Val Gly Ser Leu Thr Ser Thr
         35                  40                  45

Leu Ser Asn Gly Leu Leu Ser Glu Gly Val Leu Gly Ile Leu Gly Asn
     50                  55                  60

Leu Pro Leu Leu Asp Ile Leu Lys Ala Gly Gly Asn Thr Pro Ser Gly
 65                  70                  75                  80

Leu Leu Gly Gly Leu Leu Gly Lys Leu Ser Thr Ile Pro Leu Leu
                 85                  90                  95

Asn Asp Ile Val Asp Leu Gln Ile Thr Asp Pro Gln Leu Leu Glu Leu
                100                 105                 110

Gly Leu Val Gln Ser Pro Asp Gly His Arg Leu Tyr Val Thr Ile Pro
            115                 120                 125

Leu Ser Leu Val Leu Asn Val Lys Thr Ser Val Val Gly Ser Leu Leu
        130                 135                 140

Lys Leu Ala Val Lys Leu Asn Ile Thr Val Glu Leu Leu Ala Val Lys
145                 150                 155                 160

Asp Glu Gln Gly Lys Ser His Leu Val Leu Gly Asp Cys Thr His Ser
                165                 170                 175

Pro Gly Ser Leu Lys Ile Ser Leu Leu Asp Gly Leu Gly Pro Leu Val
            180                 185                 190

Pro Gln Asp Leu Leu Asp Ser Ile Thr Gly Val Leu Asp Asn Val Leu
        195                 200                 205

Pro Gly Leu Val Gln Gly Glu Val Cys Pro Leu Val Asn Glu Val Leu
    210                 215                 220

Ser His Leu Asp Val Thr Leu Val His Ser Ile Val Asp Ala Leu Ile
225                 230                 235                 240

Gln Gly Gln Glu Phe Val Ile Lys Val
                245
```

<210> SEQ ID NO 21
<211> LENGTH: 208
<212> TYPE: PRT
<213> ORGANISM: Equus caballus

<400> SEQUENCE: 21

```
Gln Gln Ile Pro Pro Glu Val Ser Ser Gln Ile Thr Asp Ala Leu Thr
 1               5                  10                  15

Gln Gly Leu Leu Asp Gly Asn Phe Leu Ser Leu Leu Asn Ala Ile Asn
             20                  25                  30

Leu Glu Gly Leu Leu Asn Thr Ile Leu Asp Gln Val Thr Gly Leu Leu
         35                  40                  45

Asn Ile Leu Val Gly Pro Leu Leu Gly Pro Ser Asn Ala Glu Ile Lys
     50                  55                  60

Leu Gln Asp Ala Arg Leu Leu Gln Leu Ser Leu Glu Phe Ser Pro Asp
 65                  70                  75                  80
```

```
Ser Lys Gly Ile Asp Ile Trp Ile Pro Leu Glu Leu Ser Val Tyr Leu
            85                  90                  95

Lys Leu Leu Ile Leu Glu Pro Leu Thr Leu Tyr Val Arg Thr Asp Ile
            100                 105                 110

Arg Val Gln Leu Gln Leu Glu Ser Asp Glu Asp Gly Lys Tyr Arg Leu
            115                 120                 125

Ala Phe Gly His Cys Ser Leu Leu Pro Arg Ala Ile Glu Leu Gln Ser
            130                 135                 140

Gly Asn Pro Leu Ser Leu Thr Val Asn Ala Val Leu Gly Thr Ile Glu
145                 150                 155                 160

Asn Ala Leu Gly Asn Phe Ile Thr Glu Asp Leu Gly Ala Glu Leu Cys
                165                 170                 175

Pro Thr Leu Asn Leu Leu Val Ser Asn Leu Asp Leu Gln Leu Val Asn
                180                 185                 190

Asn Leu Ile Asn Leu Ile Leu Asp Arg Ala Asn Val Asp Leu Ser Val
            195                 200                 205

<210> SEQ ID NO 22
<211> LENGTH: 207
<212> TYPE: PRT
<213> ORGANISM: Equus caballus

<400> SEQUENCE: 22

Gln Gln Ile Pro Pro Glu Val Ser Ser Gln Ile Thr Asp Ala Leu Thr
1               5                   10                  15

Gln Gly Leu Leu Asp Gly Asn Phe Leu Ser Leu Leu Asn Ala Ile Asn
            20                  25                  30

Leu Glu Gly Leu Leu Asn Thr Ile Leu Asp Gln Val Thr Gly Leu Leu
        35                  40                  45

Asn Ile Leu Val Gly Pro Leu Leu Gly Pro Ser Asn Ala Glu Ile Lys
    50                  55                  60

Leu Gln Asp Ala Arg Leu Leu Gln Leu Ser Leu Glu Phe Ser Pro Asp
65                  70                  75                  80

Ser Lys Gly Ile Asp Ile Trp Ile Pro Leu Glu Leu Ser Val Tyr Leu
            85                  90                  95

Lys Leu Leu Ile Leu Glu Pro Leu Thr Leu Tyr Val Arg Thr Asn Ile
            100                 105                 110

Arg Val Gln Leu Gln Leu Glu Ser Asp Glu Asp Gly Lys Tyr Arg Leu
            115                 120                 125

Ala Phe Gly His Cys Ser Leu Leu Pro Arg Ala Ile Glu Leu Gln Ser
            130                 135                 140

Gly Asn Pro Leu Ser Leu Thr Val Asn Ala Val Leu Gly Thr Ile Glu
145                 150                 155                 160

Asn Ala Leu Gly Asn Phe Ile Thr Glu Asp Leu Gly Ala Glu Leu Cys
                165                 170                 175

Pro Thr Leu Asn Ser Leu Val Ser Asn Leu Asp Leu Gln Leu Val Asn
                180                 185                 190

Asn Leu Ile Asn Leu Ile Leu Asp Arg Ala Asn Val Asp Leu Ser
            195                 200                 205

<210> SEQ ID NO 23
<211> LENGTH: 208
<212> TYPE: PRT
<213> ORGANISM: Equus caballus

<400> SEQUENCE: 23

Gln Gln Ile Pro Pro Glu Val Ser Ser Gln Ile Thr Asp Ala Leu Thr
```

```
               1               5                  10                 15
         Gln Gly Leu Leu Asp Gly Asn Phe Leu Ser Leu Leu Asn Ala Ile Asn
                         20                  25                  30

Leu Glu Gly Leu Leu Asn Thr Ile Leu Asp Gln Val Thr Gly Leu Leu
                     35                  40                  45

Asn Ile Leu Val Gly Pro Leu Leu Gly Pro Ser Asp Ala Glu Ile Lys
                 50                  55                  60

Leu Gln Asp Ala Arg Leu Leu Gln Leu Ser Leu Glu Phe Ser Pro Asp
         65                  70                  75                  80

Ser Lys Gly Ile Asp Ile Trp Ile Pro Leu Glu Leu Ser Val Tyr Leu
                         85                  90                  95

Lys Leu Leu Ile Leu Glu Pro Leu Thr Leu Tyr Val Arg Thr Asp Ile
                     100                 105                 110

Arg Val Gln Leu Gln Leu Glu Ser Asp Glu Asp Gly Lys Tyr Arg Leu
                 115                 120                 125

Ala Phe Gly His Cys Ser Leu Leu Pro Arg Ala Ile Glu Leu Gln Ser
             130                 135                 140

Gly Asn Pro Leu Ser Leu Pro Val Asn Ala Val Leu Gly Thr Ile Glu
         145                 150                 155                 160

Asn Ala Leu Gly Asn Phe Ile Thr Glu Asp Leu Gly Ala Glu Leu Cys
                         165                 170                 175

Pro Thr Leu Asn Ser Leu Val Ser Asn Leu Asp Leu Gln Leu Val Asn
                     180                 185                 190

Asn Leu Ile Asn Leu Ile Leu Asp Arg Ala Asn Val Asp Leu Ser Val
                 195                 200                 205

<210> SEQ ID NO 24
<211> LENGTH: 205
<212> TYPE: PRT
<213> ORGANISM: Equus zebra

<400> SEQUENCE: 24

Gln Gln Ile Pro Pro Glu Val Ser Ser Gln Ile Thr Asp Ala Leu Thr
         1               5                   10                  15

Gln Gly Leu Leu Asp Gly Asn Phe Leu Ser Leu Leu Asn Ala Ile Asn
                         20                  25                  30

Leu Glu Gly Leu Leu Asn Thr Ile Leu Asp Gln Val Thr Gly Leu Leu
                     35                  40                  45

Asn Ile Leu Val Gly Pro Leu Leu Gly Ser Ser Asn Ala Glu Ile Lys
                 50                  55                  60

Leu Gln Asp Ala Arg Leu Leu Gln Leu Ser Leu Glu Phe Ser Pro Asp
         65                  70                  75                  80

Ser Lys Gly Ile Asp Ile Trp Ile Pro Leu Glu Leu Ser Val Tyr Leu
                         85                  90                  95

Lys Leu Leu Ile Leu Glu Pro Leu Thr Leu Tyr Val Arg Thr Asp Ile
                     100                 105                 110

Arg Ala Gln Leu Gln Leu Glu Ser Asp Glu Asp Gly Lys Tyr Arg Leu
                 115                 120                 125

Ala Phe Gly His Cys Thr Leu Leu Pro Arg Ala Ile Glu Leu Gln Thr
             130                 135                 140

Gly Asn Pro Leu Ser Leu Thr Val Asn Ala Val Leu Gly Thr Ile Glu
         145                 150                 155                 160

Asn Thr Leu Gly Asn Phe Ile Thr Glu Asp Leu Gly Ala Gly Leu Cys
                         165                 170                 175

Pro Thr Leu Asn Ser Leu Val Ser Asn Leu Asn Leu Gln Leu Val Asn
```

-continued

```
            180                 185                 190

Asn Leu Ile Asn Leu Ile Leu Asp Arg Ala Asn Val Asp
        195                 200                 205
```